(12) United States Patent
Jones et al.

(10) Patent No.: US 10,428,048 B2
(45) Date of Patent: Oct. 1, 2019

(54) ANDROGEN RECEPTOR ANTAGONISTS

(71) Applicant: CITY OF HOPE, Duarte, CA (US)

(72) Inventors: Jeremy Jones, Pasadena, CA (US);
Sumanta Kumar Pal, Brea, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 15/757,238

(22) PCT Filed: Sep. 2, 2016

(86) PCT No.: PCT/US2016/050270
§ 371 (c)(1),
(2) Date: Mar. 2, 2018

(87) PCT Pub. No.: WO2017/041040
PCT Pub. Date: Mar. 9, 2017

(65) Prior Publication Data
US 2018/0244650 A1 Aug. 30, 2018

Related U.S. Application Data

(60) Provisional application No. 62/214,613, filed on Sep. 4, 2015.

(51) Int. Cl.
*C07D 401/14* (2006.01)
*C07D 401/06* (2006.01)
*A61P 35/00* (2006.01)

(52) U.S. Cl.
CPC ............ *C07D 401/14* (2013.01); *A61P 35/00* (2018.01); *C07D 401/06* (2013.01)

(58) Field of Classification Search
CPC .......................... C07D 401/06; C07D 401/14
See application file for complete search history.

(56) References Cited

U.S. PATENT DOCUMENTS

| | | | |
|---|---|---|---|
| 7,696,227 B2 | 4/2010 | Diamond et al. | |
| 8,119,660 B2 | 2/2012 | Diamond et al. | |
| 8,354,538 B2 | 1/2013 | Diamond et al. | |
| 8,580,773 B2 | 11/2013 | Diamond et al. | |
| 2008/0293766 A1 | 11/2008 | Diamond et al. | |

FOREIGN PATENT DOCUMENTS

| | | |
|---|---|---|
| CH | 509 382 A | 6/1971 |
| WO | WO-2006/078754 A1 | 7/2006 |
| WO | WO-2008/128100 A1 | 10/2008 |
| WO | WO-2009/132307 A1 | 10/2009 |

OTHER PUBLICATIONS

Voskoglou-Nomikos et al., Clinical Cancer Research, vol. 9, 4227-4239.*
ptcl.chenn.ox.ac.uk/MSDS structure activity relationship; Jaworska, 1-8, 2004.*
Cancer and Metastasis Reviews (1998), 17(1), 91-106.*
Science (1999), vol. 286, 531-537.*
Chou, T.C. et al. (1984). "Quantitative analysis of dose-effect relationships: the combined effects of multiple drugs or enzyme inhibitors," *Adv Enzyme Regul* 22:27-55.
Jones, J.O. et al. (Jul. 2008). "A cellular conformation-based screen for androgen receptor inhibitors," *ACS Chem Biol* 3(7):412-418.
Jones, J.O. et al. (Apr. 28, 2009, e-published Apr. 10, 2009). "Non-competitive androgen receptor inhibition in vitro and in vivo," *PNAS USA* 106(17):7233-7238.
Li, H. et al. (Aug. 1, 2014, e-published Aug. 4, 2014). "Discovery of small-molecule inhibitors selectively targeting the DNA-binding domain of the human androgen receptor," *J Med Chem* 57(15):6458-6467.
Xue, F. et al. (Nov. 19, 2009). Concise route to the chiral pyrrolidine core of selective inhibitors of neuronal nitric oxide, Org Lett 11(22):5194-5197.
International Search Report dated Dec. 15, 2016, for PCT Application No. PCT/US2016/050270, filed Sep. 2, 2016, 3 pages.
Written Opinion dated Dec. 15, 2016, for PCT Application No. PCT/US2016/050270, filed Sep. 2, 2016, 5 pages.

* cited by examiner

*Primary Examiner* — Rebecca L Anderson
(74) *Attorney, Agent, or Firm* — Mintz, Levin, Cohn, Ferris, Glovsky and Popeo, P.C.

(57) ABSTRACT

Disclosed herein are compositions and methods for modulating the androgen receptor.

20 Claims, 14 Drawing Sheets

Specification includes a Sequence Listing.

| Drug Combination | Cell type | Expected IC50 | Actual IC50 | Combination Index at f$_{50}$ (mutually non-exclusive assumption) |
|---|---|---|---|---|
| COH-P7:Bicalutamide 1:1 ratio | LNCaP | 113nM | 75nM | .33 |
| COH-P24:Bicalutamide 1:3 ratio | LNCaP | 40nM | 25nM | .32 |

FIG. 16

THE CONCENTRATION OF P24 IN MICROSOMES SOLUTION DURING INCUBATION (ng/ml)

| INCUBATION TIME (min) | P24 IN MOUSE MICROSOMES WITH NADPH | P24 IN MOUSE MICROSOMES WITHOUT NADPH | P24 IN HUMAN MICROSOMES WITH NADPH | P24 IN HUMAN MICROSOMES WITHOUT NADPH |
|---|---|---|---|---|
| 0 | 100 | 100 | 100 | 100 |
| 5 | 44.9905 | 92.4449 | 78.6814 | 94.2601 |
| 15 | 16.084 | 91.6694 | 51.4105 | 89.4015 |
| 30 | 6.5808 | 85.8417 | 39.5045 | 90.9105 |
| 60 | 2.942 | 78.981 | 24.4062 | 80.2312 |

SEQUENCE LISTING

```
<160> NUMBER OF SEQ ID NOS: 11

<210> SEQ ID NO 1
<211> LENGTH: 919
<212> TYPE: PRT
<213> ORGANISM: Artificial Sequence
<220> FEATURE:
<223> OTHER INFORMATION: Synthetic polypeptide

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
                100                 105                 110

Gln Pro Ser Gln Pro Gln Ser Ala Leu Glu Cys His Pro Glu Arg Gly
            115                 120                 125

Cys Val Pro Glu Pro Gly Ala Ala Val Ala Ala Ser Lys Gly Leu Pro
    130                 135                 140

Gln Gln Leu Pro Ala Pro Pro Asp Glu Asp Asp Ser Ala Ala Pro Ser
145                 150                 155                 160

Thr Leu Ser Leu Leu Gly Pro Thr Phe Pro Gly Leu Ser Ser Cys Ser
                165                 170                 175

Ala Asp Leu Lys Asp Ile Leu Ser Glu Ala Ser Thr Met Gln Leu Leu
            180                 185                 190

Gln Gln Gln Gln Gln Glu Ala Val Ser Glu Gly Ser Ser Ser Gly Arg
        195                 200                 205

Ala Arg Glu Ala Ser Gly Ala Pro Thr Ser Ser Lys Asp Asn Tyr Leu
    210                 215                 220

Gly Gly Thr Ser Thr Ile Ser Asp Asn Ala Lys Glu Leu Cys Lys Ala
225                 230                 235                 240

Val Ser Val Ser Met Gly Leu Gly Val Glu Ala Leu Glu His Leu Ser
```

-continued

```
                245                 250                 255
Pro Gly Glu Gln Leu Arg Gly Asp Cys Met Tyr Ala Pro Leu Leu Gly
            260                 265                 270
Val Pro Pro Ala Val Arg Pro Thr Pro Cys Ala Pro Leu Ala Glu Cys
            275                 280                 285
Lys Gly Ser Leu Leu Asp Asp Ser Ala Gly Lys Ser Thr Glu Asp Thr
            290                 295                 300
Ala Glu Tyr Ser Pro Phe Lys Gly Gly Tyr Thr Lys Gly Leu Glu Gly
305                 310                 315                 320
Glu Ser Leu Gly Cys Ser Gly Ser Ala Ala Gly Ser Ser Gly Thr
                325                 330                 335
Leu Glu Leu Pro Ser Thr Leu Ser Leu Tyr Lys Ser Gly Ala Leu Asp
            340                 345                 350
Glu Ala Ala Ala Tyr Gln Ser Arg Asp Tyr Tyr Asn Phe Pro Leu Ala
            355                 360                 365
Leu Ala Gly Pro Pro Pro Pro Pro Pro Pro His Pro His Ala Arg
            370                 375                 380
Ile Lys Leu Glu Asn Pro Leu Asp Tyr Gly Ser Ala Trp Ala Ala Ala
385                 390                 395                 400
Ala Ala Gln Cys Arg Tyr Gly Asp Leu Ala Ser Leu His Gly Ala Gly
                405                 410                 415
Ala Ala Gly Pro Gly Ser Gly Ser Pro Ser Ala Ala Ser Ser Ser
            420                 425                 430
Trp His Thr Leu Phe Thr Ala Glu Glu Gly Gln Leu Tyr Gly Pro Cys
            435                 440                 445
Gly Gly Gly Gly Gly Gly Gly Gly Gly Gly Gly Gly Gly Gly
            450                 455                 460
Gly Gly Gly Gly Gly Gly Gly Gly Glu Ala Gly Ala Val Ala Pro Tyr
465                 470                 475                 480
Gly Tyr Thr Arg Pro Pro Gln Gly Leu Ala Gly Gln Glu Ser Asp Phe
                485                 490                 495
Thr Ala Pro Asp Val Trp Tyr Pro Gly Gly Met Val Ser Arg Val Pro
                500                 505                 510
Tyr Pro Ser Pro Thr Cys Val Lys Ser Glu Met Gly Pro Trp Met Asp
            515                 520                 525
Ser Tyr Ser Gly Pro Tyr Gly Asp Met Arg Leu Glu Thr Ala Arg Asp
            530                 535                 540
His Val Leu Pro Ile Asp Tyr Tyr Phe Pro Pro Gln Lys Thr Cys Leu
545                 550                 555                 560
Ile Cys Gly Asp Glu Ala Ser Gly Cys His Tyr Gly Ala Leu Thr Cys
                565                 570                 575
Gly Ser Cys Lys Val Phe Phe Lys Arg Ala Ala Glu Gly Lys Gln Lys
            580                 585                 590
Tyr Leu Cys Ala Ser Arg Asn Asp Cys Thr Ile Asp Lys Phe Arg Arg
            595                 600                 605
Lys Asn Cys Pro Ser Cys Arg Leu Arg Lys Cys Tyr Glu Ala Gly Met
            610                 615                 620
Thr Leu Gly Ala Arg Lys Leu Lys Lys Leu Gly Asn Leu Lys Leu Gln
625                 630                 635                 640
Glu Glu Gly Glu Ala Ser Ser Thr Thr Ser Pro Thr Glu Glu Thr Thr
                645                 650                 655
Gln Lys Leu Thr Val Ser His Ile Glu Gly Tyr Glu Cys Gln Pro Ile
            660                 665                 670
```

```
Phe Leu Asn Val Leu Glu Ala Ile Glu Pro Gly Val Cys Ala Gly
            675                 680                 685

His Asp Asn Asn Gln Pro Asp Ser Phe Ala Ala Leu Leu Ser Ser Leu
690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
                740                 745                 750

Ser Phe Thr Asn Val Asn Ser Arg Met Leu Tyr Phe Ala Pro Asp Leu
            755                 760                 765

Val Phe Asn Glu Tyr Arg Met His Lys Ser Arg Met Tyr Ser Gln Cys
770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
            820                 825                 830

Asn Tyr Ile Lys Glu Leu Asp Arg Ile Ile Ala Cys Lys Arg Lys Asn
            835                 840                 845

Pro Thr Ser Cys Ser Arg Arg Phe Tyr Gln Leu Thr Lys Leu Leu Asp
850                 855                 860

Ser Val Gln Pro Ile Ala Arg Glu Leu His Gln Phe Thr Phe Asp Leu
865                 870                 875                 880

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
            900                 905                 910

Pro Ile Tyr Phe His Thr Gln
            915

<210> SEQ ID NO 2
<211> LENGTH: 920
<212> TYPE: PRT
<213> ORGANISM: Homo sapiens

<400> SEQUENCE: 2

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
                100                 105                 110

Glu Gln Gln Pro Ser Gln Pro Gln Ser Ala Leu Glu Cys His Pro Glu
```

```
                115                 120                 125
Arg Gly Cys Val Pro Glu Pro Gly Ala Val Ala Ala Ser Lys Gly
            130                 135                 140
Leu Pro Gln Gln Leu Pro Ala Pro Asp Glu Asp Ser Ala Ala
145                 150                 155                 160
Pro Ser Thr Leu Ser Leu Leu Gly Pro Thr Phe Pro Gly Leu Ser Ser
                165                 170                 175
Cys Ser Ala Asp Leu Lys Asp Ile Leu Ser Glu Ala Ser Thr Met Gln
            180                 185                 190
Leu Leu Gln Gln Gln Gln Glu Ala Val Ser Glu Gly Ser Ser Ser
            195                 200                 205
Gly Arg Ala Arg Glu Ala Ser Gly Ala Pro Thr Ser Ser Lys Asp Asn
            210                 215                 220
Tyr Leu Gly Gly Thr Ser Thr Ile Ser Asp Asn Ala Lys Glu Leu Cys
225                 230                 235                 240
Lys Ala Val Ser Val Ser Met Gly Leu Gly Val Glu Ala Leu Glu His
                245                 250                 255
Leu Ser Pro Gly Glu Gln Leu Arg Gly Asp Cys Met Tyr Ala Pro Leu
            260                 265                 270
Leu Gly Val Pro Pro Ala Val Arg Pro Thr Pro Cys Ala Pro Leu Ala
            275                 280                 285
Glu Cys Lys Gly Ser Leu Leu Asp Asp Ser Ala Gly Lys Ser Thr Glu
290                 295                 300
Asp Thr Ala Glu Tyr Ser Pro Phe Lys Gly Gly Tyr Thr Lys Gly Leu
305                 310                 315                 320
Glu Gly Glu Ser Leu Gly Cys Ser Gly Ser Ala Ala Ala Gly Ser Ser
                325                 330                 335
Gly Thr Leu Glu Leu Pro Ser Thr Leu Ser Leu Tyr Lys Ser Gly Ala
            340                 345                 350
Leu Asp Glu Ala Ala Ala Tyr Gln Ser Arg Asp Tyr Tyr Asn Phe Pro
            355                 360                 365
Leu Ala Leu Ala Gly Pro Pro Pro Pro Pro Pro Pro His Pro His
            370                 375                 380
Ala Arg Ile Lys Leu Glu Asn Pro Leu Asp Tyr Gly Ser Ala Trp Ala
385                 390                 395                 400
Ala Ala Ala Ala Gln Cys Arg Tyr Gly Asp Leu Ala Ser Leu His Gly
                405                 410                 415
Ala Gly Ala Ala Gly Pro Gly Ser Gly Ser Pro Ser Ala Ala Ala Ser
            420                 425                 430
Ser Ser Trp His Thr Leu Phe Thr Ala Glu Glu Gly Gln Leu Tyr Gly
            435                 440                 445
Pro Cys Gly Gly Gly Gly Gly Gly Gly Gly Gly Gly Gly
            450                 455                 460
Gly Gly Gly Gly Gly Gly Gly Gly Glu Ala Gly Ala Val Ala Pro
465                 470                 475                 480
Tyr Gly Tyr Thr Arg Pro Pro Gln Gly Leu Ala Gly Gln Glu Ser Asp
                485                 490                 495
Phe Thr Ala Pro Asp Val Trp Tyr Pro Gly Gly Met Val Ser Arg Val
            500                 505                 510
Pro Tyr Pro Ser Pro Thr Cys Val Lys Ser Glu Met Gly Pro Trp Met
            515                 520                 525
Asp Ser Tyr Ser Gly Pro Tyr Gly Asp Met Arg Leu Glu Thr Ala Arg
            530                 535                 540
```

```
Asp His Val Leu Pro Ile Asp Tyr Tyr Phe Pro Gln Lys Thr Cys
545                 550                 555                 560

Leu Ile Cys Gly Asp Glu Ala Ser Gly Cys His Tyr Gly Ala Leu Thr
            565                 570                 575

Cys Gly Ser Cys Lys Val Phe Phe Lys Arg Ala Ala Glu Gly Lys Gln
        580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
        610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
        675                 680                 685

Gly His Asp Asn Gln Pro Asp Ser Phe Ala Ala Leu Leu Ser Ser
        690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
        770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
        850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 3
<211> LENGTH: 18
<212> TYPE: DNA
<213> ORGANISM: Artificial Sequence
<220> FEATURE:
```

-continued

<223> OTHER INFORMATION: Synthetic polynucleotide

<400> SEQUENCE: 3
ccagaacatc aagaacag                                                    18

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 4
ctgttcttga tgttctgg                                                    18

<210> SEQ ID NO 5
<211> LENGTH: 920
<212> TYPE: PRT
<213> ORGANISM: Homo sapiens

<400> SEQUENCE: 5

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

```
Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
                340                 345                 350

Leu Asp Glu Ala Ala Ala Tyr Gln Ser Arg Asp Tyr Tyr Asn Phe Pro
                355                 360                 365

Leu Ala Leu Ala Gly Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
                420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
                500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
            530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
                660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
    690                 695                 700
```

```
Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
            725                 730                 735

Val Ile Gln Tyr Ser Trp Met Gly Leu Met Val Phe Ala Met Gly Trp
        740                 745                 750

Arg Ser Phe Thr Asn Val Asn Ser Arg Met Leu Tyr Phe Ala Pro Asp
    755                 760                 765

Leu Val Phe Asn Glu Tyr Arg Met His Lys Ser Arg Met Tyr Ser Gln
770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
            805                 810                 815

Ile Pro Val Asp Gly Leu Lys Asn Gln Lys Phe Phe Asp Glu Leu Arg
        820                 825                 830

Met Asn Tyr Ile Lys Glu Leu Asp Arg Ile Ile Ala Cys Lys Arg Lys
    835                 840                 845

Asn Pro Thr Ser Cys Ser Arg Arg Phe Tyr Gln Leu Thr Lys Leu Leu
850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
            885                 890                 895

Ala Glu Ile Ile Ser Val Gln Val Pro Lys Ile Leu Ser Gly Lys Val
        900                 905                 910

Lys Pro Ile Tyr Phe His Thr Gln
    915                 920

<210> SEQ ID NO 6
<211> LENGTH: 1329
<212> TYPE: DNA
<213> ORGANISM: Homo sapiens

<400> SEQUENCE: 6
gctgcgagca gagagggggtt cctcggaggt catctgttcc atcttcttgc ctatgcaaat    60
gcctgcctga agctgctgga ggctggcttt gtaccggact ttgtacaggg aaccagggaa   120
acgaatgcag agtgctcctg acattgcctg tcacttttc ccatgatact ctggcttcac    180
agtttggaga ctgccaggga ccatgttttg cccattgact attactttcc accccagaag   240
acctgcctga tctgtggaga tgaagcttct gggtgtcact atggagctct cacatgtgga   300
agctgcaagg tcttcttcaa aagagccgct gaagggaaac agaagtacct gtgcgccagc   360
agaaatgatt gcactattga taaattccga aggaaaaatt gtccatcttg tcgtcttcgg   420
aaatgttatg aagcagggat gactctggga gcccggaagc tgaagaaact tggtaatctg   480
aaactacagg aggaaggaga ggcttccagc accaccagcc ccactgagga caacccccag   540
aagctgacag tgtcacacat tgaaggctat gaatgtcagc ccatctttct gaatgtcctg   600
gaagccattg agccaggtgt agtgtgtgct ggacacgaca caaccagcc cgactccttt   660 gcagccttgc tctctagcct caatgaactg ggagagagac agcttgtaca cgtggtcaag   720
tgggccaagg ccttgcctgg cttccgcaac ttacacgtgg acgaccagat ggctgtcatt   780
cagtactcct ggatggggct catggtgttt gccatgggct ggcgatcctt caccaatgtc   840
aactccagga tgctctactt cgcccctgat ctggttttca atgagtaccg catgcacaag   900
```

```
tcccggatgt acagccagtg tgtccgaatg aggcacctct ctcaagagtt tggatggctc    960
caaatcaccc cccaggaatt cctgtgcatg aaagcactgc tactcttcag cattattcca   1020
gtggatgggc tgaaaaatca aaaattcttt gatgaacttc gaatgaacta catcaaggaa   1080
ctcgatcgta tcattgcatg caaaagaaaa atcccacat cctgctcaag acgcttctac    1140
cagctcacca agctcctgga ctccgtgcag cctattgcga gagagctgca tcagttcact   1200
tttgacctgc taatcaagtc acacatggtg agcgtggact ttccggaaat gatggcagag   1260
atcatctctg tgcaagtgcc aagatccttt ctgggaaag tcaagcccat ctatttccac    1320
acccagtga                                                           1329
```

<210> SEQ ID NO 7
<211> LENGTH: 645
<212> TYPE: PRT
<213> ORGANISM: Homo sapiens

<400> SEQUENCE: 7

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Glu Thr Ser Pro Arg Gln Gln Gln Gln Gln Gln
                85                  90                  95

Gly Glu Asp Gly Ser Pro Gln Ala His Arg Arg Gly Pro Thr Gly Tyr
            100                 105                 110

Leu Val Leu Asp Glu Glu Gln Gln Pro Ser Gln Pro Gln Ser Ala Leu
        115                 120                 125

Glu Cys His Pro Glu Arg Gly Cys Val Pro Glu Pro Gly Ala Ala Val
    130                 135                 140

Ala Ala Ser Lys Gly Leu Pro Gln Gln Leu Pro Ala Pro Pro Asp Glu
145                 150                 155                 160

Asp Asp Ser Ala Ala Pro Ser Thr Leu Ser Leu Leu Gly Pro Thr Phe
                165                 170                 175

Pro Gly Leu Ser Ser Cys Ser Ala Asp Leu Lys Asp Ile Leu Ser Glu
            180                 185                 190

Ala Ser Thr Met Gln Leu Leu Gln Gln Gln Gln Glu Ala Val Ser
        195                 200                 205

Glu Gly Ser Ser Ser Gly Arg Ala Arg Glu Ala Ser Gly Ala Pro Thr
    210                 215                 220

Ser Ser Lys Asp Asn Tyr Leu Gly Gly Thr Ser Thr Ile Ser Asp Asn
225                 230                 235                 240

Ala Lys Glu Leu Cys Lys Ala Val Ser Val Ser Met Gly Leu Gly Val
                245                 250                 255

Glu Ala Leu Glu His Leu Ser Pro Gly Glu Gln Leu Arg Gly Asp Cys
            260                 265                 270

Met Tyr Ala Pro Leu Leu Gly Val Pro Pro Ala Val Arg Pro Thr Pro
        275                 280                 285
```

Cys Ala Pro Leu Ala Glu Cys Lys Gly Ser Leu Leu Asp Asp Ser Ala
            290                 295                 300

Gly Lys Ser Thr Glu Asp Thr Ala Glu Tyr Ser Pro Phe Lys Gly Gly
305                 310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
                340                 345                 350

Tyr Lys Ser Gly Ala Leu Asp Glu Ala Ala Tyr Gln Ser Arg Asp
                355                 360                 365

Tyr Tyr Asn Phe Pro Leu Ala Leu Ala Gly Pro Pro Pro Pro Pro
370                 375                 380

Pro Pro His Pro His Ala Arg Ile Lys Leu Glu Asn Pro Leu Asp Tyr
385                 390                 395                 400

Gly Ser Ala Trp Ala Ala Ala Ala Gln Cys Arg Tyr Gly Asp Leu
                405                 410                 415

Ala Ser Leu His Gly Ala Gly Ala Ala Gly Pro Gly Ser Gly Ser Pro
                420                 425                 430

Ser Ala Ala Ser Ser Ser Trp His Thr Leu Phe Thr Ala Glu Glu
                435                 440                 445

Gly Gln Leu Tyr Gly Pro Cys Gly Gly Gly Gly Gly Gly Gly Gly
    450                 455                 460

Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
                500                 505                 510

Val Pro Tyr Pro Ser Pro Thr Cys Val Lys Ser Glu Met Gly Pro Trp
                515                 520                 525

Met Asp Ser Tyr Ser Gly Pro Tyr Gly Asp Met Arg Leu Glu Thr Ala
            530                 535                 540

Arg Asp His Val Leu Pro Ile Asp Tyr Tyr Phe Pro Pro Gln Lys Thr
545                 550                 555                 560

Cys Leu Ile Cys Gly Asp Glu Ala Ser Gly Cys His Tyr Gly Ala Leu
                565                 570                 575

Thr Cys Gly Ser Cys Lys Val Phe Phe Lys Arg Ala Ala Glu Gly Lys
                580                 585                 590

Gln Lys Tyr Leu Cys Ala Ser Arg Asn Asp Cys Thr Ile Asp Lys Phe
            595                 600                 605

Arg Arg Lys Asn Cys Pro Ser Cys Arg Leu Arg Lys Cys Tyr Glu Ala
610                 615                 620

Gly Met Thr Leu Gly Glu Lys Phe Arg Val Gly Asn Cys Lys His Leu
625                 630                 635                 640

Lys Met Thr Arg Pro
            645

<210> SEQ ID NO 8
<211> LENGTH: 648
<212> TYPE: PRT
<213> ORGANISM: Homo sapiens

<400> SEQUENCE: 8

Met Glu Val Gln Leu Gly Leu Gly Arg Val Tyr Pro Arg Pro Pro Ser
1               5                   10                  15

-continued

```
Lys Thr Tyr Arg Gly Ala Phe Gln Asn Leu Phe Gln Ser Val Arg Glu
             20                  25                  30

Val Ile Gln Asn Pro Gly Pro Arg His Pro Glu Ala Ala Ser Ala Ala
         35                  40                  45

Pro Pro Gly Ala Ser Leu Leu Leu Gln Gln Gln Gln Gln Gln Gln Gln
 50                  55                  60

Gln Gln Gln Gln Gln Gln Gln Gln Gln Gln Gln Gln Gln Gln Gln Gln
 65                  70                  75                  80

Gln Gln Gln Gln Glu Thr Ser Pro Arg Gln Gln Gln Gln Gln Gln Gly
                 85                  90                  95

Glu Asp Gly Ser Pro Gln Ala His Arg Arg Gly Pro Thr Gly Tyr Leu
             100                 105                 110

Val Leu Asp Glu Glu Gln Gln Pro Ser Gln Pro Gln Ser Ala Leu Glu
         115                 120                 125

Cys His Pro Glu Arg Gly Cys Val Pro Glu Pro Gly Ala Ala Val Ala
 130                 135                 140

Ala Ser Lys Gly Leu Pro Gln Gln Leu Pro Ala Pro Pro Asp Glu Asp
145                 150                 155                 160

Asp Ser Ala Ala Pro Ser Thr Leu Ser Leu Leu Gly Pro Thr Phe Pro
                 165                 170                 175

Gly Leu Ser Ser Cys Ser Ala Asp Leu Lys Asp Ile Leu Ser Glu Ala
             180                 185                 190

Ser Thr Met Gln Leu Leu Gln Gln Gln Gln Glu Ala Val Ser Glu
         195                 200                 205

Gly Ser Ser Ser Gly Arg Ala Arg Glu Ala Ser Gly Ala Pro Thr Ser
 210                 215                 220

Ser Lys Asp Asn Tyr Leu Gly Gly Thr Ser Thr Ile Ser Asp Asn Ala
225                 230                 235                 240

Lys Glu Leu Cys Lys Ala Val Ser Val Ser Met Gly Leu Gly Val Glu
                 245                 250                 255

Ala Leu Glu His Leu Ser Pro Gly Glu Gln Leu Arg Gly Asp Cys Met
             260                 265                 270

Tyr Ala Pro Leu Leu Gly Val Pro Pro Ala Val Arg Pro Thr Pro Cys
         275                 280                 285

Ala Pro Leu Ala Glu Cys Lys Gly Ser Leu Leu Asp Asp Ser Ala Gly
 290                 295                 300

Lys Ser Thr Glu Asp Thr Ala Glu Tyr Ser Pro Phe Lys Gly Gly Tyr
305                 310                 315                 320

Thr Lys Gly Leu Glu Gly Glu Ser Leu Gly Cys Ser Gly Ser Ala Ala
                 325                 330                 335

Ala Gly Ser Ser Gly Thr Leu Glu Leu Pro Ser Thr Leu Ser Leu Tyr
             340                 345                 350

Lys Ser Gly Ala Leu Asp Glu Ala Ala Tyr Gln Ser Arg Asp Tyr
         355                 360                 365

Tyr Asn Phe Pro Leu Ala Leu Ala Gly Pro Pro Pro Pro Pro Pro
 370                 375                 380

Pro His Pro His Ala Arg Ile Lys Leu Glu Asn Pro Leu Asp Tyr Gly
385                 390                 395                 400

Ser Ala Trp Ala Ala Ala Ala Gln Cys Arg Tyr Gly Asp Leu Ala
                 405                 410                 415

Ser Leu His Gly Ala Gly Ala Ala Gly Pro Gly Ser Gly Ser Pro Ser
             420                 425                 430
```

```
Ala Ala Ala Ser Ser Ser Trp His Thr Leu Phe Thr Ala Glu Glu Gly
            435                 440                 445

Gln Leu Tyr Gly Pro Cys Gly Gly Gly Gly Gly Gly Gly Gly Gly Gly
450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Ala Val Val Ser Glu Arg Ile Leu Arg Val
625                 630                 635                 640

Phe Gly Val Ser Glu Trp Leu Pro
                645

<210> SEQ ID NO 9
<211> LENGTH: 682
<212> TYPE: PRT
<213> ORGANISM: Homo sapiens

<400> SEQUENCE: 9

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Glu Thr Ser Pro Arg Gln Gln Gln Gln Gln Gln
                85                  90                  95

Gly Glu Asp Gly Ser Pro Gln Ala His Arg Arg Gly Pro Thr Gly Tyr
            100                 105                 110

Leu Val Leu Asp Glu Glu Gln Gln Pro Ser Gln Pro Gln Ser Ala Leu
        115                 120                 125

Glu Cys His Pro Glu Arg Gly Cys Val Pro Glu Pro Gly Ala Ala Val
    130                 135                 140

Ala Ala Ser Lys Gly Leu Pro Gln Gln Leu Pro Ala Pro Pro Asp Glu
145                 150                 155                 160
```

```
Asp Asp Ser Ala Ala Pro Ser Thr Leu Ser Leu Leu Gly Pro Thr Phe
            165                 170                 175

Pro Gly Leu Ser Ser Cys Ser Ala Asp Leu Lys Asp Ile Leu Ser Glu
        180                 185                 190

Ala Ser Thr Met Gln Leu Leu Gln Gln Gln Gln Glu Ala Val Ser
            195                 200                 205

Glu Gly Ser Ser Ser Gly Arg Ala Arg Glu Ala Ser Gly Ala Pro Thr
            210                 215                 220

Ser Ser Lys Asp Asn Tyr Leu Gly Gly Thr Ser Thr Ile Ser Asp Asn
225                 230                 235                 240

Ala Lys Glu Leu Cys Lys Ala Val Ser Val Ser Met Gly Leu Gly Val
                245                 250                 255

Glu Ala Leu Glu His Leu Ser Pro Gly Glu Gln Leu Arg Gly Asp Cys
            260                 265                 270

Met Tyr Ala Pro Leu Leu Gly Val Pro Pro Ala Val Arg Pro Thr Pro
            275                 280                 285

Cys Ala Pro Leu Ala Glu Cys Lys Gly Ser Leu Leu Asp Asp Ser Ala
        290                 295                 300

Gly Lys Ser Thr Glu Asp Thr Ala Glu Tyr Ser Pro Phe Lys Gly Gly
305                 310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
            340                 345                 350

Tyr Lys Ser Gly Ala Leu Asp Glu Ala Ala Tyr Gln Ser Arg Asp
        355                 360                 365

Tyr Tyr Asn Phe Pro Leu Ala Leu Ala Gly Pro Pro Pro Pro Pro
        370                 375                 380

Pro Pro His Pro His Ala Arg Ile Lys Leu Glu Asn Pro Leu Asp Tyr
385                 390                 395                 400

Gly Ser Ala Trp Ala Ala Ala Ala Gln Cys Arg Tyr Gly Asp Leu
                405                 410                 415

Ala Ser Leu His Gly Ala Gly Ala Ala Gly Pro Gly Ser Gly Ser Pro
            420                 425                 430

Ser Ala Ala Ser Ser Ser Trp His Thr Leu Phe Thr Ala Glu Glu
            435                 440                 445

Gly Gln Leu Tyr Gly Pro Cys Gly Gly Gly Gly Gly Gly Gly Gly
    450                 455                 460

Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
            500                 505                 510

Val Pro Tyr Pro Ser Pro Thr Cys Val Lys Ser Glu Met Gly Pro Trp
        515                 520                 525

Met Asp Ser Tyr Ser Gly Pro Tyr Gly Asp Met Arg Leu Glu Thr Ala
        530                 535                 540

Arg Asp His Val Leu Pro Ile Asp Tyr Tyr Phe Pro Pro Gln Lys Thr
545                 550                 555                 560

Cys Leu Ile Cys Gly Asp Glu Ala Ser Gly Cys His Tyr Gly Ala Leu
                565                 570                 575
```

```
Thr Cys Gly Ser Cys Lys Val Phe Phe Lys Arg Ala Ala Glu Gly Lys
            580                 585                 590

Gln Lys Tyr Leu Cys Ala Ser Arg Asn Asp Cys Thr Ile Asp Lys Phe
        595                 600                 605

Arg Arg Lys Asn Cys Pro Ser Cys Arg Leu Arg Lys Cys Tyr Glu Ala
610                 615                 620

Gly Met Thr Leu Gly Gly Phe Phe Arg Met Asn Lys Leu Lys Glu Ser
625                 630                 635                 640

Ser Asp Thr Asn Pro Lys Pro Tyr Cys Met Ala Ala Pro Met Gly Leu
                645                 650                 655

Thr Glu Asn Asn Arg Asn Arg Lys Lys Ser Tyr Arg Glu Thr Asn Leu
            660                 665                 670

Lys Ala Val Ser Trp Pro Leu Asn His Thr
        675                 680

<210> SEQ ID NO 10
<211> LENGTH: 643
<212> TYPE: PRT
<213> ORGANISM: Homo sapiens

<400> SEQUENCE: 10

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Glu Thr Ser Pro Arg Gln Gln Gln Gln Gln Gln
                85                  90                  95

Gly Glu Asp Gly Ser Pro Gln Ala His Arg Arg Gly Pro Thr Gly Tyr
            100                 105                 110

Leu Val Leu Asp Glu Glu Gln Gln Pro Ser Gln Pro Gln Ser Ala Leu
        115                 120                 125

Glu Cys His Pro Glu Arg Gly Cys Val Pro Glu Pro Gly Ala Ala Val
    130                 135                 140

Ala Ala Ser Lys Gly Leu Pro Gln Gln Leu Pro Ala Pro Pro Asp Glu
145                 150                 155                 160

Asp Asp Ser Ala Ala Pro Ser Thr Leu Ser Leu Leu Gly Pro Thr Phe
                165                 170                 175

Pro Gly Leu Ser Ser Cys Ser Ala Asp Leu Lys Asp Ile Leu Ser Glu
            180                 185                 190

Ala Ser Thr Met Gln Leu Leu Gln Gln Gln Gln Glu Ala Val Ser
        195                 200                 205

Glu Gly Ser Ser Ser Gly Arg Ala Arg Glu Ala Ser Gly Ala Pro Thr
    210                 215                 220

Ser Ser Lys Asp Asn Tyr Leu Gly Gly Thr Ser Thr Ile Ser Asp Asn
225                 230                 235                 240

Ala Lys Glu Leu Cys Lys Ala Val Ser Val Ser Met Gly Leu Gly Val
                245                 250                 255

Glu Ala Leu Glu His Leu Ser Pro Gly Glu Gln Leu Arg Gly Asp Cys
            260                 265                 270
```

```
Met Tyr Ala Pro Leu Leu Gly Val Pro Pro Ala Val Arg Pro Thr Pro
        275                 280                 285

Cys Ala Pro Leu Ala Glu Cys Lys Gly Ser Leu Leu Asp Asp Ser Ala
    290                 295                 300

Gly Lys Ser Thr Glu Asp Thr Ala Glu Tyr Ser Pro Phe Lys Gly Gly
305                 310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
            340                 345                 350

Tyr Lys Ser Gly Ala Leu Asp Glu Ala Ala Tyr Gln Ser Arg Asp
            355                 360                 365

Tyr Tyr Asn Phe Pro Leu Ala Leu Ala Gly Pro Pro Pro Pro Pro
370                 375                 380

Pro Pro His Pro His Ala Arg Ile Lys Leu Glu Asn Pro Leu Asp Tyr
385                 390                 395                 400

Gly Ser Ala Trp Ala Ala Ala Ala Gln Cys Arg Tyr Gly Asp Leu
                405                 410                 415

Ala Ser Leu His Gly Ala Gly Ala Ala Gly Pro Gly Ser Gly Ser Pro
            420                 425                 430

Ser Ala Ala Ser Ser Ser Trp His Thr Leu Phe Thr Ala Glu Glu
    435                 440                 445

Gly Gln Leu Tyr Gly Pro Cys Gly Gly Gly Gly Gly Gly Gly Gly
    450                 455                 460

Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
            500                 505                 510

Val Pro Tyr Pro Ser Pro Thr Cys Val Lys Ser Glu Met Gly Pro Trp
            515                 520                 525

Met Asp Ser Tyr Ser Gly Pro Tyr Gly Asp Met Arg Leu Glu Thr Ala
    530                 535                 540

Arg Asp His Val Leu Pro Ile Asp Tyr Tyr Phe Pro Pro Gln Lys Thr
545                 550                 555                 560

Cys Leu Ile Cys Gly Asp Glu Ala Ser Gly Cys His Tyr Gly Ala Leu
                565                 570                 575

Thr Cys Gly Ser Cys Lys Val Phe Phe Lys Arg Ala Ala Glu Gly Phe
            580                 585                 590

Phe Arg Met Asn Lys Leu Lys Glu Ser Ser Asp Thr Asn Pro Lys Pro
    595                 600                 605

Tyr Cys Met Ala Ala Pro Met Gly Leu Thr Glu Asn Asn Arg Asn Arg
610                 615                 620

Lys Lys Ser Tyr Arg Glu Thr Asn Leu Lys Ala Val Ser Trp Pro Leu
625                 630                 635                 640

Asn His Thr

<210> SEQ ID NO 11
<211> LENGTH: 739
<212> TYPE: PRT
<213> ORGANISM: Homo sapiens

<400> SEQUENCE: 11
```

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
                35                  40                  45

Pro Pro Gly Ala Ser Leu Leu Leu Gln Gln Gln Gln Gln Gln Gln Gln
50                      55                  60

Gln Gln Gln Gln Gln Gln Gln Gln Gln Gln Gln Gln Gln Gln Gln Gln
65                  70                  75                  80

Gln Glu Thr Ser Pro Arg Gln Gln Gln Gln Gln Gly Glu Asp Gly
                85                  90                  95

Ser Pro Gln Ala His Arg Arg Gly Pro Thr Gly Tyr Leu Val Leu Asp
                100                 105                 110

Glu Glu Gln Gln Pro Ser Gln Pro Gln Ser Ala Leu Glu Cys His Pro
                115                 120                 125

Glu Arg Gly Cys Val Pro Glu Pro Gly Ala Ala Val Ala Ala Ser Lys
            130                 135                 140

Gly Leu Pro Gln Gln Leu Pro Ala Pro Pro Asp Glu Asp Asp Ser Ala
145                 150                 155                 160

Ala Pro Ser Thr Leu Ser Leu Leu Gly Pro Thr Phe Pro Gly Leu Ser
                165                 170                 175

Ser Cys Ser Ala Asp Leu Lys Asp Ile Leu Ser Glu Ala Ser Thr Met
                180                 185                 190

Gln Leu Leu Gln Gln Gln Gln Glu Ala Val Ser Glu Gly Ser Ser
                195                 200                 205

Ser Gly Arg Ala Arg Glu Ala Ser Gly Ala Pro Thr Ser Ser Lys Asp
        210                 215                 220

Asn Tyr Leu Gly Gly Thr Ser Thr Ile Ser Asp Asn Ala Lys Glu Leu
225                 230                 235                 240

Cys Lys Ala Val Ser Val Ser Met Gly Leu Gly Val Glu Ala Leu Glu
                245                 250                 255

His Leu Ser Pro Gly Glu Gln Leu Arg Gly Asp Cys Met Tyr Ala Pro
                260                 265                 270

Leu Leu Gly Val Pro Pro Ala Val Arg Pro Thr Pro Cys Ala Pro Leu
            275                 280                 285

Ala Glu Cys Lys Gly Ser Leu Leu Asp Asp Ser Ala Gly Lys Ser Thr
            290                 295                 300

Glu Asp Thr Ala Glu Tyr Ser Pro Phe Lys Gly Gly Tyr Thr Lys Gly
305                 310                 315                 320

Leu Glu Gly Glu Ser Leu Gly Cys Ser Gly Ser Ala Ala Gly Ser
                325                 330                 335

Ser Gly Thr Leu Glu Leu Pro Ser Thr Leu Ser Leu Tyr Lys Ser Gly
                340                 345                 350

Ala Leu Asp Glu Ala Ala Ala Tyr Gln Ser Arg Asp Tyr Tyr Asn Phe
                355                 360                 365

Pro Leu Ala Leu Ala Gly Pro Pro Pro Pro Pro Pro Pro His Pro
370                 375                 380
```

```
His Ala Arg Ile Lys Leu Glu Asn Pro Leu Asp Tyr Gly Ser Ala Trp
385                 390                 395                 400

Ala Ala Ala Ala Ala Gln Cys Arg Tyr Gly Asp Leu Ala Ser Leu His
            405                 410                 415

Gly Ala Gly Ala Ala Gly Pro Gly Ser Gly Ser Pro Ser Ala Ala Ala
        420                 425                 430

Ser Ser Ser Trp His Thr Leu Phe Thr Ala Glu Glu Gly Gln Leu Tyr
    435                 440                 445

Gly Pro Cys Gly Gly Gly Gly Gly Gly Gly Gly Gly Gly Gly Gly Gly
450                 455                 460

Gly Gly Gly Gly Gly Gly Gly Gly Gly Gly Gly Gly Gly Gly Glu Ala
465                 470                 475                 480

Gly Ala Val Ala Pro Tyr Gly Tyr Thr Arg Pro Pro Gln Gly Leu Ala
            485                 490                 495

Gly Gln Glu Ser Asp Phe Thr Ala Pro Asp Val Trp Tyr Pro Gly Gly
            500                 505                 510

Met Val Ser Arg Val Pro Tyr Pro Ser Pro Thr Cys Val Lys Ser Glu
            515                 520                 525

Met Gly Pro Trp Met Asp Ser Tyr Ser Gly Pro Tyr Gly Asp Met Arg
            530                 535                 540

Leu Glu Thr Ala Arg Asp His Val Leu Pro Ile Asp Tyr Tyr Phe Pro
545                 550                 555                 560

Pro Gln Lys Thr Cys Leu Ile Cys Gly Asp Glu Ala Ser Gly Cys His
            565                 570                 575

Tyr Gly Ala Leu Thr Cys Gly Ser Cys Lys Val Phe Phe Lys Arg Ala
            580                 585                 590

Ala Glu Gly Lys Gln Lys Tyr Leu Cys Ala Ser Arg Asn Asp Cys Thr
            595                 600                 605

Ile Asp Lys Phe Arg Arg Lys Asn Cys Pro Ser Cys Arg Leu Arg Lys
            610                 615                 620

Cys Tyr Glu Ala Gly Met Thr Leu Gly Ala Arg Lys Leu Lys Lys Leu
625                 630                 635                 640

Gly Asn Leu Lys Leu Gln Glu Glu Gly Glu Ala Ser Ser Thr Thr Ser
            645                 650                 655

Pro Thr Glu Glu Thr Thr Gln Lys Leu Thr Val Ser His Ile Glu Gly
            660                 665                 670

Tyr Glu Cys Gln Pro Ile Phe Leu Asn Val Leu Glu Ala Ile Glu Pro
            675                 680                 685

Gly Val Val Cys Ala Gly His Asp Asn Asn Gln Pro Asp Ser Phe Ala
            690                 695                 700

Ala Leu Leu Ser Ser Leu Asn Glu Leu Gly Glu Arg Gln Leu Val His
705                 710                 715                 720

Val Val Lys Trp Ala Lys Ala Leu Pro Asp Cys Glu Arg Ala Ala Ser
            725                 730                 735

Val His Phe
```

ANDROGEN RECEPTOR ANTAGONISTS

CROSS-REFERENCES TO RELATED APPLICATIONS

This application is the national stage filing under USC 371 of international application PCT/US2016/050270, filed Sep. 2, 2016, which claims the benefit of U.S. Provisional Application No. 62/214,613, filed Sep. 4, 2015, which are incorporated hereby by reference in their entirety for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-546N01US_ST25.TXT, created Mar. 1, 2018, 55,202 bytes, machine format IBM-PC, MS-Windows operating system, is hereby incorporated herein by reference in its entirety and for all purposes.

BACKGROUND

Androgen receptor (AR) is a member of the nuclear hormone receptor family activated by androgens, such as dihydrotestosterone (DHT). AR is a prime therapeutic target for treating prostate cancer. Several compounds have been developed as chemotherapy for prostate cancer.

Androgen receptor competitive antagonists (antiandrogens) are drugs used to treat hormonal-based syndromes and prostate cancer. Current drugs for prostate cancer include flutamide, bicalutamide, nilutamide, enzalutamide and ARN-509. Each of these inhibitors binds to the hormone-binding pocket (HBP) of the androgen receptor. This is the same site that the natural physiological steroids testosterone (TES) and dihydrotestosterone (DHT) bind. The drugs work by competing with the natural hormones for binding to the pocket and, as a result, lessening activation of the receptor. Androgen receptor antagonists with different mechanisms of action and/or different binding sites would be complementary to the current commercially available antagonists.

Disclosed herein are solutions to these and other problems in the art.

BRIEF SUMMARY

In an aspect is provided a compound, or a pharmaceutically acceptable salt thereof, having the formula:

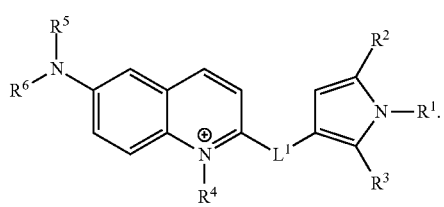

(I)

$R^1$ is hydrogen or substituted or unsubstituted pyrid-2-yl. $R^2$ is independently a hydrogen, halogen, $-CX^2_3$, $-CHX^2_2$, $-CH_2X^2$, $-CN$, $-SO_{n2}R^{10}$, $-SO_{v2}NR^7R^8$, $-NHNR^7R^8$, $-ONR^7R^8$, $-NHC=(O)NHNR^7R^8$, $-NHC=(O)NR^7R^8$, $-N(O)_{m2}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^2_3$, $-OCHX^2_2$, $-OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $-CX^3_3$, $-CHX^3_2$, $-CH_2X^3$, $-CN$, $-SO_{n3}R^{14}$, $-SO_{v3}NR^{11}R^{12}$, $-NHNH_2$, $-ONR^{11}R^{12}$, $-NHC=(O)NHNH_2$, $-NHC=(O)NR^{11}R^{12}$, $-N(O)_{m3}$, $-NR^{11}R^{12}$, $-C(O)R^{13}$, $-C(O)OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^3_3$, $-OCHX^3_2$, $-OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, $R^{13}$, and $R^{14}$ are independently hydrogen, halogen, $-CX_3$, $-CHX_2$, $-CH_2X$, $-OCX_3$, $-OCHX_2$, $-OCH_2X$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. $R^4$ is independently hydrogen, a $-CX^4_3$, $-CHX^4_2$, $-CH_2X^4$, $-CN$, $-C(O)H$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently a hydrogen, halogen, $-CX^5_3$, $-CHX^5_2$, $-CH_2X^5$, $-CN$, $-C(O)H$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is independently a hydrogen, halogen, $-CX^6_3$, $-CHX^6_2$, $-CH_2X^6$, $-CN$, $-C(O)H$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is independently a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene. The symbols m2, m3, v2, and v3 are independently 1 or 2. The symbols n2 and n3 are independently an integer from 0 to 4. X, $X^2$, $X^3$, $X^4$, $X^5$, and $X^6$ are independently $-Cl$, $-Br$, $-I$, or F.

In another aspect is provided a pharmaceutical composition including a pharmaceutically acceptable excipient and a compound, or pharmaceutically acceptable salt thereof, as described herein.

In another aspect is provided a method of treating a nuclear receptor activity-associated disease in a subject in need of such treatment, the method including administering a compound, or a pharmaceutically acceptable salt thereof, as described herein.

In another aspect is provided a method of treating cancer in a subject in need of such treatment, the method including administering a compound, or a pharmaceutically acceptable salt thereof, as described herein.

In another aspect is provided a method of inhibiting androgen receptor activity in a subject in need thereof, including administering to the subject a compound as described herein, or a pharmaceutically acceptable salt thereof.

In another aspect is provided a method of inhibiting androgen receptor activity, the method including contacting an androgen receptor with an effective amount of a compound described herein, or a pharmaceutically acceptable salt thereof.

BRIEF DESCRIPTION OF THE DRAWINGS

FIG. 4A: AR-V7; FIG. 4B: AR-$V^{567es}$. See Example 3.

FIG. 6A: P7; FIG. 6B: P24. See Example 10.

FIG. 16. P24 microsomal analysis.

DETAILED DESCRIPTION

Figure 1:
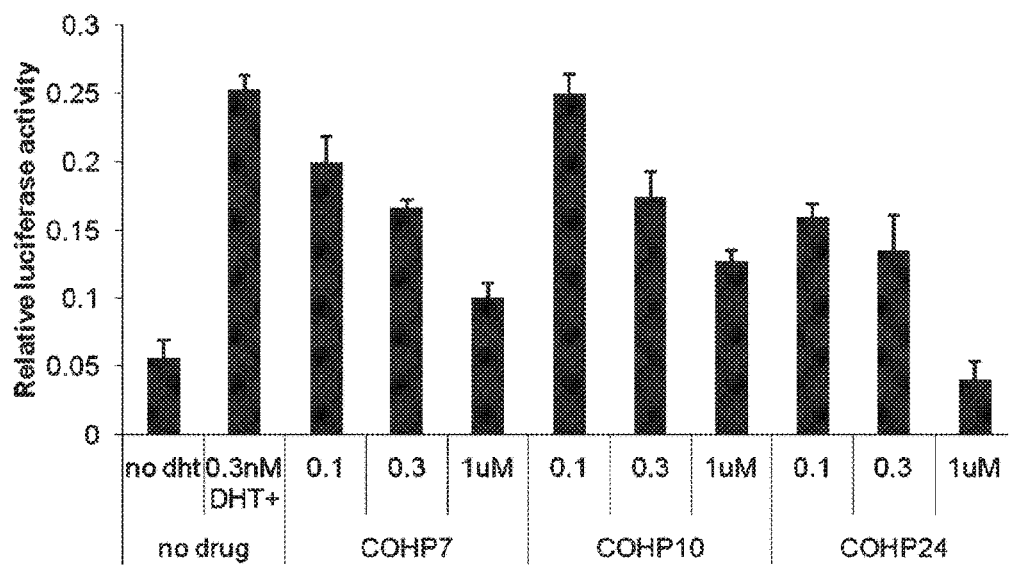
FIG. 1. Inhibition of AR activity in LNCaP cells. LNCaP cells were transfected with PSA-luciferase and a *renilla* control plasmid. The following day, quadruplicate wells were treated with 0.3 nM DHT and increasing concentrations of the indicated compound, or vehicle. Luciferase activity was assayed 24 hours later, and the *renilla*-normalized PSA-luciferase activity is shown.
Figure 2:
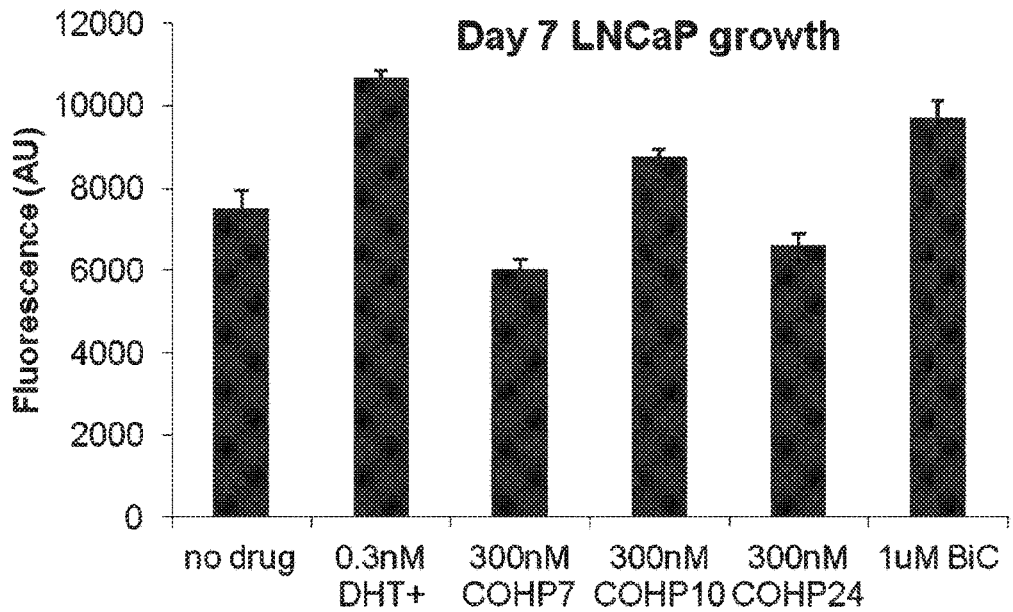
FIG. 2. LNCaP prostate cancer cells were grown for 7 days in the presence of the indicated compound (BiC=bicalutamide) and relative growth was assayed by DAPI staining of fixed cells and fluorescence measurement on a plate reader. Bars represent the standard error of conditions tested in quadruplicate.

The mainstay of current prostate cancer therapies are drugs that directly inhibit androgen receptor (AR) function by competitively inhibiting the binding of hormones (TES, DHT) to the receptor (e.g. Casodex, Flutamide, MDV3100, ARN-509). However, tumor cells become resistant to many antiandrogens within a few years of treatment and the progression of prostate cancer subsequently resumes. Described herein are novel compounds that inhibit AR through a different mechanism of action.

A. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds (alkenyl) or triple bonds (alkynyl). An alkenyl may include more than one double bond and/or one or more triple bonds in addition to the one or more double bonds. An alkynyl may include more than one triple bond and/or one or more double bonds in addition to the one or more triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkenylene," by itself or as part of another substituent, means, unless otherwise stated, a divalent radical derived from an alkyne. An alkenylene may include more than one double bond and/or one or more triple bonds in addition to the one or more double bonds. An alkynylene may include more than one triple bond and/or one or more double bonds in addition to the one or more triple bonds.

The term "heteroalkyl," by itself or in combination with another term, means, unless otherwise stated, a stable straight or branched non-cyclic chain, or combinations thereof, including at least one carbon atom and at least one heteroatom (e.g., selected from the group consisting of O, N, P, Si, and S), and wherein the nitrogen and sulfur atoms may optionally he oxidized, and the nitrogen heteroatom may optionally be quaternized. The heteroatom(s) (e.g., O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from heteroalkenyl. The term "heteroalkynylene," by itself or as part of another substituent, means, unless otherwise stated, a divalent radical derived from heteroalkynyl. A heteroalkenylene may optionally include more than one double bond and/or one or more triple bonds in additional to the one or more double bonds. A heteroalkynylene may optionally include more than one triple bond and/or one or more double bonds in additional to the one or more triple bonds.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P). A "cycloalkylene" and a "heterocycloalkylene," alone or as part of another substituent, means a divalent radical derived from a cycloalkyl and heterocycloalkyl, respectively. The terms "cycloalkenyl" and "cycloalkynyl," by themselves or in combination with other terms, mean, unless otherwise stated, cyclic versions of "alkenyl" and "alkynyl," respectively. The terms "heterocycloalkenyl" and "heterocycloalkynyl," by themselves or in combination with other terms, mean, unless otherwise stated, cyclic versions of "heteroalkenyl" and "heteroalkynyl," respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R", —ONR'R", —NR'C=(O)NR"N'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be Obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al. *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (±)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⁓" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with androgen receptor activity. Certain methods described herein may treat diseases associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism) by inhibiting androgen receptor activity. Certain methods described herein may treat diseases associated with androgen receptor activity by inhibiting coactivator or transcriptional proteins from binding to androgen receptor. For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease. In embodiments, treating is preventing. In embodiments, treating is not preventing.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with androgen receptor activity may be treated with an agent (e.g. compound as described herein) effective for decreasing the level of androgen receptor activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is an identical experiment or identical conditions without administration of a compound (e.g. a compound described herein). In embodiments, inhibition of an activity compared to a control is inhibition of an activity by a compound (e.g., as described herein) compared to the activity in the absence of the compound (e.g. as described herein).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is an androgen receptor antagonist. In embodiments, a modulator is a hormone receptor antagonist. In embodiments, a modulator is an androgen receptor inhibitor. In embodiments, a modulator is an androgen receptor agonist. An androgen receptor (AR) modulator is a composition that increases or decreases the level of AR (e.g, protein, mRNA) or the level of activity of AR (e.g., DNA binding, dimerization, co-factor binding, transcriptional activation, transcriptional activity, binding to a second protein, or androgen receptor activity). In embodiments, an AR modulator decreases the level of AR (e.g, protein, mRNA) or the level of activity of AR (e.g., DNA binding, dimerization, co-factor binding, transcriptional activation, transcriptional activity, binding to a second protein, or androgen receptor activity) (i.e., AR inhibitor). In embodiments, an AR modulator decreases the level of AR protein. In embodiments, an AR modulator decreases the level of AR mRNA. In embodiments, an AR modulator decreases the level of activity of AR. In embodiments, an AR modulator increases the level of AR (e.g, protein, mRNA) or the level of activity of AR (e.g., DNA binding, dimerization, co-factor binding, transcriptional activation, transcriptional activity, binding to a second protein, or androgen receptor activity) (i.e., AR activator).

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine daclixi-mab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of androgen receptor activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is prostate cancer. In embodiments, the disease is hormone sensitive prostate cancer. In embodiments, the disease is hormone refractory (insensitive) prostate cancer. In embodiments, the disease is bone cancer.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, *Rous sarcoma*, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99)%, by weight, of the total protein in a sample.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human androgen receptor protein and the overall structures compared.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g.

anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter cilia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or aberrant androgen receptor activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

A "drug-resistant androgen receptor" is a modified (relative to wildtype) androgen receptor that is inhibited less effectively by the drug than a wildtype androgen receptor. A "drug-resistant human androgen receptor" is a modified (relative to wildtype) human androgen receptor that is inhibited less effectively by the drug than a wildtype human androgen receptor. Examples of a "drug-resistant human androgen receptor" include a human androgen receptor with a level of activity that is less inhibited by a competitive inhibitor (e.g., Casodex, Flutamide, MDV3100, or ARN-509) then a wildtype human androgen inhibitor, a human androgen receptor that is active without binding a ligand, and a human androgen receptor that is active without a portion or all of the ligand binding domain.

The term "androgen receptor" or "AR" or "NR3C4" refers to a nuclear receptor activated by binding of the androgenic hormone testosterone or dihydrotestosterone. The term "androgen receptor" may refer to the nucleotide sequence or protein sequence of human androgen receptor (e.g., Entrez 367, Uniprot P10275, RefSeq NM_000044, or RefSeq NP_000035 (SEQ ID NO:2)). The term "androgen receptor" includes both the wild-type form of the nucleotide sequences or proteins as well as any mutants thereof. In some embodiments, "androgen receptor" is wild-type androgen receptor. In some embodiments, "androgen receptor" is one or more mutant forms. The term "androgen receptor" XYZ refers to a nucleotide sequence or protein of a mutant androgen receptor wherein the Y numbered amino acid of androgen receptor that normally has an X amino acid in the wildtype, instead has a Z amino acid in the mutant. In embodiments, an androgen receptor is the human androgen receptor. In embodiments, the androgen receptor has the nucleotide sequence corresponding to reference number GI:349501065. In embodiments, the androgen receptor has the nucleotide sequence corresponding to RefSeq NM_000044.3. In embodiments, the androgen receptor has the protein sequence corresponding to reference number GI:21322252. In embodiments, the androgen receptor has the protein sequence corresponding to RefSeq NP_000035.2. In embodiments, the androgen receptor has the following amino acid sequence:

```
(SEQ ID NO: 1)
MEVQLGLGRVYPRPPSKTYRGAFQNLFQSVREVIQNPGPRHPEAASAAPP

GASLLLLQQQQQQQQQQQQQQQQQQQQQQETSPRQQQQQQGEDGSPQAHRR

GPTGYLVLDEEQQPSQPQSALECHPERGCVPEPGAAVAASKGLPQQLPAP

PDEDDSAAPSTLSLLGPTFPGLSSCSADLKDILSEASTMQLLQQQQQEAV

SEGSSSGRAREASGAPTSSKDNYLGGTSTISDNAKELCKAVSVSMGLGVE

ALEHLSPGEQLRGDCMYAPLLGVPPAVRPTPCAPLAECKGSLLDDSAGKS

TEDTAEYSPFKGGYTKGLEGESLGCSGSAAAGSSGTLELPSTLSLYKSGA

LDEAAAYQSRDYYNFPLALAGPPPPPPPPHPHARIKLENPLDYGSAWAAA

AAQCRYGDLASLHGAGAAGPGSGSPSAAASSSWHTLFTAEEGQLYGPCGG

GGGGGGGGGGGGGGGGGGGGGEAGAVAPYGYTRPPQGLAGQESDFTAPD

VWYPGGMVSRVPYPSPTCVKSEMGPWMDSYSGPYGDMRLETARDHVLPID

YYFPPQKTCLICGDEASGCHYGALTCGSCKVFFKRAAEGKQKYLCASRND

CTIDKFRRKNCPSCRLRKCYEAGMTLGARKLKKLGNLKLQEEGEASSTTS

PTEETTQKLTVSHIEGYECQPIFLNVLEAIEPGVVCAGHDNNQPDSFAAL

LSSLNELGERQLVHVVKWAKALPGFRNLHVDDQMAVIQYSWMGLMVFAMG

WRSFTNVNSRMLYFAPDLVFNEYRMHKSRMYSQCVRMRHLSQEFGWLQIT

PQEFLCMKALLLFSIIPVDGLKNQKFFDELRMNYIKELDRIIACKRKNPT

SCSRRFYQLTKLLDSVQPIARELHQFTFDLLIKSHMVSVDFPEMMAEIIS

VQVPKILSGKVKPIYFHTQ.
```

In embodiments, the androgen receptor is a mutant androgen receptor. In embodiments, the mutant androgen receptor is associated with a disease that is not associated with wildtype androgen receptor. In embodiments, the androgen receptor includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above. In embodiments, the mutant androgen receptor is a splice variant. In embodiments, the mutant androgen receptor is lacking a portion of the ligand binding domain. In embodiments, the mutant androgen receptor is active in the absence of bound ligand. In embodiments, the mutant androgen receptor is lacking the ligand binding domain. In embodiments, the splice variant androgen receptor is AR variant 1 (e.g., GI:21322252 (SEQ ID NO:5)). In embodiments, the splice variant androgen receptor is AR variant 2 (AR45) (e.g., GI:21713434 (SEQ ID NO:6)). In embodiments, the splice variant androgen receptor is AR variant 3 (AR-V7) (e.g., GI:224181614 (SEQ ID NO:7)). In embodiments, the splice variant androgen receptor is AR variant 4 (AR-V1) (e.g., GI:224181616 (SEQ ID NO:8)). In embodiments, the splice variant androgen receptor is AR variant 5 (AR-V4) (e.g., GI:224181620 (SEQ ID NO:9)). In embodiments, the splice variant androgen receptor is AR variant 6 (AR-V3) (e.g., GI:224181622 (SEQ ID NO:10)). In embodiments, the splice variant androgen receptor is AR v567es (e.g., GI:270358642 (SEQ ID NO:11)).

B. COMPOUNDS

In an aspect is provided a compound, or a pharmaceutically acceptable salt thereof, having the formula:

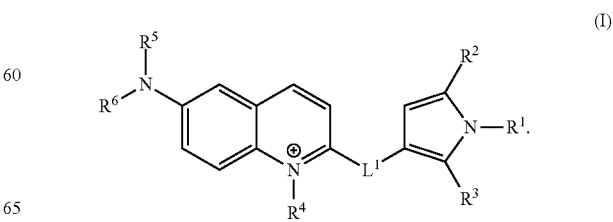

(I)

$R^1$ is hydrogen or substituted or unsubstituted pyrid-2-yl. $R^2$ is independently a hydrogen, halogen, $-CX^2_3$, $-CHX^2_2$, $-CH_2X^2$, $-CN$, $-SO_{n2}R^{10}$, $-SO_{v2}NR^7R^8$, $-NHNR^7R^8$, $-ONR^7R^8$, $-NHC=(O)NHNR^7R^8$, $-NHC=(O)NR^7R^8$, $-N(O)_{m2}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^2_3$, $-OCHX^2_2$, $-OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $-CX^3_3$, $-CHX^3_2$, $-CH_2X^3$, $-CN$, $-SO_{n3}R^{14}$, $-SO_{v3}NR^{11}R^{12}$, $-NHNH_2$, $-ONR^{11}R^{12}$, $-NHC=(O)NHNH_2$, $-NHC=(O)NR^{11}R^{12}$, $-N(O)_{m3}$, $-NR^{11}R^{12}$, $-C(O)R^{13}$, $-C(O)OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^3_3$, $-OCHX^3_2$, $-OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, $R^{13}$, and $R^{14}$ are independently hydrogen, halogen, $-CX_3$, $-CHX_2$, $-CH_2X$, $-OCX_3$, $-OCHX_2$, $-OCH_2X$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. $R^4$ is independently hydrogen, a $-CX^4_3$, $-CHX^4_2$, $-CH_2X^4$, $-CN$, $-C(O)H$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently a hydrogen, halogen, $-CX^5_3$, $-CHX^5_2$, $-CH_2X^5$, $-CN$, $-C(O)H$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is independently a hydrogen, halogen, $-CX^6_3$, $-CHX^6_2$, $-CH_2X^6$ $-CN$, $-C(O)H$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is independently a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene. The symbols m2, m3, v2, and v3 are independently 1 or 2. The symbols n2 and n3 are independently an integer from 0 to 4. X, $X^2$, $X^3$, $X^4$, $X^5$, and $X^6$ are independently $-Cl$, $-Br$, $-I$, or $-F$.

In embodiments, the compound has the formula

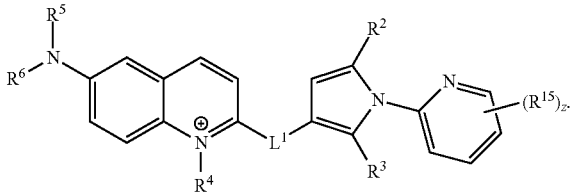

(II)

$L^1$, $R^2$, $R^3$, $R^4$, $R^5$, and $R^6$ are as described herein, including in embodiments (e.g., as for formula I and embodiments thereof).

In embodiments, the compound has the formula

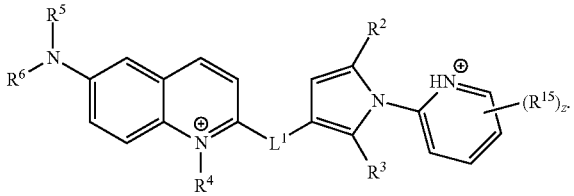

(IIa)

$L^1$, $R^2$, $R^3$, $R^4$, $R^5$, and $R^6$ are as described herein, including in embodiments (e.g., as for formula I and embodiments thereof).

$R^{15}$ is independently a halogen, $-CX^{15}_3$, $-CHX^{15}_2$, $-CH_2X^{15}$, $-CN$, $-SO_{n15}R^{19}$, $-SO_{v15}NR^{16}R^{17}$, $-NHNR^{16}R^{17}$, $-ONR^{16}R^{17}$, $-NHC=(O)NHNR^{16}R^{17}$, $-NHC=(O)NR^{16}R^{17}$, $-N(O)_{m15}$, $-NR^{16}R^{17}$, $-C(O)R^{18}$, $-C(O)-OR^{18}$, $-C(O)NR^{16}R^{17}$, $-OR^{19}$, $-NR^{16}SO_2R^{19}$, $-NR^{16}C=(O)R^{18}$, $-NR^{16}C(O)OR^{18}$, $-NR^{16}OR^{18}$, $-OCX^{15}_3$, $-OCHX^{15}_2$, $-OCH_2X^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$, $R^{17}$, $R^{18}$, and $R^{19}$ are independently hydrogen, halogen, $-CX_3$, $-CHX_2$, $-CH_2X$, $-OCX_3$, $-OCHX_2$, $-OCH_2X$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ and $R^{17}$ substituents bonded to the same nitrogen atom may optionally be joined to form a substituted or unsubstituted heterocycloalkyl or substituted or unsubstituted heteroaryl. The symbols m15 and v15 are independently 1 or 2. The symbol n15 is independently an integer from 0 to 4. The symbol z is an integer from 0 to 4. $X^{15}$ is independently $-Cl$, $-Br$, $-I$, or $-F$.

In embodiments, $R^{15}$ is independently a halogen, $-CX^{15}_3$, $-CHX^{15}_2$, $-CH_2X^{15}$, $-CN$, $-NHNH_2$, $-NO_2$, $-NH_2$, $-C(O)H$, $-C(O)OH$, $-C(O)NH_2$, $-OH$, $-NHC(O)OH$, $-OCX^{15}_3$, $-OCHX^{15}_2$, $-OCH_2X^{15}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{15}$ is independently a halogen, $-CX^{15}_3$, $-CHX^{15}_2$, $-CH_2X^{15}$, $-CN$, $-NH_2$, $-OH$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{15}$ is independently a halogen, $-CX^{15}_3$, $-CHX^{15}_2$, $-CH_2X^{15}$, $-CN$, $-NH_2$, $-OH$, unsubstituted $C_1$-$C_4$ alkyl, or unsubstituted 2 to 4 membered heteroalkyl. In embodiments, $R^{15}$ is independently a halogen, $-CF_3$, unsubstituted methyl, unsubstituted ethyl, unsubstituted isopropyl, unsubstituted methoxy, or unsubstituted ethoxy. In embodiments, $R^{15}$ is independently unsubstituted methyl.

In embodiments, the compound has the formula:

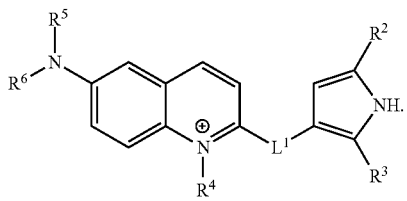

(III)

$L^1$, $R^2$, $R^3$, $R^4$, $R^5$, and $R^6$ are as described herein, including in embodiments (e.g., as for formula I and embodiments thereof).

In embodiments, $R^1$ is

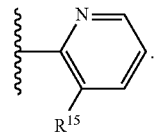

In embodiments, $R^1$ is

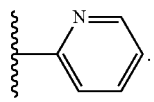

In embodiments, $R^1$ is

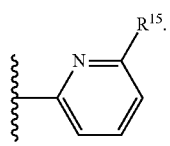

In embodiments, $R^1$ is

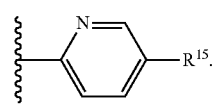

In embodiments, $R^1$ is

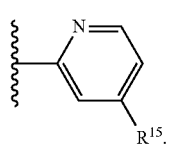

In embodiments, $R^1$ is

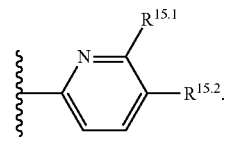

In embodiments, $R^1$ is

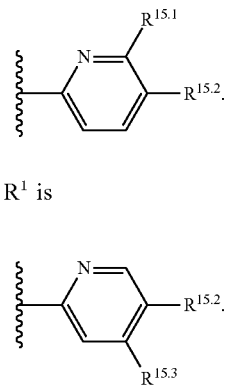

In embodiments, $R^1$ is

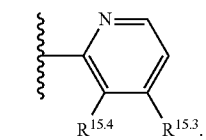

In embodiments, $R^1$ is

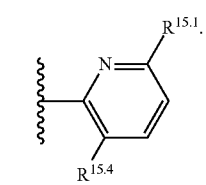

In embodiments, $R^1$ is

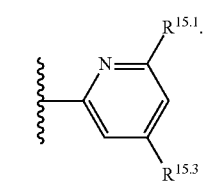

In embodiments, $R^1$ is

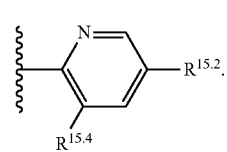

In embodiments, $R^1$ is

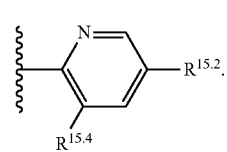

In embodiments, $R^1$ is

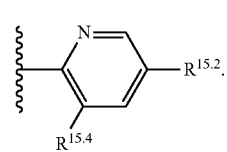

In embodiments, R¹ is
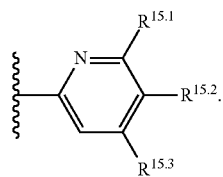
In embodiments, R¹ is
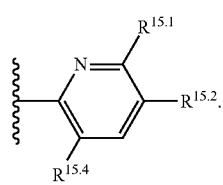
In embodiments, R¹ is
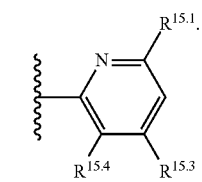
In embodiments, R¹ is
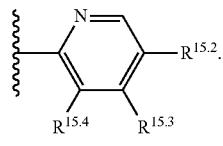
In embodiments, R¹ is
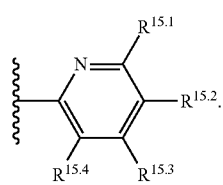
In embodiments, R¹ is
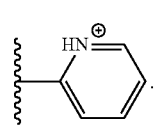
In embodiments, R¹ is
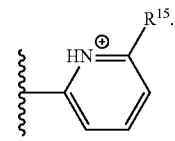
In embodiments R¹ is
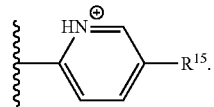
In embodiments, R¹ is
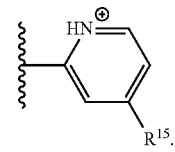
In embodiments, R¹ is
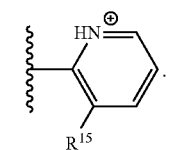
In embodiments, R¹ is
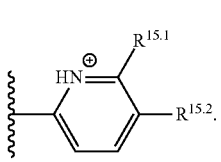
In embodiments, R¹ is
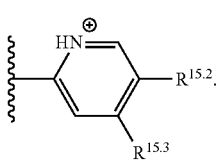
In embodiments, R¹ is
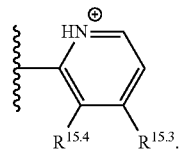

In embodiments, $R^1$ is

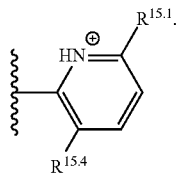

In embodiments, $R^1$ is

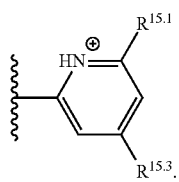

In embodiments, $R^1$ is

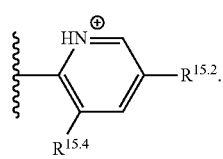

In embodiments, $R^1$ is

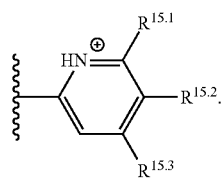

In embodiments, $R^1$ is

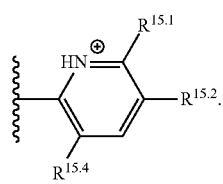

In embodiments, $R^1$ is

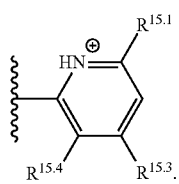

In embodiments, $R^1$ is

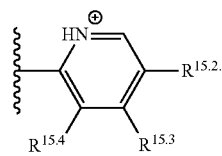

In embodiments, $R^1$ is

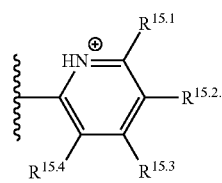

$R^{15.1}$, $R^{15.2}$, $R^{15.3}$, and $R^{15.4}$ each independently has a value of $R^{15}$.

In embodiments, $R^{15.1}$ is independently halogen, —$CX^{15.1}_3$, —$CHX^{15.1}_2$, —$CH_2X^{15.1}$, —CN, —$NHNH_2$, —$NO_2$, —$NH_2$, —C(O)H, —C(O)OH, —C(O)$NH_2$, —OH, —NHC(O)OH, —$OCX^{15.1}_3$, —$OCHX^{15.1}_2$, —$OCH_2X^{15.1}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{15.1}$ is independently a halogen, —$CX^{15.1}_3$, —$CHX^{15.1}_2$, —$CH_2X^{15.1}$, —CN, —$NH_2$, —OH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{15.1}$ is independently a halogen, —$CX^{15.1}_3$, —$CHX^{15.1}_2$, —$CH_2X^{15.1}$, —CN, —$NH_2$, —OH, unsubstituted $C_1$-$C_4$ alkyl, or unsubstituted 2 to 4 membered heteroalkyl. In embodiments, $R^{15.1}$ is independently a halogen, —$CF_3$, unsubstituted methyl, unsubstituted ethyl, unsubstituted isopropyl, unsubstituted methoxy, or unsubstituted ethoxy. In embodiments, $R^{15.1}$ is independently unsubstituted methyl. $X^{15.1}$ is independently halogen (F, Cl, Br, and/or I).

In embodiments, $R^{15.2}$ is independently halogen, —$CX^{15.2}_3$, —$CHX^{15.2}_2$, —$CH_2X^{15.2}$, —CN, —$NHNH_2$, —$NO_2$, —$NH_2$, —C(O)H, —C(O)OH, —C(O)$NH_2$, —OH, —NHC(O)OH, —$OCX^{15.2}_3$, —$OCHX^{15.2}_2$, —$OCH_2X^{15.2}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{15.2}$ is independently a halogen, —$CX^{15.2}_3$, —$CHX^{15.2}_2$, —$CH_2X^{15.2}$, —CN, —$NH_2$, —OH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{15.2}$ is independently a halogen, —$CX^{15.2}_3$, —$CHX^{15.2}_2$, —$CH_2X^{15.2}$, —CN, —$NH_2$, —OH, unsubstituted $C_1$-$C_4$ alkyl, or unsubstituted 2 to 4 membered heteroalkyl. In embodiments, $R^{15.2}$ is independently a halogen, —$CF_3$, unsubstituted methyl, unsubstituted ethyl, unsubstituted isopropyl, unsubstituted methoxy, or unsubstituted ethoxy. In embodiments, $R^{15.2}$ is independently unsubstituted methyl. $X^{15.2}$ is independently halogen (F, Cl, Br, and/or I).

In embodiments, $R^{15.3}$ is independently halogen, —$CX^{15.3}_3$, —$CHX^{15.3}_2$, —$CH_2X^{15.3}$, —CN, —$NHNH_2$, —$NO_2$, —$NH_2$, —C(O)H, —C(O)OH, —C(O)$NH_2$, —OH, —NHC(O)OH, —$OCX^{15.3}_3$, —$OCHX^{15.3}_2$, —$OCH_2X^{15.3}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{15.3}$ is independently a halogen, —$CX^{15.3}_3$, —$CHX^{15.3}_2$, —$CH_2X^{15.3}$, —CN, —$NH_2$, —OH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{15.3}$ is independently a halogen, —$CX^{15.3}_3$, —$CHX^{15.3}_2$, —$CH_2X^{15.3}$, —CN, —$NH_2$, —OH, unsubstituted $C_1$-$C_4$ alkyl, or unsubstituted 2 to 4 membered heteroalkyl. In embodiments, $R^{15.3}$ is independently a halogen, —$CF_3$, unsubstituted methyl, unsubstituted ethyl, unsubstituted isopropyl, unsubstituted methoxy, or unsubstituted ethoxy. In embodiments, $R^{15.3}$ is independently unsubstituted methyl. $X^{15.3}$ is independently halogen (F, Cl, Br, and/or I).

In embodiments, $R^{15.4}$ is independently halogen, —$CX^{15.4}_3$, —$CHX^{15.4}_2$, —$CH_2X^{15.4}$, —CN, —$NHNH_2$, —$NO_2$, —$NH_2$, —C(O)H, —C(O)OH, —C(O)$NH_2$, —OH, —NHC(O)OH, —$OCX^{15.4}_3$, —$OCHX^{15.4}_2$, —$OCH_2X^{15.4}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{15.4}$ is independently a halogen, —$CX^{15.4}_3$, —$CHX^{15.4}_2$, —$CH_2X^{15.4}$, —CN, —$NH_2$, —OH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{15.4}$ is independently a halogen, —$CX^{15.4}_3$, —$CHX^{15.4}_2$, —$CH_2X^{15.4}$, —CN, —$NH_2$, —OH, unsubstituted $C_1$-$C_4$ alkyl, or unsubstituted 2 to 4 membered heteroalkyl. In embodiments, $R^{15.4}$ is independently a halogen, —$CF_3$, unsubstituted methyl, unsubstituted ethyl, unsubstituted isopropyl, unsubstituted methoxy, or unsubstituted ethoxy. In embodiments, $R^{15.4}$ is independently unsubstituted methyl. $X^{15.4}$ is independently halogen (F, Cl, Br, and/or I).

In embodiments, $R^1$ is a substituted or unsubstituted pyrid-2-yl wherein the pyrid-2-yl ring nitrogen is protonated and positively charged. In embodiments, a compound wherein the pyrid-2-yl ring nitrogen is protonated exists as a pharmaceutically acceptable salt (e.g., bis-isethionate, dichloride, pamoate, or di-tosylate). The terms "pyrid-2-yl" and "pyridin-2-yl" are used interchangeably and have their commonly understood meaning within chemistry of a six-membered aromatic ring having five ring carbons and one ring nitrogen, wherein the ring is bonded to another moiety at a ring carbon adjacent to the ring nitrogen.

In embodiments, $R^2$ is independently a hydrogen, halogen, —$CX^2_3$, —$CHX^2_2$, —$CH_2X^2$, —CN, —$NO_2$, —$NH_2$, —OH, —$OCX^2_3$, —$OCHX^2_2$, —$OCH_2X^2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^2$ is independently a hydrogen, halogen, —$CX^2_3$, —$CHX^2_2$, —$CH_2X^2$, —$OCX^2_3$, —$OCHX^2_2$, —$OCH_2X^2$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently a hydrogen, halogen, —$CF_3$, unsubstituted $C_1$-$C_4$ alkyl, or unsubstituted 2 to 4 membered heteroalkyl. In embodiments, $R^2$ is independently a halogen, —$CF_3$, unsubstituted methyl, unsubstituted ethyl, unsubstituted isopropyl, unsubstituted methoxy, or unsubstituted ethoxy. In embodiments, $R^2$ is independently a halogen. In embodiments, $R^2$ is independently —$CF_3$. In embodiments, $R^2$ is independently unsubstituted methyl. In embodiments, $R^2$ is independently unsubstituted ethyl. In embodiments, $R^2$ is independently unsubstituted isopropyl. In embodiments, $R^2$ is independently unsubstituted methoxy. In embodiments, $R^2$ is independently unsubstituted ethoxy. In embodiments, $R^2$ is independently a hydrogen.

In embodiments, $R^2$ is independently halogen. In embodiments, $R^2$ is —F. In embodiments, $R^2$ is —Cl. In embodiments, $R^2$ is —Br. In embodiments, $R^2$ is —I. In embodiments, $R^2$ is —$CX^2_3$. In embodiments, $R^2$ is —$CHX^2_2$. In embodiments, $R^2$ is —$CH_2X^2$. In embodiments, $R^2$ is —CN. In embodiments, $R^2$ is —$NO_2$. In embodiments, $R^2$ is —$NH_2$. In embodiments, $R^2$ is —OH. In embodiments, $R^2$ is —$OCX^2_3$. In embodiments, $R^2$ is —$OCHX^2_2$. In embodiments, $R^2$ is —$OCH_2X^2$. In embodiments, $R^2$ is substituted or unsubstituted $C_1$-$C_8$ alkyl. In embodiments, $R^2$ is substituted or unsubstituted 2 to 8 membered heteroalkyl. In embodiments, $R^2$ is substituted or unsubstituted $C_3$-$C_8$ cycloalkyl. In embodiments, $R^2$ is substituted or unsubstituted 3 to 8 membered heterocycloalkyl. In embodiments, $R^2$ is substituted or unsubstituted $C_6$-$C_{10}$ aryl. In embodiments, $R^2$ is substituted or unsubstituted 5 to 10 membered heteroaryl. In embodiments, $R^2$ is substituted or unsubstituted $C_1$-$C_4$ alkyl. In embodiments, $R^2$ is substituted or unsubstituted 2 to 4 membered heteroalkyl. In embodiments, $R^2$ is substituted or unsubstituted $C_3$-$C_6$ cycloalkyl. In embodiments, $R^2$ is substituted or unsubstituted 3 to 6 membered heterocycloalkyl. In embodiments, $R^2$ is substituted or unsubstituted phenyl. In embodiments, $R^2$ is substituted or unsubstituted 5 to 6 membered heteroaryl. In embodiments, $X^2$ is —F. In embodiments, $X^2$ is —Cl. In embodiments, $X^2$ is —Br. In embodiments, $X^2$ is —I. In embodiments, $R^2$ is substituted $C_1$-$C_8$ alkyl. In embodiments, $R^2$ is substituted 2 to 8 membered heteroalkyl. In embodiments, $R^2$ is substituted $C_3$-$C_8$ cycloalkyl. In embodiments, $R^2$ is substituted 3 to 8 membered heterocycloalkyl. In embodiments, $R^2$ is substituted $C_6$-$C_{10}$ aryl. In embodiments, $R^2$ is substituted 5 to 10 membered heteroaryl. In embodiments, $R^2$ is substituted $C_1$-$C_4$ alkyl. In embodiments, $R^2$ is substituted 2 to 4 membered heteroalkyl. In embodiments, $R^2$ is substituted $C_3$-$C_6$ cycloalkyl. In embodiments, $R^2$ is substituted 3 to 6 membered heterocycloalkyl. In embodiments, $R^2$ is substituted phenyl. In embodiments, $R^2$ is substituted 5 to 6 membered heteroaryl.

In embodiments, $R^2$ is unsubstituted $C_1$-$C_8$ alkyl. In embodiments, $R^2$ is unsubstituted 2 to 8 membered heteroalkyl. In embodiments, $R^2$ is unsubstituted $C_3$-$C_8$ cycloalkyl. In embodiments, $R^2$ is unsubstituted 3 to 8 membered heterocycloalkyl. In embodiments, $R^2$ is unsubstituted $C_6$-$C_{10}$ aryl. In embodiments, $R^2$ is unsubstituted 5 to 10 membered heteroaryl. In embodiments, $R^2$ is unsubstituted $C_1$-$C_4$ alkyl. In embodiments, $R^2$ is unsubstituted 2 to 4 membered heteroalkyl. In embodiments, $R^2$ is unsubstituted $C_3$-$C_6$ cycloalkyl. In embodiments, $R^2$ is unsubstituted 3 to 6 membered heterocycloalkyl. In embodiments, $R^2$ is unsubstituted phenyl. In embodiments, $R^2$ is unsubstituted 5 to 6 membered heteroaryl.

In embodiments, $R^3$ is independently a hydrogen, halogen, —$CX^3{}_3$, —$CHX^3{}_2$, —$CH_2X^3$, —CN, —$NO_2$, —$NH_2$, —OH, —$OCX^3{}_3$, —$OCHX^3{}_2$, —$OCH_2X^3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^3$ is independently a hydrogen, halogen, —$CX^3{}_3$, —$CHX^3{}_2$, —$CH_2X^3$, —$OCX^3{}_3$, —$OCHX^3{}_2$, $OCH_2X^3$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently a hydrogen, halogen, —$CF_3$, unsubstituted $C_1$-$C_4$ alkyl, or unsubstituted 2 to 4 membered heteroalkyl. In embodiments, $R^3$ is independently a halogen, —$CF_3$, unsubstituted methyl, unsubstituted ethyl, unsubstituted isopropyl, unsubstituted methoxy, or unsubstituted ethoxy. In embodiments, $R^3$ is independently a halogen. In embodiments, $R^3$ is —$CF_3$. In embodiments, $R^3$ is unsubstituted methyl. In embodiments, $R^3$ is unsubstituted ethyl. In embodiments, $R^3$ is unsubstituted isopropyl. In embodiments, $R^3$ is unsubstituted methoxy. In embodiments, $R^3$ is unsubstituted ethoxy. In embodiments, $R^3$ is independently a hydrogen.

In embodiments, $R^3$ is independently halogen. In embodiments, $R^3$ is —F. In embodiments, $R^3$ is —Cl. In embodiments, $R^3$ is —Br. In embodiments, $R^3$ is —I. In embodiments, $R^3$ is —$CX^3{}_3$. In embodiments, $R^3$ is —$CHX^3{}_2$. In embodiments, $R^3$ is —$CH_2X^3$. In embodiments, $R^3$ is —CN. In embodiments, $R^3$ is —$NO_2$. In embodiments, $R^3$ is —$NH_2$. In embodiments, $R^3$ is —OH. In embodiments, $R^3$ is —$OCX^3{}_3$. In embodiments, $R^3$ is —$OCHX^3{}_2$. In embodiments, $R^3$ is —$OCH_2X^3$. In embodiments, $R^3$ is substituted or unsubstituted $C_1$-$C_8$ alkyl. In embodiments, $R^3$ is substituted or unsubstituted 2 to 8 membered heteroalkyl. In embodiments, $R^3$ is substituted or unsubstituted $C_3$-$C_8$ cycloalkyl. In embodiments, $R^3$ is substituted or unsubstituted 3 to 8 membered heterocycloalkyl. In embodiments, $R^3$ is substituted or unsubstituted $C_6$-$C_{10}$ aryl. In embodiments, $R^3$ is substituted or unsubstituted 5 to 10 membered heteroaryl. In embodiments, $R^3$ is substituted or unsubstituted $C_1$-$C_4$ alkyl. In embodiments, $R^3$ is substituted or unsubstituted 2 to 4 membered heteroalkyl. In embodiments, $R^3$ is substituted or unsubstituted $C_3$-$C_6$ cycloalkyl. In embodiments, $R^3$ is substituted or unsubstituted 3 to 6 membered heterocycloalkyl. In embodiments, $R^3$ is substituted or unsubstituted phenyl. In embodiments, $R^3$ is substituted or unsubstituted 5 to 6 membered heteroaryl. In embodiments, $X^3$ is —F. In embodiments, $X^3$ is —Cl. In embodiments, $X^3$ is —Br. In embodiments, $X^3$ is —I. In embodiments, $R^3$ is substituted $C_1$-$C_8$ alkyl. In embodiments, $R^3$ is substituted 2 to 8 membered heteroalkyl. In embodiments, $R^3$ is substituted $C_3$-$C_8$ cycloalkyl. In embodiments, $R^3$ is substituted 3 to 8 membered heterocycloalkyl. In embodiments, $R^3$ is substituted $C_6$-$C_{10}$ aryl. In embodiments, $R^3$ is substituted 5 to 10 membered heteroaryl. In embodiments, $R^3$ is substituted $C_1$-$C_4$ alkyl. In embodiments, $R^3$ is substituted 2 to 4 membered heteroalkyl. In embodiments, $R^3$ is substituted $C_3$-$C_6$ cycloalkyl. In embodiments, $R^3$ is substituted 3 to 6 membered heterocycloalkyl. In embodiments, $R^3$ is substituted phenyl. In embodiments, $R^3$ is substituted 5 to 6 membered heteroaryl. In embodiments, $R^3$ is unsubstituted $C_1$-$C_8$ alkyl. In embodiments, $R^3$ is unsubstituted 2 to 8 membered heteroalkyl. In embodiments, $R^3$ is unsubstituted $C_3$-$C_8$ cycloalkyl. In embodiments, $R^3$ is unsubstituted 3 to 8 membered heterocycloalkyl. In embodiments, $R^3$ is unsubstituted $C_6$-$C_{10}$ aryl. In embodiments, $R^3$ is unsubstituted 5 to 10 membered heteroaryl. In embodiments, $R^3$ is unsubstituted $C_1$-$C_4$ alkyl. In embodiments, $R^3$ is unsubstituted 2 to 4 membered heteroalkyl. In embodiments, $R^3$ is unsubstituted $C_3$-$C_6$ cycloalkyl. In embodiments, $R^3$ is unsubstituted 3 to 6 membered heterocycloalkyl. In embodiments, $R^3$ is unsubstituted phenyl. In embodiments, $R^3$ is unsubstituted 5 to 6 membered heteroaryl.

In embodiments, $R^4$ is independently hydrogen, —$CF_3$, or substituted or unsubstituted $C_1$-$C_4$ alkyl. In embodiments, $R^4$ is independently hydrogen, —$CF_3$, unsubstituted methyl, unsubstituted ethyl, or unsubstituted isopropyl. In embodiments, $R^4$ is independently hydrogen. In embodiments, $R^4$ is —$CF_3$. In embodiments, $R^4$ is unsubstituted methyl. In embodiments, $R^4$ is unsubstituted ethyl. In embodiments, $R^4$ is or unsubstituted isopropyl. In embodiments, $R^4$ is substituted or unsubstituted $C_1$-$C_4$ alkyl. In embodiments, $R^4$ is unsubstituted $C_1$-$C_4$ alkyl.

In embodiments, $R^5$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^5$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is a hydrogen. In embodiments, $R^5$ is an unsubstituted $C_1$-$C_4$ alkyl. In embodiments, $R^5$ is an unsubstituted methyl or unsubstituted ethyl. In embodiments, $R^5$ is an unsubstituted methyl. In embodiments, $R^5$ is an unsubstituted ethyl. In embodiments, $R^5$ is a hydrogen. In embodiments, $R^5$ is substituted or unsubstituted $C_1$-$C_4$ alkyl. In embodiments, $R^5$ is unsubstituted $C_1$-$C_4$ alkyl.

In embodiments, $R^6$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^6$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^6$ is a hydrogen. In embodiments, $R^6$ is unsubstituted $C_1$-$C_4$ alkyl. In embodiments, $R^6$ is an unsubstituted methyl or unsubstituted ethyl. In embodiments, $R^6$ is an unsubstituted methyl. In embodiments, $R^6$ is an unsubstituted ethyl. In embodiments, $R^6$ is a hydrogen. In embodiments, $R^6$ is substituted or unsubstituted $C_1$-$C_4$ alkyl. In embodiments, $R^6$ is unsubstituted $C_1$-$C_4$ alkyl.

In embodiments, $L^1$ is independently a bond, substituted or unsubstituted alkylene, substituted or unsubstituted alkenylene, substituted or unsubstituted heteroalkylene, or substituted or unsubstituted heteroalkenylene. In embodiments, $L^1$ is independently a bond, substituted or unsubstituted $C_1$-$C_4$ alkylene, substituted or unsubstituted $C_2$-$C_4$ alkenylene, substituted or unsubstituted 2 to 4 membered heteroalkylene, or substituted or unsubstituted 3 to 4 membered heteroalkenylene. In embodiments, $L^1$ is independently a bond, unsubstituted $C_1$-$C_4$ alkylene, unsubstituted $C_2$-$C_4$ alkenylene, unsubstituted 2 to 4 membered heteroalkylene, or unsubstituted 3 to 4 membered heteroalkenylene. In embodiments, $L^1$ is independently an unsubstituted $C_2$-$C_3$ alkylene or unsubstituted $C_2$-$C_3$ alkenylene. In embodiments, $L^1$ is independently an unsubstituted ethylene or unsubstituted ethenylene. In embodiments, $L^1$ is independently an unsubstituted ethylene. In embodiments, $L^1$ is independently an unsubstituted ethenylene. In embodiments, $L^1$ is independently an unsubstituted methylene.

Each $R^7$, $R^8$, $R^9$, $R^{10}$, $R^{11}$, $R^{12}$, $R^{13}$, and $R^{14}$ may independently be hydrogen, halogen, $-CX_3$, $-CHX_2$, $-CH_2X$, $-OCX_3$, $-OCHX_2$, $-OCH_2X$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, halogen, $-CF_3$, $-CHF_2$, $-CH_2F$, $-OCF_3$, $-OCHF_2$, $-OCH_2F$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, halogen, $-CF_3$, $-CHF_2$, $-CH_2F$, $-OCF_3$, $-OCHF_2$, $-OCH_2F$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, halogen, $-CF_3$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, $-CX_3$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, $-CX_3$, $-CN$, $-COOH$, $-CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, $-CX_3$, $-CHX_2$, $-CH_2X$, $-CN$, $-COOH$, $-CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, $-CX_3$, $-CHX_2$, $-CH_2X$, $-CN$, $-COOH$, $-CONH_2$, unsubstituted $C_1$-$C_4$ alkyl, or unsubstituted 2 to 4 membered heteroalkyl. Each $R^7$, $R^8$, $R^9$, $R^{10}$, $R^{11}$, $R^{12}$, $R^{13}$, and $R^{14}$ may independently be hydrogen. Each $R^7$, $R^8$, $R^9$, $R^{10}$, $R^{11}$, $R^{12}$, $R^{13}$, and $R^{14}$ may independently be unsubstituted $C_1$-$C_4$ alkyl. Each $R^7$, $R^8$, $R^9$, $R^{10}$, $R^{11}$, $R^{12}$, $R^{13}$, and $R^{14}$ may independently be unsubstituted methyl.

Each $R^7$ and $R^8$ substituents bonded to the same nitrogen atom may be joined to form a substituted or unsubstituted heterocycloalkyl or substituted or unsubstituted heteroaryl. Each $R^7$ and $R^8$ substituents bonded to the same nitrogen atom may be joined to form an unsubstituted heterocycloalkyl or unsubstituted heteroaryl. Each $R^7$ and $R^8$ substituents bonded to the same nitrogen atom may be joined to form a substituted or unsubstituted 4 to 6 membered heterocycloalkyl or 5 to 6 membered heteroaryl. Each $R^7$ and $R^8$ substituents bonded to the same nitrogen atom may be joined to form an unsubstituted 4 to 6 membered heterocycloalkyl or unsubstituted 5 to 6 membered heteroaryl. Each $R^7$ and $R^8$ substituents bonded to the same nitrogen atom may be joined to form a substituted or unsubstituted heterocycloalkyl. Each $R^7$ and $R^8$ substituents bonded to the same nitrogen atom may be joined to form an unsubstituted heterocycloalkyl. Each $R^7$ and $R^8$ substituents bonded to the same nitrogen atom may be joined to form a substituted or unsubstituted 4 to 6 membered heterocycloalkyl. Each $R^7$ and $R^8$ substituents bonded to the same nitrogen atom may be joined to form an unsubstituted 4 to 6 membered heterocycloalkyl.

Each $R^{11}$ and $R^{12}$ substituents bonded to the same nitrogen atom may be joined to form a substituted or unsubstituted heterocycloalkyl or substituted or unsubstituted heteroaryl. Each $R^{11}$ and $R^{12}$ substituents bonded to the same nitrogen atom may be joined to form an unsubstituted heterocycloalkyl or unsubstituted heteroaryl. Each $R^{11}$ and $R^{12}$ substituents bonded to the same nitrogen atom may be joined to form a substituted or unsubstituted 4 to 6 membered heterocycloalkyl or substituted or unsubstituted 5 to 6 membered heteroaryl. Each $R^{11}$ and $R^{12}$ substituents bonded to the same nitrogen atom may be joined to form an unsubstituted 4 to 6 membered heterocycloalkyl or unsubstituted 5 to 6 membered heteroaryl. Each $R^{11}$ and $R^{12}$ substituents bonded to the same nitrogen atom may be joined to form a substituted or unsubstituted heterocycloalkyl. Each $R^{11}$ and $R^{12}$ substituents bonded to the same nitrogen atom may be joined to form an unsubstituted heterocycloalkyl. Each $R^{11}$ and $R^{12}$ substituents bonded to the same nitrogen atom may be joined to form a substituted or unsubstituted 4 to 6 membered heterocycloalkyl. Each $R^{11}$ and $R^{12}$ substituents bonded to the same nitrogen atom may be joined to form an unsubstituted 4 to 6 membered heterocycloalkyl.

Each $R^{16}$, $R^{17}$, $R^{18}$, and $R^{19}$ may independently be hydrogen, halogen, —$CX_3$, —$CHX_2$, —$CH_2X$, —$OCX_3$, —$OCHX_2$, —$OCH_2X$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{16}$, $R^{17}$, $R^{18}$, and $R^{19}$ may independently be hydrogen, halogen, —$CF_3$, —$CHF_2$, —$CH_2F$, —$OCF_3$, —$OCHF_2$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{16}$, $R^{17}$, $R^{18}$, and $R^{19}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{16}$, $R^{17}$, $R^{18}$, and $R^{19}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^{16}$, $R^{17}$, $R^{18}$, and $R^{19}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^{16}$, $R^{17}$, $R^{18}$, and $R^{19}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. Each $R^{16}$, $R^{17}$, $R^{18}$, and $R^{19}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^{16}$, $R^{17}$, $R^{18}$, and $R^{19}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. Each $R^{16}$, $R^{17}$, $R^{18}$, and $R^{19}$ may independently be hydrogen, —$CX_3$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{16}$, $R^{17}$, $R^{18}$, and $R^{19}$ may independently be hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^{16}$, $R^{17}$, $R^{18}$, and $R^{19}$ may independently be hydrogen, —$CX_3$, —$CHX_2$, —$CH_2X$, —CN, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. Each $R^{16}$, $R^{17}$, $R^{18}$, and $R^{19}$ may independently be hydrogen, —$CX_3$, —$CHX_2$, —$CH_2X$, —CN, —COOH, —$CONH_2$, unsubstituted $C_1$-$C_4$ alkyl, or unsubstituted 2 to 4 membered heteroalkyl. Each $R^{16}$, $R^{17}$, $R^{18}$, and $R^{19}$ may independently be hydrogen. Each $R^{16}$, $R^{17}$, $R^{18}$, and $R^{19}$ may independently be unsubstituted $C_1$-$C_4$ alkyl. Each $R^{16}$, $R^{17}$, $R^{18}$, and $R^{19}$ may independently be unsubstituted methyl.

Each $R^{16}$ and $R^{17}$ substituents bonded to the same nitrogen atom may be joined to form a substituted or unsubstituted heterocycloalkyl or substituted or unsubstituted heteroaryl. Each $R^{16}$ and $R^{17}$ substituents bonded to the same nitrogen atom may be joined to form an unsubstituted heterocycloalkyl or unsubstituted heteroaryl. Each $R^{16}$ and $R^{17}$ substituents bonded to the same nitrogen atom may be joined to form a substituted or unsubstituted 4 to 6 membered heterocycloalkyl or substituted or unsubstituted 5 to 6 membered heteroaryl. Each $R^{16}$ and $R^{17}$ substituents bonded to the same nitrogen atom may be joined to form an unsubstituted 4 to 6 membered heterocycloalkyl or unsubstituted 5 to 6 membered heteroaryl. Each $R^{16}$ and $R^{17}$ substituents bonded to the same nitrogen atom may be joined to form a substituted or unsubstituted heterocycloalkyl. Each $R^{16}$ and $R^{17}$ substituents bonded to the same nitrogen atom may be joined to form an unsubstituted heterocycloalkyl. Each $R^{16}$ and $R^{17}$ substituents bonded to the same nitrogen atom may be joined to form a substituted or unsubstituted 4 to 6 membered heterocycloalkyl. Each $R^{16}$ and $R^{17}$ substituents bonded to the same nitrogen atom may be joined to form an unsubstituted 4 to 6 membered heterocycloalkyl.

The symbol X may be —Cl. The symbol X may be —Br. The symbol X may be —I. The symbol X may be —F.

The symbol $X^2$ may be —Cl. The symbol $X^2$ may be —Br. The symbol $X^2$ may be —I. The symbol $X^2$ may be —F.

The symbol $X^3$ may be —Cl. The symbol $X^3$ may be —Br. The symbol $X^3$ may be —I. The symbol $X^3$ may be —F.

The symbol $X^4$ may be —Cl. The symbol $X^4$ may be —Br. The symbol $X^4$ may be —I. The symbol $X^4$ may be —F.

The symbol $X^5$ may be —Cl. The symbol $X^5$ may be —Br. The symbol $X^5$ may be —I. The symbol $X^5$ may be —F.

The symbol $X^6$ may be —Cl. The symbol $X^6$ may be —Br. The symbol $X^6$ may be —I. The symbol $X^6$ may be —F.

The symbol $X^{15}$ may be —Cl. The symbol $X^{15}$ may be —Br. The symbol $X^{15}$ may be —I. The symbol $X^{15}$ may be —F.

The symbol m2 may be 1. The symbol m2 may be 2. The symbol m3 may be 1. The symbol m3 may be 2. The symbol m15 may be 1. The symbol m15 may be 2. The symbol v2 may be 1. The symbol v2 may be 2. The symbol v3 may be 1. The symbol v3 may be 2. The symbol v15 may be 1. The symbol v15 may be 2.

The symbol n2 may be 0. The symbol n2 may be 1. The symbol n2 may be 2. The symbol n2 may be 3. The symbol n2 may be 4. The symbol n3 may be 0. The symbol n3 may be 1. The symbol n3 may be 2. The symbol n3 may be 3. The symbol n3 may be 4. The symbol n15 may be 0. The symbol n15 may be 1. The symbol n15 may be 2. The symbol n15 may be 3. The symbol n15 may be 4. The symbol z may be 0. The symbol z may be 1. The symbol z may be 2. The symbol z may be 3. The symbol z may be 4.

In embodiments, the compound is:

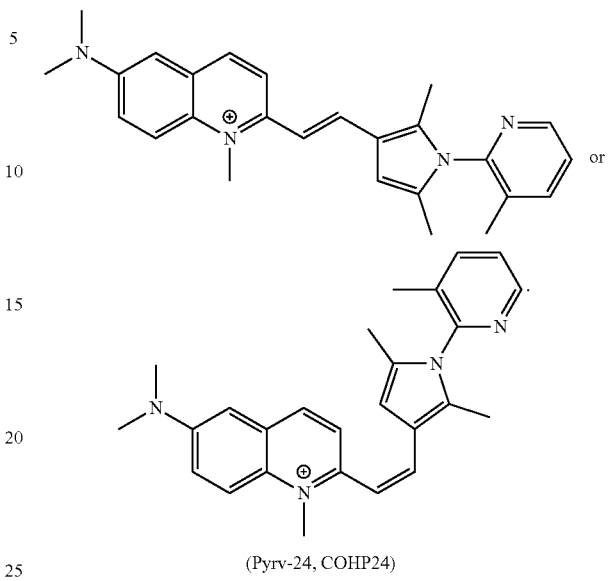

(Pyrv-24, COHP24)

In embodiments, the compound is:

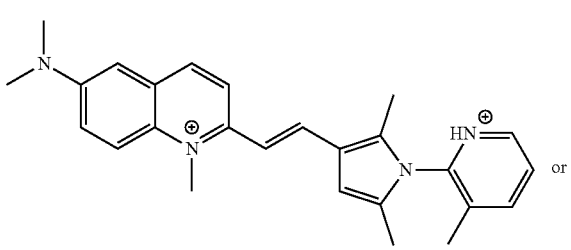

or

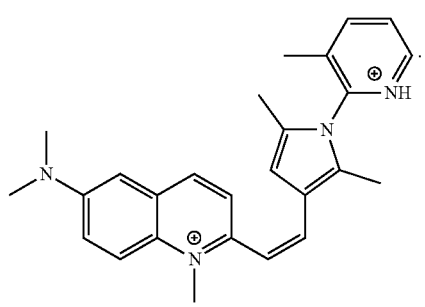

In embodiments, the compound is:

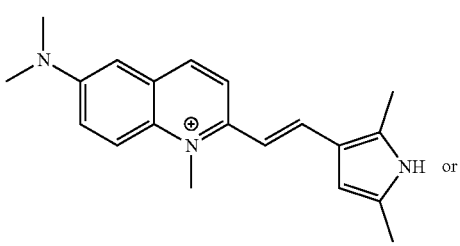

or

-continued

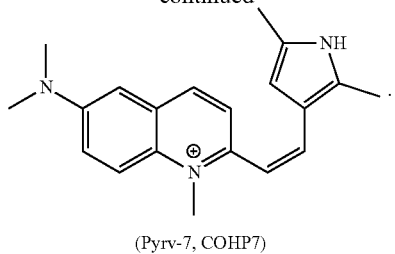

(Pyrv-7, COHP7)

In embodiments, the compound is:

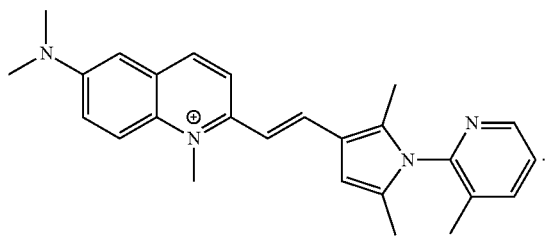 [SMILES: Cc1cccnc1-n1c(C)cc(/C=C/c2ccc3cc(N(C)C)ccc3[n+]2C)c1C]

In embodiments, the compound is:

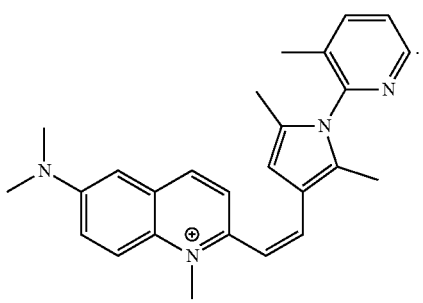 [SMILES: Cc1cccnc1-n1c(C)cc(/C=C\c2ccc3cc(N(C)C)ccc3[n+]2C)c1C]

In embodiments, the compound is:

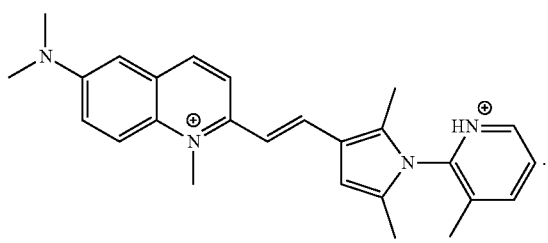 [SMILES: Cc1ccc[nH+]c1-n1c(C)cc(/C=C/c2ccc3cc(N(C)C)ccc3[n+]2C)c1C]

In embodiments, the compound is:

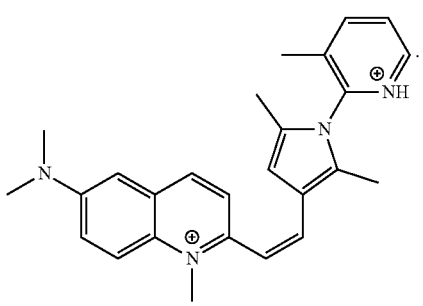 [SMILES: Cc1ccc[nH+]c1-n1c(C)cc(/C=C\c2ccc3cc(N(C)C)ccc3[n+]2C)c1C]

In embodiments, the compound is:

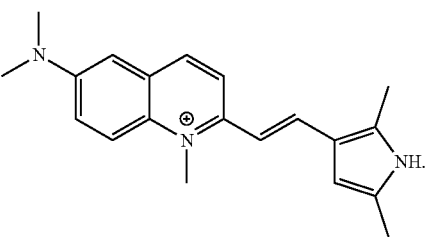 [SMILES: Cc1cc(/C=C/c2ccc3cc(N(C)C)ccc3[n+]2C)c(C)[nH]1]

In embodiments, the compound is:

In embodiments, Pyrv-24, COHP24 refers to the E isomer of the compound. In embodiments, Pyrv-24, COHP24 refers to the Z isomer of the compound. In embodiments, Pyrv-24, COHP24 refers to a mixture of the E and the Z isomers of the compounds.

In embodiments, Pyrv-7, COHP7 refers to the E isomer of the compound. In embodiments, Pyrv-7, COHP7 refers to the Z isomer of the compound. In embodiments, Pyrv-7, COHP7 refers to a mixture of the E and the Z isomers of the compounds.

In embodiments, the compound is an antagonist of a nuclear receptor. In embodiments, the compound is an antagonist of an androgen receptor. In embodiments, the compound is an antagonist of a human androgen receptor. In embodiments, the compound is an antagonist of wildtype human androgen receptor. In embodiments, the compound is an antagonist of a mutant human androgen receptor. In embodiments, the compound is an antagonist of a drug-resistant human androgen receptor. In embodiments, the compound is an antagonist of a casodex-resistant human androgen receptor. In embodiments, the compound is an antagonist of a Flutamide-resistant human androgen receptor. In embodiments, the compound is an antagonist of an MDV3100-resistant human androgen receptor. In embodiments, the compound is an antagonist of an ARN-509-resistant human androgen receptor. In embodiments, the compound is an antagonist of non-ligand activated androgen receptor. In embodiments, the compound is an antagonist of N-terminal activated non-ligand activated androgen receptor. In embodiments, the compound is an antagonist of a non-ligand activated androgen receptor splice variant. In embodiments, the compound is an antagonist of a non-ligand activated androgen receptor activated by HER2. In embodiments, the compound is an antagonist of a non-ligand activated androgen receptor activated by IL-6.

In embodiments, the compound does not inhibit ligand (e.g., DHT) binding to androgen receptor. In embodiments, the compound does not bind the ligand binding domain of androgen receptor. In embodiments, the compound binds the DNA binding domain of androgen receptor. In embodiments, the compound does not increase the degradation of androgen receptor relative to the absence of the compound. In embodiments, the compound does not reduce the nuclear localization of androgen receptor relative to the absence of the compound. In embodiments, the compound does not prevent androgen receptor binding to DNA. In embodiments, the compound does not reduce the binding of androgen receptor to DNA. In embodiments, the compound prevents the recruitment of RNA pol II to DNA. In embodiments, the compound prevents the binding of RNA pol II to the transcription complex including androgen receptor bound to the compound. In embodiments, the compound prevents initiation of transcription by androgen receptor. In embodiments, the compound inhibits (e.g., compared to control) the recruitment of RNA pol II to DNA. In embodiments, the compound inhibits (e.g., compared to control) the binding of RNA pol II to the transcription complex including androgen receptor bound to the compound. In embodiments, the compound inhibits (e.g., compared to control) initiation of transcription by androgen receptor. In embodiments, the compound reduces transcription induced by androgen receptor relative to control (e.g., absence of compound). In embodiments, the compound reduces co-activator binding to androgen receptor. In embodiments, the compound binds androgen receptor and DNA. In embodiments, the compound binds androgen receptor while bound to DNA. In embodiments, the compound binds the minor groove of DNA. In embodiments, the compound contacts one or more of Lys609, Asn610, Pro612, Phe582, Ala586, Tyr593, and/or Arg615. In embodiments, the compound contacts one or more of Lys609, Asn610, and Pro612. In embodiments, the compound contacts the minor groove of DNA. In embodiments, the compound contacts one or more amino acids corresponding to Lys609, Asn610, Pro612, Phe582, Ala586, Tyr593, and/or Arg615 of human androgen receptor. In embodiments, the compound contacts one or more amino acids corresponding to Lys609, Asn610, and/or Pro612 of human androgen receptor. In embodiments, the compound contacts amino acids corresponding to Lys609 and Pro612 of human androgen receptor. In embodiments, the compound contacts amino acids corresponding to Lys609 and Pro612 but not Asn610 of human androgen receptor. In embodiments, the compound contacts amino acids corresponding to Lys609 or Pro612 but not Asn610 of human androgen receptor. In embodiments, the compound contacts amino acids corresponding to Lys609 or Pro612 of human androgen receptor. In embodiments, the compound contacts amino acids Lys609 or Pro612 of human androgen receptor. In embodiments, the compound contacts amino acids Lys609 and Pro612 of human androgen receptor. In embodiments, the compound contacts amino acids Lys609 and Pro612 but not Asn610 of human androgen receptor. In embodiments, the compound contacts amino acids Lys609 or Pro612 and not Asn610 of human androgen receptor. In embodiments, reference to amino acid numbering of Androgen Receptor Lys609, Asn610, Pro612, Phe582, Ala586, Tyr593, and Arg615 in this paragraph are within the protein sequence of the Androgen Receptor included in the definition of Androgen Receptor herein above having SEQ ID NO:1. In embodiments, reference to amino acid numbering of Androgen Receptor Lys609, Asn610, Pro612, Phe582, Ala586, Tyr593, and Arg615 in this paragraph refer to amino acids corresponding to the residues having those amino acid primary sequence numbers within the protein sequence of the Androgen Receptor included in the definition of Androgen Receptor herein above having SEQ ID NO:1.

In embodiments, the compound contacts one or more of the nucleobases of an androgen response element, corresponding to A11, A12, G13, T26, G27, A28, and/or T29 of the sequence: 5'-(1) CCAGAACATCAAGAACAG (18)-3' (SEQ ID NO:3) bound to the complementary sequence 5'-(19) CTGTTCTTGATGTTCTGG (36)-3' (SEQ ID NO:4). In embodiments, the compound contacts one or more of the nucleobases of an androgen response element, corresponding to the unpaired loop nucleobases between the two complementary sequences of an androgen response element. A person of ordinary skill will readily recognize that the sequence above is one example of an androgen response element and well known examples of other androgen response elements may readily be identified and the nucleobases in such other sequences that correspond to the nucleobases identified in the sequence above that bind to a compound described herein, may be identified. Such sequences are incorporated herein by reference.

In embodiments, the compound inhibits (e.g. compared to control) androgen receptor activity in prostate and/or bone to a greater degree than other tissues.

In embodiments, the compound is soluble in an aqueous solution. In embodiments, the compound is soluble in a dextrin (e.g., hydroxypropyl beta and gamma)

It will be understood that a pharmaceutically acceptable salt of the compounds described herein includes a counterion. In embodiments, the counterion may be pamoate. In embodiments, the counterion may be an anion of a pharmaceutically acceptable salt as described herein. In embodiments, the counterion may be chloride.

In embodiments, $R^1$ is independently hydrogen or $R^{15}$-substituted or unsubstituted pyrid-2-yl. In embodiments, $R^1$ is independently hydrogen. In embodiments, $R^1$ is independently $R^{15}$-substituted or unsubstituted pyrid-2-yl. In embodiments, $R^1$ is independently unsubstituted pyrid-2-yl. In embodiments, $R^1$ is independently $R^{15}$-substituted pyrid-2-yl.

In embodiments, $R^2$ is independently hydrogen, oxo, halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered). $X^2$ is independently $-F$, $-Cl$, $-Br$, or $-I$. In embodiments, $X^2$ is $-F$. In embodiments, $R^2$ is independently hydrogen. In embodiments, $R^2$ is independently unsubstituted methyl. In embodiments, $R^2$ is independently unsubstituted ethyl. In embodiments, $R^2$ is independently hydrogen, oxo, halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, 2 to 3 membered, or 4 to 5 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 6 membered, 4 to 6 membered, 4 to 5 membered, or 5 to 6 membered), $R^{34}$-substituted or unsubstituted aryl (e.g., $C_6$-$C_{10}$ or phenyl), or $R^{34}$-substituted or unsubstituted heteroaryl (e.g., 5 to 10 membered, 5 to 9 membered, or 5 to 6 membered). $X^{33}$ is independently —F, —Cl, —Br, or —I. In embodiments, $X^{33}$ is —F. In embodiments, $R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{34}$ is independently oxo, halogen, —$CX^{34}_3$, —$CHX^{34}_2$, —$CH_2X^{34}$, —$OCX^{34}_3$, —$OCH_2X^{34}$, —$OCHX^{34}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{35}$-substituted or unsubstituted alkyl (e.g., $C_1$-$C_8$, $C_1$-$C_6$, $C_1$-$C_4$, or $C_1$-$C_2$), $R^{35}$-substituted or unsubstituted heteroalkyl (e.g., 2 to 8 membered, 2 to 6 membered, 4 to 6 membered, 2 to 3 membered, or 4 to 5 membered), $R^{35}$-substituted or unsubstituted cycloalkyl (e.g., $C_3$-$C_8$, $C_3$-$C_6$, $C_4$-$C_6$, or $C_5$-$C_6$), $R^{35}$-substituted or unsubstituted heterocycloalkyl (e.g., 3 to 6 membered, 4 to 6 membered, 4 to 5 membered, or 5 to 6 membered), $R^{35}$-substituted or unsubstituted aryl (e.g., $C_6$-$C_{10}$ or phenyl), or $R^{35}$-substituted or unsubstituted heteroaryl (e.g., 5 to 10 membered, 5 to 9 membered, or 5 to 6 membered). $X^{34}$ is independently —F, —Cl, —Br, or —I. In embodiments, $X^{34}$ is —F. In embodiments, $R^{34}$ is independently oxo, halogen, —$CX^{34}_3$, —$CHX^{34}_2$, —$CH_2X^{34}$, —$OCX^{34}_3$, —$OCH_2X^{34}$, —$OCHX^{34}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{35}$ is independently oxo, halogen, —$CX^{35}_3$, —$CHX^{35}_2$, —$CH_2X^{35}$, —$OCX^{35}_3$, —$OCH_2X^{35}$, —$OCHX^{35}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC—(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{35}$ is independently —F, —Cl, —Br, or —I. In embodiments, $X^{35}$ is —F.

In embodiments, $R^3$ is independently hydrogen, oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered). $X^3$ is independently —F, —Cl, —Br, or —I. In embodiments, $X^3$ is —F. In embodiments, $R^3$ is independently hydrogen. In embodiments, $R^3$ is independently unsubstituted methyl. In embodiments, $R^3$ is independently unsubstituted ethyl. In embodiments, $R^3$ is independently hydrogen, oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{36}$ is independently oxo, halogen, —$CX^{36}_3$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, 2 to 3 membered, or 4 to 5 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 6 membered, 4 to 6 membered, 4 to 5 membered, or 5 to 6 membered), $R^{37}$-substituted or unsubstituted aryl (e.g., $C_6$-$C_{10}$ or phenyl), or $R^{37}$-substituted or unsubstituted heteroaryl (e.g., 5 to 10 membered, 5 to 9 membered, or 5 to 6 membered). $X^{36}$ is independently —F, —Cl, —Br, or —I. In embodiments, $X^{36}$ is —F. In embodiments, $R^{36}$ is independently oxo, halogen, —$CX^{36}_3$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{37}$ is independently oxo, halogen, —$CX^{37}_3$, —$CHX^{37}_2$, —$CH_2X^{37}$, —$OCX^{37}_3$, —$OCH_2X^{37}$, —$OCHX^{37}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{38}$-substituted or unsubstituted alkyl (e.g., $C_1$-$C_8$, $C_1$-$C_6$, $C_1$-$C_4$, or $C_1$-$C_2$), $R^{38}$-substituted or unsubstituted heteroalkyl (e.g., 2 to 8 membered, 2 to 6 membered, 4 to 6 membered, 2 to 3 membered, or 4 to 5 membered), $R^{38}$-substituted or unsubstituted cycloalkyl (e.g., $C_3$-$C_8$, $C_3$-$C_6$, $C_4$-$C_6$, or $C_5$-$C_6$), $R^{38}$-substituted or unsubstituted heterocycloalkyl (e.g., 3 to 6 membered, 4 to 6 membered, 4 to 5 membered, or 5 to 6 membered), $R^{38}$-substituted or unsubstituted aryl (e.g., $C_6$-$C_{10}$ or phenyl), or $R^{38}$-substituted or unsubstituted heteroaryl (e.g., 5 to 10 membered, 5 to 9 membered, or 5 to 6 membered). $X^{37}$ is independently —F, —Cl, —Br, or —I. In embodiments, $X^{37}$ is —F. In embodiments, $R^{37}$ is independently oxo, halogen, —$CX^{37}_3$, —$CHX^{37}_2$, —$CH_2X^{37}$, —$OCX^{37}_3$, —$OCH_2X^{37}$, —$OCHX^{37}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{38}$ is independently oxo, halogen, —$CX^{38}_3$, —$CHX^{38}_2$, —$CH_2X^{38}$, —$OCX^{38}_3$, —$OCH_2X^{38}$, —$OCHX^{38}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38}$ is independently —F, —Cl, —Br, or —I. In embodiments, $X^{38}$ is —F.

In embodiments, $R^4$ is independently hydrogen, oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). $X^4$ is independently —F, —Cl, —Br, or —I. In embodiments, $X^4$ is —F. In embodiments, $R^4$ is independently hydrogen. In embodiments, $R^4$ is independently unsubstituted methyl. In embodiments, $R^4$ is independently unsubstituted ethyl. In embodiments, $R^4$ is independently hydrogen, oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{39}$ is independently oxo, halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered). $X^{39}$ is independently —F, —Cl, —Br, or —I. In embodiments, $X^{39}$ is —F. In embodiments, $R^{39}$ is independently oxo, halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 6 membered, 4 to 6 membered, 4 to 5 membered, or 5 to 6 membered), $R^{41}$-substituted or unsubstituted aryl (e.g., $C_6$-$C_{10}$ or phenyl), or $R^{41}$-substituted or unsubstituted heteroaryl (e.g., 5 to 10 membered, 5 to 9 membered, or 5 to 6 membered). $X^{40}$ is independently —F, —Cl, —Br, or —I. In embodiments, $X^{40}$ is —F. In embodiments, $R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41}$ is independently —F, —Cl, —Br, or —I. In embodiments, $X^{41}$ is —F.

In embodiments, $R^5$ is independently hydrogen, oxo, halogen, —$CX^5_3$, —$CHX^5_2$, —$CH_2X^5$, —$OCX^5_3$, —$OCH_2X^5$, —$OCHX^5_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{42}$-substituted or unsubstituted alkyl (e.g., $C_1$-$C_8$, $C_1$-$C_6$, $C_1$-$C_4$, or $C_1$-$C_2$), $R^{42}$-substituted or unsubstituted heteroalkyl (e.g., 2 to 8 membered, 2 to 6 membered, 4 to 6 membered, 2 to 3 membered, or 4 to 5 membered), $R^{42}$-substituted or unsubstituted cycloalkyl (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 6 membered, 4 to 6 membered, 4 to 5 membered, or 5 to 6 membered), $R^{42}$-substituted or unsubstituted aryl (e.g., $C_6$-$C_{10}$ or phenyl), or $R^{42}$-substituted or unsubstituted heteroaryl (e.g., 5 to 10 membered, 5 to 9 membered, or 5 to 6 membered). $X^5$ is independently —F, —Cl, —Br, or —I. In embodiments, $X^5$ is —F. In embodiments, $R^5$ is independently hydrogen. In embodiments, $R^5$ is independently unsubstituted methyl. In embodiments, $R^5$ is independently unsubstituted ethyl. In embodiments, $R^5$ is independently hydrogen, oxo, halogen, —$CX^5_3$, —$CHX^5_2$, —$CH_2X^5$, —$OCX^5_3$, —$OCH_2X^5$, —$OCHX^5_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{43}$-substituted or unsubstituted alkyl (e.g., $C_1$-$C_8$, $C_1$-$C_6$, $C_1$-$C_4$, or $C_1$-$C_2$), $R^{43}$-substituted or unsubstituted heteroalkyl (e.g., 2 to 8 membered, 2 to 6 membered, 4 to 6 membered, 2 to 3 membered, or 4 to 5 membered), $R^{43}$-substituted or unsubstituted cycloalkyl (e.g., $C_3$-$C_8$, $C_3$-$C_6$, $C_4$-$C_6$, or $C_5$-$C_6$), $R^{43}$-substituted or unsubstituted heterocycloalkyl (e.g., 3 to 6 membered, 4 to 6 membered, 4 to 5 membered, or 5 to 6 membered), $R^{43}$-substituted or unsubstituted aryl (e.g., $C_6$-$C_{10}$ or phenyl), or $R^{43}$-substituted or unsubstituted heteroaryl (e.g., 5 to 10 membered, 5 to 9 membered, or 5 to 6 membered). $X^{42}$ is independently —F, —Cl, —Br, or —I. In embodiments, $X^{42}$ is —F. In embodiments, $R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{43}$ is independently oxo, halogen, —$CX^{43}_3$, —$CHX^{43}_2$, —$CH_2X^{43}$, —$OCX^{43}_3$, —$OCH_2X^{43}$, —$OCHX^{43}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{44}$-substituted or unsubstituted alkyl (e.g., $C_1$-$C_8$, $C_1$-$C_6$, $C_1$-$C_4$, or $C_1$-$C_2$), $R^{44}$-substituted or unsubstituted heteroalkyl (e.g., 2 to 8 membered, 2 to 6 membered, 4 to 6 membered, 2 to 3 membered, or 4 to 5 membered), $R^{44}$-substituted or unsubstituted cycloalkyl (e.g., $C_3$-$C_8$, $C_3$-$C_6$, $C_4$-$C_6$, or $C_5$-$C_6$), $R^{44}$-substituted or unsubstituted heterocycloalkyl (e.g., 3 to 6 membered, 4 to 6 membered, 4 to 5 membered, or 5 to 6 membered), $R^{44}$-substituted or unsubstituted aryl (e.g., $C_6$-$C_{10}$ or phenyl), or $R^{44}$-substituted or unsubstituted heteroaryl (e.g., 5 to 10 membered, 5 to 9 membered, or 5 to 6 membered). $X^{43}$ is independently —F, —Cl, —Br, or —I. In embodiments, $X^{43}$ is —F. In embodiments, $R^{43}$ is independently oxo, halogen, —$CX^{43}_3$, —$CHX^{43}_2$, —$CH_2X^{43}$, —$OCX^{43}_3$, —$OCH_2X^{43}$, —$OCHX^{43}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{44}$ is independently oxo, halogen, —$CX^{44}_3$, —$CHX^{44}_2$, —$CH_2X^{44}$, —$OCX^{44}_3$, —$OCH_2X^{44}$, —$OCHX^{44}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{44}$ is independently —F, —Cl, —Br, or —I. In embodiments, $X^{44}$ is —F.

In embodiments, $R^6$ is independently hydrogen, oxo, halogen, —$CX^6_3$, —$CHX^6_2$, —$CH_2X^6$, —$OCX^6_3$, —$OCH_2X^6$, —$OCHX^6_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{45}$-substituted or unsubstituted alkyl (e.g., $C_1$-$C_8$, $C_1$-$C_6$, $C_1$-$C_4$, or $C_1$-$C_2$), $R^{45}$-substituted or unsubstituted heteroalkyl (e.g., 2 to 8 membered, 2 to 6 membered, 4 to 6 membered, 2 to 3 membered, or 4 to 5 membered), $R^{45}$-substituted or unsubstituted cycloalkyl (e.g., $C_3$-$C_8$, $C_3$-$C_6$, $C_4$-$C_6$, or $C_5$-$C_6$), $R^{45}$-substituted or unsubstituted heterocycloalkyl (e.g., 3 to 6 membered, 4 to 6 membered, 4 to 5 membered, or 5 to 6 membered), $R^{45}$-substituted or unsubstituted aryl (e.g., $C_6$-$C_{10}$ or phenyl), or $R^{45}$-substituted or unsubstituted heteroaryl (e.g., 5 to 10 membered, 5 to 9 membered, or 5 to 6 membered). $X^6$ is independently —F, —Cl, —Br, or —I. In embodiments, $X^6$ is —F. In embodiments, $R^6$ is independently hydrogen. In embodiments, $R^6$ is independently unsubstituted methyl. In embodiments, $R^6$ is independently unsubstituted ethyl. In embodiments, $R^6$ is independently hydrogen, oxo, halogen, —$CX^6_3$, —$CHX^6_2$, —$CH_2X^6$, —$OCX^6_3$, —$OCH_2X^6$, —$OCHX^6_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{45}$ is independently oxo, halogen, —$CX^{45}_3$, —$CHX^{45}_2$, —$CH_2X^{45}$, —$OCX^{45}_3$, —$OCH_2X^{45}$, —$OCHX^{45}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{46}$-substituted or unsubstituted alkyl (e.g., $C_1$-$C_8$, $C_1$-$C_6$, $C_1$-$C_4$, or $C_1$-$C_2$), $R^{46}$-substituted or unsubstituted heteroalkyl (e.g., 2 to 8 membered, 2 to 6 membered, 4 to 6 membered, 2 to 3 membered, or 4 to 5 membered), $R^{46}$-substituted or unsubstituted cycloalkyl (e.g., $C_3$-$C_8$, $C_3$-$C_6$, $C_4$-$C_6$, or $C_5$-$C_6$), $R^{46}$-substituted or unsubstituted heterocycloalkyl (e.g., 3 to 6 membered, 4 to 6 membered, 4 to 5 membered, or 5 to 6 membered), $R^{46}$-substituted or unsubstituted aryl (e.g., $C_6$-$C_{10}$ or phenyl), or $R^{46}$-substituted or unsubstituted heteroaryl (e.g., 5 to 10 membered, 5 to 9 membered, or 5 to 6 membered). $X^{45}$ is independently —F, —Cl, —Br, or —I. In embodiments, $X^{45}$ is —F. In embodiments, $R^{45}$ is independently oxo, halogen, —$CX^{45}_3$, —$CHX^{45}_2$, —$CH_2X^{45}$, —$OCX^{45}_3$, —$OCH_2X^{45}$, —$OCHX^{45}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{46}$ is independently oxo, halogen, —$CX^{46}_3$, —$CHX^{46}_2$, —$CH_2X^{46}$, —$OCX^{46}_3$, —$OCH_2X^{46}$, —$OCHX^{46}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{47}$-substituted or unsubstituted alkyl (e.g., $C_1$-$C_8$, $C_1$-$C_6$, $C_1$-$C_4$, or $C_1$-$C_2$), $R^{47}$-substituted or unsubstituted heteroalkyl (e.g., 2 to 8 membered, 2 to 6 membered, 4 to 6 membered, 2 to 3 membered, or 4 to 5 membered), $R^{47}$-substituted or unsubstituted cycloalkyl (e.g., $C_3$-$C_8$, $C_3$-$C_6$, $C_4$-$C_6$, or $C_5$-$C_6$), $R^{47}$-substituted or unsubstituted heterocycloalkyl (e.g., 3 to 6 membered, 4 to 6 membered, 4 to 5 membered, or 5 to 6 membered), $R^{47}$-substituted or unsubstituted aryl (e.g., $C_6$-$C_{10}$ or phenyl), or $R^{47}$-substituted or unsubstituted heteroaryl (e.g., 5 to 10 membered, 5 to 9 membered, or 5 to 6 membered). $X^{46}$ is independently —F, —Cl, —Br, or —I. In embodiments, $X^{46}$ is —F. In embodiments, $R^{46}$ is independently oxo, halogen, —$CX^{46}_3$, —$CHX^{46}_2$, —$CH_2X^{46}$, —$OCX^{46}_3$, —$OCH_2X^{46}$, —$OCHX^{46}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{47}$ is independently oxo, halogen, —$CX^{47}_3$, —$CHX^{47}_2$, —$CH_2X^{47}$, —$OCX^{47}_3$, —$OCH_2X^{47}$, —$OCHX^{47}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{47}$ is independently —F, —Cl, —Br, or —I. In embodiments, $X^{47}$ is —F.

In embodiments, $R^7$ is independently hydrogen, oxo, halogen, —$CX^7_3$, —$CHX^7_2$, —$CH_2X^7$, —$OCX^7_3$, —$OCH_2X^7$, —$OCHX^7_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{48}$-substituted or unsubstituted alkyl (e.g., $C_1$-$C_8$, $C_1$-$C_6$, $C_1$-$C_4$, or $C_1$-$C_2$), $R^{48}$-substituted or unsubstituted heteroalkyl (e.g., 2 to 8 membered, 2 to 6 membered, 4 to 6 membered, 2 to 3 membered, or 4 to 5 membered), $R^{48}$-substituted or unsubstituted cycloalkyl (e.g., $C_3$-$C_8$, $C_3$-$C_6$, $C_4$-$C_6$, or $C_5$-$C_6$), $R^{48}$-substituted or unsubstituted heterocycloalkyl (e.g., 3 to 6 membered, 4 to 6 membered, 4 to 5 membered, or 5 to 6 membered), $R^{48}$-substituted or unsubstituted aryl (e.g., $C_6$-$C_{10}$ or phenyl), or $R^{48}$-substituted or unsubstituted heteroaryl (e.g., 5 to 10 membered, 5 to 9 membered, or 5 to 6 membered). $X^7$ is independently —F, —Cl, —Br, or —I. In embodiments, $X^7$ is —F. In embodiments, $R^7$ is independently hydrogen. In embodiments, $R^7$ is independently unsubstituted methyl. In embodiments, $R^7$ is independently unsubstituted ethyl. In embodiments, $R^7$ is independently hydrogen, oxo, halogen, —$CX^7_3$, —$CHX^7_2$, —$CH_2X^7$, —$OCX^7_3$, —$OCH_2X^7$, —$OCHX^7_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{48}$ is independently oxo, halogen, —$CX^{48}_3$, —$CHX^{48}_2$, —$CH_2X^{48}$, —$OCX^{48}_3$, —$OCH_2X^{48}$, —$OCHX^{48}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{49}$-substituted or unsubstituted alkyl (e.g., $C_1$-$C_8$, $C_1$-$C_6$, $C_1$-$C_4$, or $C_1$-$C_2$), $R^{49}$-substituted or unsubstituted heteroalkyl (e.g., 2 to 8 membered, 2 to 6 membered, 4 to 6 membered, 2 to 3 membered, or 4 to 5 membered), $R^{49}$-substituted or unsubstituted cycloalkyl (e.g., $C_3$-$C_8$, $C_3$-$C_6$, $C_4$-$C_6$, or $C_5$-$C_6$), $R^{49}$-substituted or unsubstituted heterocycloalkyl (e.g., 3 to 6 membered, 4 to 6 membered, 4 to 5 membered, or 5 to 6 membered), $R^{49}$-substituted or unsubstituted aryl (e.g., $C_6$-$C_{10}$ or phenyl), or $R^{49}$-substituted or unsubstituted heteroaryl (e.g., 5 to 10 membered, 5 to 9 membered, or 5 to 6 membered). $X^{48}$ is independently —F, —Cl, —Br, or —I. In embodiments, $X^{48}$ is —F. In embodiments, $R^{48}$ is independently oxo, halogen, —$CX^{48}_3$, —$CHX^{48}_2$, —$CH_2X^{48}$, —$OCX^{48}_3$, —$OCH_2X^{48}$, —$OCHX^{48}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or C5-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{49}$ is independently oxo, halogen, —$CX^{49}_3$, —$CHX^{49}_2$, —$CH_2X^{49}$, —$OCX^{49}_3$, —$OCH_2X^{49}$, —$OCHX^{49}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{50}$-substituted or unsubstituted alkyl (e.g., $C_1$-$C_8$, $C_1$-$C_6$, $C_1$-$C_4$, or $C_1$-$C_2$), $R^{50}$-substituted or unsubstituted heteroalkyl (e.g., 2 to 8 membered, 2 to 6 membered, 4 to 6 membered, 2 to 3 membered, or 4 to 5 membered), $R^{50}$-substituted or unsubstituted cycloalkyl (e.g., $C_3$-$C_8$, $C_3$-$C_6$, $C_4$-$C_6$, or $C_5$-$C_6$), $R^{50}$-substituted or unsubstituted heterocycloalkyl (e.g., 3 to 6 membered, 4 to 6 membered, 4 to 5 membered, or 5 to 6 membered), $R^{50}$-substituted or unsubstituted aryl (e.g., $C_6$-$C_{10}$ or phenyl), or $R^{50}$-substituted or unsubstituted heteroaryl (e.g., 5 to 10 membered, 5 to 9 membered, or 5 to 6 membered). $X^{49}$ is independently —F, —Cl, —Br, or —I. In embodiments, $X^{49}$ is —F. In embodiments, $R^{49}$ is independently oxo, halogen, —$CX^{49}_3$, —$CHX^{49}_2$, —$CH_2X^{49}$, —$OCX^{49}_3$, —$OCH_2X^{49}$, —$OCHX^{49}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{50}$ is independently oxo, halogen, —$CX^{50}_3$, —$CHX^{50}_2$, —$CH_2X^{50}$, —$OCX^{50}_3$, —$OCH_2X^{50}$, —$OCHX^{50}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{50}$ is independently —F, —Cl, —Br, or —I. In embodiments, $X^{50}$ is —F.

In embodiments, $R^8$ is independently hydrogen, oxo, halogen, —$CX^8_3$, —$CHX^8_2$, —$CH_2X^8$, —$OCX^8_3$, —$OCH_2X^8$, —$OCHX^8_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{51}$-substituted or unsubstituted alkyl (e.g., $C_1$-$C_8$, $C_1$-$C_6$, $C_1$-$C_4$, or $C_1$-$C_2$), $R^{51}$-substituted or unsubstituted heteroalkyl (e.g., 2 to 8 membered, 2 to 6 membered, 4 to 6 membered, 2 to 3 membered, or 4 to 5 membered), $R^{51}$-substituted or unsubstituted cycloalkyl (e.g., $C_3$-$C_8$, $C_3$-$C_6$, $C_4$-$C_6$, or $C_5$-$C_6$), $R^{51}$-substituted or unsubstituted heterocycloalkyl (e.g., 3 to 6 membered, 4 to 6 membered, 4 to 5 membered, or 5 to 6 membered), $R^{51}$-substituted or unsubstituted aryl (e.g., $C_6$-$C_{10}$ or phenyl), or $R^{51}$-substituted or unsubstituted heteroaryl (e.g., 5 to 10 membered, 5 to 9 membered, or 5 to 6 membered). $X^8$ is independently —F, —Cl, —Br, or —I. In embodiments, $X^8$ is —F. In embodiments, $R^8$ is independently hydrogen. In embodiments, $R^8$ is independently unsubstituted methyl. In embodiments, $R^8$ is independently unsubstituted ethyl. In embodiments, $R^8$ is independently hydrogen, oxo, halogen, —$CX^8_3$, —$CHX^8_2$, —$CH_2X^8$, —$OCX^8_3$, —$OCH_2X^8$, —$OCHX^8_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{51}$ is independently oxo, halogen, —$CX^{51}_3$, —$CHX^{51}_2$, —$CH_2X^{51}$, —$OCX^{51}_3$, —$OCH_2X^{51}$, —$OCHX^{51}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{52}$-substituted or unsubstituted alkyl (e.g., $C_1$-$C_8$, $C_1$-$C_6$, $C_1$-$C_4$, or $C_1$-$C_2$), $R^{52}$-substituted or unsubstituted heteroalkyl (e.g., 2 to 8 membered, 2 to 6 membered, 4 to 6 membered, 2 to 3 membered, or 4 to 5 membered), $R^{52}$-substituted or unsubstituted cycloalkyl (e.g., $C_3$-$C_8$, $C_3$-$C_6$, $C_4$-$C_6$, or $C_5$-$C_6$), $R^{52}$-substituted or unsubstituted heterocycloalkyl (e.g., 3 to 6 membered, 4 to 6 membered, 4 to 5 membered, or 5 to 6 membered), $R^{52}$-substituted or unsubstituted aryl (e.g., $C_6$-$C_{10}$ or phenyl), or $R^{52}$-substituted or unsubstituted heteroaryl (e.g., 5 to 10 membered, 5 to 9 membered, or 5 to 6 membered). $X^{51}$ is independently —F, —Cl, —Br, or —I. In embodiments, $X^{51}$ is —F. In embodiments, $R^{51}$ is independently oxo, halogen, —$CX^{51}_3$, —$CHX^{51}_2$, —$CH_2X^{51}$, —$OCX^{51}_3$, —$OCH_2X^{51}$, —$OCHX^{51}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{52}$ is independently oxo, halogen, —$CX^{52}_3$, —$CHX^{52}_2$, —$CH_2X^{52}$, —$OCX^{52}_3$, —$OCH_2X^{52}$, —$OCHX^{52}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{53}$-substituted or unsubstituted alkyl (e.g., $C_1$-$C_8$, $C_1$-$C_6$, $C_1$-$C_4$, or $C_1$-$C_2$), $R^{53}$-substituted or unsubstituted heteroalkyl (e.g., 2 to 8 membered, 2 to 6 membered, 4 to 6 membered, 2 to 3 membered, or 4 to 5 membered), $R^{53}$-substituted or unsubstituted cycloalkyl (e.g., $C_3$-$C_8$, $C_3$-$C_6$, $C_4$-$C_6$, or $C_5$-$C_6$), $R^{53}$-substituted or unsubstituted heterocycloalkyl (e.g., 3 to 6 membered, 4 to 6 membered, 4 to 5 membered, or 5 to 6 membered), $R^{53}$-substituted or unsubstituted aryl (e.g., $C_6$-$C_{10}$ or phenyl), or $R^{53}$-substituted or unsubstituted heteroaryl (e.g., 5 to 10 membered, 5 to 9 membered, or 5 to 6 membered). $X^{52}$ is independently —F, —Cl, —Br, or —I. In embodiments, $X^{52}$ is —F. In embodiments, $R^{52}$ is independently oxo, halogen, —$CX^{52}_3$, —$CHX^{52}_2$, —$CH_2X^{52}$, —$OCX^{52}_3$, —$OCH_2X^{52}$, —$OCHX^{52}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{53}$ is independently oxo, halogen, —$CX^{53}_3$, —$CHX^{53}_2$, —$CH_2X^{53}$, —$OCX^{53}_3$, —$OCH_2X^{53}$, —$OCHX^{53}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{53}$ is independently —F, —Cl, —Br, or —I. In embodiments, $X^{53}$ is —F.

In embodiments, $R^9$ is independently hydrogen, oxo, halogen, —$CX^9_3$, —$CHX^9_2$, —$CH_2X^9$, —$OCX^9_3$, —$OCH_2X^9$, —$OCHX^9_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{54}$-substituted or unsubstituted alkyl (e.g., $C_1$-$C_8$, $C_1$-$C_6$, $C_1$-$C_4$, or $C_1$-$C_2$), $R^{54}$-substituted or unsubstituted heteroalkyl (e.g., 2 to 8 membered, 2 to 6 membered, 4 to 6 membered, 2 to 3 membered, or 4 to 5 membered), $R^{54}$-substituted or unsubstituted cycloalkyl (e.g., $C_3$-$C_8$, $C_3$-$C_6$, $C_4$-$C_6$, or $C_5$-$C_6$), $R^{54}$-substituted or unsubstituted heterocycloalkyl (e.g., 3 to 6 membered, 4 to 6 membered, 4 to 5 membered, or 5 to 6 membered), $R^{54}$-substituted or unsubstituted aryl (e.g., $C_6$-$C_{10}$ or phenyl), or $R^{54}$-substituted or unsubstituted heteroaryl (e.g., 5 to 10 membered, 5 to 9 membered, or 5 to 6 membered). $X^9$ is independently —F, —Cl, —Br, or —I. In embodiments, $X^9$ is —F. In embodiments, $R^9$ is independently hydrogen. In embodiments, $R^9$ is independently unsubstituted methyl. In embodiments, $R^9$ is independently unsubstituted ethyl. In embodiments, $R^9$ is independently hydrogen, oxo, halogen, —$CX^9_3$, —$CHX^9_2$, —$CH_2X^9$, —$OCX^9_3$, —$OCH_2X^9$, —$OCHX^9_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{54}$ is independently oxo, halogen, —$CX^{54}_3$, —$CHX^{54}_2$, —$CH_2X^{54}$, —$OCX^{54}_3$, —$OCH_2X^{54}$, —$OCHX^{54}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{55}$-substituted or unsubstituted alkyl (e.g., $C_1$-$C_8$, $C_1$-$C_6$, $C_1$-$C_4$, or $C_1$-$C_2$), $R^{55}$-substituted or unsubstituted heteroalkyl (e.g., 2 to 8 membered, 2 to 6 membered, 4 to 6 membered, 2 to 3 membered, or 4 to 5 membered), $R^{55}$-substituted or unsubstituted cycloalkyl (e.g., $C_3$-$C_8$, $C_3$-$C_6$, $C_4$-$C_6$, or $C_5$-$C_6$), $R^{55}$-substituted or unsubstituted heterocycloalkyl (e.g., 3 to 6 membered, 4 to 6 membered, 4 to 5 membered, or 5 to 6 membered), $R^{55}$-substituted or unsubstituted aryl (e.g., $C_6$-$C_{10}$ or phenyl), or $R^{55}$-substituted or unsubstituted heteroaryl (e.g., 5 to 10 membered, 5 to 9 membered, or 5 to 6 membered). $X^{54}$ is independently —F, —Cl, —Br, or —I. In embodiments, $X^{54}$ is —F. In embodiments, $R^{54}$ is independently oxo, halogen, —$CX^{54}_3$, —$CHX^{54}_2$, —$CH_2X^{54}$, —$OCX^{54}_3$, —$OCH_2X^{54}$, —$OCHX^{54}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{55}$ is independently oxo, halogen, —$CX^{55}_3$, —$CHX^{55}_2$, —$CH_2X^{55}$, —$OCX^{55}_3$, —$OCH_2X^{55}$, —$OCHX^{55}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{56}$-substituted or unsubstituted alkyl (e.g., $C_1$-$C_8$, $C_1$-$C_6$, $C_1$-$C_4$, or $C_1$-$C_2$), $R^{56}$-substituted or unsubstituted heteroalkyl (e.g., 2 to 8 membered, 2 to 6 membered, 4 to 6 membered, 2 to 3 membered, or 4 to 5 membered), $R^{56}$-substituted or unsubstituted cycloalkyl (e.g., $C_3$-$C_8$, $C_3$-$C_6$, $C_4$-$C_6$, or $C_5$-$C_6$), $R^{56}$-substituted or unsubstituted heterocycloalkyl (e.g., 3 to 6 membered, 4 to 6 membered, 4 to 5 membered, or 5 to 6 membered), $R^{56}$-substituted or unsubstituted aryl (e.g., $C_6$-$C_{10}$ or phenyl), or $R^{56}$-substituted or unsubstituted heteroaryl (e.g., 5 to 10 membered, 5 to 9 membered, or 5 to 6 membered). $X^{55}$ is independently —F, —Cl, —Br, or —I. In embodiments, $X^{55}$ is —F. In embodiments, $R^{55}$ is independently oxo, halogen, —$CX^{55}_3$, —$CHX^{55}_2$, —$CH_2X^{55}$, —$OCX^{55}_3$, —$OCH_2X^{55}$, —$OCHX^{55}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{56}$ is independently oxo, halogen, —$CX^{56}_3$, —$CHX^{56}_2$, —$CH_2X^{56}$, —$OCX^{56}_3$, —$OCH_2X^{56}$, —$OCHX^{56}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_3$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or heteroaryl (e.g., 5 to 10 membered, 5 to 9 membered, or 5 to 6 membered). $X^{56}$ is independently —F, —Cl, —Br, or —I. In embodiments, $X^{56}$ is —F.

In embodiments, $R^{10}$ is independently hydrogen, oxo, halogen, —$CX^{10}_3$, —$CHX^{10}_2$, —$CH_2X^{10}$, —$OCX^{10}_3$, —$OCH_2X^{10}$, —$OCHX^{10}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{57}$-substituted or unsubstituted alkyl (e.g., $C_1$-$C_8$, $C_1$-$C_6$, $C_1$-$C_4$, or $C_1$-$C_2$), $R^{57}$-substituted or unsubstituted heteroalkyl (e.g., 2 to 8 membered, 2 to 6 membered, 4 to 6 membered, 2 to 3 membered, or 4 to 5 membered), $R^{57}$-substituted or unsubstituted cycloalkyl (e.g., $C_3$-$C_8$, $C_3$-$C_6$, $C_4$-$C_6$, or $C_5$-$C_6$), $R^{57}$-substituted or unsubstituted heterocycloalkyl (e.g., 3 to 6 membered, 4 to 6 membered, 4 to 5 membered, or 5 to 6 membered), $R^{57}$-substituted or unsubstituted aryl (e.g., $C_6$-$C_{10}$ or phenyl), or $R^{57}$-substituted or unsubstituted heteroaryl (e.g., 5 to 10 membered, 5 to 9 membered, or 5 to 6 membered). $X^{10}$ is independently —F, —Cl, —Br, or —I. In embodiments, $X^{10}$ is —F. In embodiments, $R^{10}$ is independently hydrogen. In embodiments, $R^{10}$ is independently unsubstituted methyl. In embodiments, $R^{10}$ is independently unsubstituted ethyl. In embodiments, $R^{10}$ is independently hydrogen, oxo, halogen, —$CX^{10}_3$, —$CHX^{10}_2$, —$CH_2X^{10}$, —$OCX^{10}_3$, —$OCH_2X^{10}$, —$OCHX^{10}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{57}$ is independently oxo, halogen, —CX$^{57}_3$, —CHX$^{57}_2$, —CH$_2$X$^{57}$, —OCX$^{57}_3$, —OCH$_2$X$^{57}$, —OCHX$^{57}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{58}$-substituted or unsubstituted alkyl (e.g., C$_1$-C$_8$, C$_1$-C$_6$, C$_1$-C$_4$, or C$_1$-C$_2$), R$^{58}$-substituted or unsubstituted heteroalkyl (e.g., 2 to 8 membered, 2 to 6 membered, 4 to 6 membered, 2 to 3 membered, or 4 to 5 membered), R$^{58}$-substituted or unsubstituted cycloalkyl (e.g., C$_3$-C$_8$, C$_3$-C$_6$, C$_4$-C$_6$, or C$_5$-C$_6$), R$^{58}$-substituted or unsubstituted heterocycloalkyl (e.g., 3 to 6 membered, 4 to 6 membered, 4 to 5 membered, or 5 to 6 membered), R$^{58}$-substituted or unsubstituted aryl (e.g., C$_6$-C$_{10}$ or phenyl), or R$^{58}$-substituted or unsubstituted heteroaryl (e.g., 5 to 10 membered, 5 to 9 membered, or 5 to 6 membered). X$^{57}$ is independently —F, —Cl, —Br, or —I. In embodiments, X$^{57}$ is —F. In embodiments, R$^{57}$ is independently oxo, halogen, —CX$^{57}_3$, —CHX$^{57}_2$, —CH$_2$X$^{57}$, —OCX$^{57}_3$, —OCH$_2$X$^{57}$, —OCHX$^{57}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{58}$ is independently oxo, halogen, —CX$^{58}_3$, —CHX$^{58}_2$, —CH$_2$X$^{58}$, —OCX$^{58}_3$, —OCH$_2$X$^{58}$, —OCHX$^{58}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{59}$-substituted or unsubstituted alkyl (e.g., C$_1$-C$_8$, C$_1$-C$_6$, C$_1$-C$_4$, or C$_1$-C$_2$), R$^{59}$-substituted or unsubstituted heteroalkyl (e.g., 2 to 8 membered, 2 to 6 membered, 4 to 6 membered, 2 to 3 membered, or 4 to 5 membered), R$^{59}$-substituted or unsubstituted cycloalkyl (e.g., C$_3$-C$_8$, C$_3$-C$_6$, C$_4$-C$_6$, or C$_5$-C$_6$), R$^{59}$-substituted or unsubstituted heterocycloalkyl (e.g., 3 to 6 membered, 4 to 6 membered, 4 to 5 membered, or 5 to 6 membered), R$^{59}$-substituted or unsubstituted aryl (e.g., C$_6$-C$_{10}$ or phenyl), or R$^{59}$-substituted or unsubstituted heteroaryl (e.g., 5 to 10 membered, 5 to 9 membered, or 5 to 6 membered). X$^{58}$ is independently —F, —Cl, —Br, or —I. In embodiments, X$^{58}$ is —F. In embodiments, R$^{58}$ is independently oxo, halogen, —CX$^{58}_3$, —CHX$^{58}_2$, —CH$_2$X$^{58}$, —OCX$^{58}_3$, —OCH$_2$X$^{58}$, —OCHX$^{58}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{59}$ is independently oxo, halogen, —CX$^{59}_3$, —CHX$^{59}_2$, —CH$_2$X$^{59}$, —OCX$^{59}_3$, —OCH$_2$X$^{59}$, —OCHX$^{59}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{59}$ is independently —F, —Cl, —Br, or —I. In embodiments, X$^{59}$ is —F.

In embodiments, R$^{11}$ is independently hydrogen, oxo, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{60}$-substituted or unsubstituted alkyl (e.g., C$_1$-C$_8$, C$_1$-C$_6$, C$_1$-C$_4$, or C$_1$-C$_2$), R$^{60}$-substituted or unsubstituted heteroalkyl (e.g., 2 to 8 membered, 2 to 6 membered, 4 to 6 membered, 2 to 3 membered, or 4 to 5 membered), R$^{60}$-substituted or unsubstituted cycloalkyl (e.g., C$_3$-C$_8$, C$_3$-C$_6$, C$_4$-C$_6$, or C$_5$-C$_6$), R$^{60}$-substituted or unsubstituted heterocycloalkyl (e.g., 3 to 6 membered, 4 to 6 membered, 4 to 5 membered, or 5 to 6 membered), R$^{60}$-substituted or unsubstituted aryl (e.g., C$_6$-C$_{10}$ or phenyl), or R$^{60}$-substituted or unsubstituted heteroaryl (e.g., 5 to 10 membered, 5 to 9 membered, or 5 to 6 membered). X$^{11}$ is independently —F, —Cl, —Br, or —I. In embodiments, X$^{11}$ is —F. In embodiments, R$^{11}$ is independently hydrogen. In embodiments, R$^{11}$ is independently unsubstituted methyl. In embodiments, R$^{11}$ is independently unsubstituted ethyl. In embodiments, R$^{11}$ is independently hydrogen, oxo, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{60}$ is independently oxo, halogen, —CX$^{60}_3$, —CHX$^{60}_2$, —CH$_2$X$^{60}$, —OCX$^{60}_3$, —OCH$_2$X$^{60}$, —OCHX$^{60}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{61}$-substituted or unsubstituted alkyl (e.g., C$_1$-C$_8$, C$_1$-C$_6$, C$_1$-C$_4$, or $C_1$-$C_2$), $R^{61}$-substituted or unsubstituted heteroalkyl (e.g., 2 to 8 membered, 2 to 6 membered, 4 to 6 membered, 2 to 3 membered, or 4 to 5 membered), $R^{61}$-substituted or unsubstituted cycloalkyl (e.g., $C_3$-$C_8$, $C_3$-$C_6$, $C_4$-$C_6$, or $C_5$-$C_6$), $R^{61}$-substituted or unsubstituted heterocycloalkyl (e.g., 3 to 6 membered, 4 to 6 membered, 4 to 5 membered, or 5 to 6 membered), $R^{61}$-substituted or unsubstituted aryl (e.g., $C_6$-$C_{10}$ or phenyl), or $R^{61}$-substituted or unsubstituted heteroaryl (e.g., 5 to 10 membered, 5 to 9 membered, or 5 to 6 membered). $X^{60}$ is independently —F, —Cl, —Br, or —I. In embodiments, $X^{60}$ is —F. In embodiments, $R^{60}$ is independently oxo, halogen, —$CX^{60}_3$, —$CHX^{60}_2$, —$CH_2X^{60}$, —$OCX^{60}_3$, —$OCH_2X^{60}$, —$OCHX^{60}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{61}$ is independently oxo, halogen, —$CX^{61}_3$, —$CHX^{61}_2$, —$CH_2X^{61}$, —$OCX^{61}_3$, —$OCH_2X^{61}$, —$OCHX^{61}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{62}$-substituted or unsubstituted alkyl (e.g., $C_1$-$C_8$, $C_1$-$C_6$, $C_1$-$C_4$, or $C_1$-$C_2$), $R^{62}$-substituted or unsubstituted heteroalkyl (e.g., 2 to 8 membered, 2 to 6 membered, 4 to 6 membered, 2 to 3 membered, or 4 to 5 membered), $R^{62}$-substituted or unsubstituted cycloalkyl (e.g., $C_3$-$C_8$, $C_3$-$C_6$, $C_4$-$C_6$, or $C_5$-$C_6$), $R^{62}$-substituted or unsubstituted heterocycloalkyl (e.g., 3 to 6 membered, 4 to 6 membered, 4 to 5 membered, or 5 to 6 membered), $R^{62}$-substituted or unsubstituted aryl (e.g., $C_6$-$C_{10}$ or phenyl), or $R^{62}$-substituted or unsubstituted heteroaryl (e.g., 5 to 10 membered, 5 to 9 membered, or 5 to 6 membered). $X^{61}$ is independently —F, —Cl, —Br, or —I. In embodiments, $X^{61}$ is —F. In embodiments, $R^{61}$ is independently oxo, halogen, —$CX^{61}_3$, —$CHX^{61}_2$, —$CH_2X^{61}$, —$OCX^{61}_3$, —$OCH_2X^{61}$, —$OCHX^{61}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{62}$ is independently oxo, halogen, —$CX^{62}_3$, —$CHX^{62}_2$, —$CH_2X^{62}$, —$OCX^{62}_3$, —$OCH_2X^{62}$, —$OCHX^{62}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{62}$ is independently —F, —Cl, —Br, or —I. In embodiments, $X^{62}$ is —F.

In embodiments, $R^{12}$ is independently hydrogen, oxo, halogen, —$CX^{12}_3$, —$CHX^{12}_2$, —$CH_2X^{12}$, —$OCX^{12}_3$, —$OCH_2X^{12}$, —$OCHX^{12}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{63}$-substituted or unsubstituted alkyl (e.g., $C_1$-$C_8$, $C_1$-$C_6$, $C_1$-$C_4$, or $C_1$-$C_2$), $R^{63}$-substituted or unsubstituted heteroalkyl (e.g., 2 to 8 membered, 2 to 6 membered, 4 to 6 membered, 2 to 3 membered, or 4 to 5 membered), $R^{63}$-substituted or unsubstituted cycloalkyl (e.g., $C_3$-$C_8$, $C_3$-$C_6$, $C_4$-$C_6$, or $C_5$-$C_6$), $R^{63}$-substituted or unsubstituted heterocycloalkyl (e.g., 3 to 6 membered, 4 to 6 membered, 4 to 5 membered, or 5 to 6 membered), $R^{63}$-substituted or unsubstituted aryl (e.g., $C_6$-$C_{10}$ or phenyl), or $R^{63}$-substituted or unsubstituted heteroaryl (e.g., 5 to 10 membered, 5 to 9 membered, or 5 to 6 membered). $X^{12}$ is independently —F, —Cl, —Br, or —I. In embodiments, $X^{12}$ is —F. In embodiments, $R^{12}$ is independently hydrogen. In embodiments, $R^{12}$ is independently unsubstituted methyl. In embodiments, $R^{12}$ is independently unsubstituted ethyl. In embodiments, $R^{12}$ is independently hydrogen, oxo, halogen, —$CX^{12}_3$, —$CHX^{12}_2$, —$CH_2X^{12}$, —$OCX^{12}_3$, —$OCH_2X^{12}$, —$OCHX^{12}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{63}$ is independently oxo, halogen, —$CX^{63}_3$, —$CHX^{63}_2$, —$CH_2X^{63}$, —$OCX^{63}_3$, —$OCH_2X^{63}$, —$OCHX^{63}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{64}$-substituted or unsubstituted alkyl (e.g., $C_1$-$C_8$, $C_1$-$C_6$, $C_1$-$C_4$, or $C_1$-$C_2$), $R^{64}$-substituted or unsubstituted heteroalkyl (e.g., 2 to 8 membered, 2 to 6 membered, 4 to 6 membered, 2 to 3 membered, or 4 to 5 membered), $R^{64}$-substituted or unsubstituted cycloalkyl (e.g., $C_3$-$C_8$, $C_3$-$C_6$, $C_4$-$C_6$, or $C_5$-$C_6$), $R^{64}$-substituted or unsubstituted heterocycloalkyl (e.g., 3 to 6 membered, 4 to 6 membered, 4 to 5 membered, or 5 to 6 membered), $R^{64}$-substituted or unsubstituted aryl (e.g., $C_6$-$C_{10}$ or phenyl), or $R^{64}$-substituted or unsubstituted heteroaryl (e.g., 5 to 10 membered, 5 to 9 membered, or 5 to 6 membered). $X^{63}$ is independently —F, —Cl, —Br, or —I. In embodiments, $X^{63}$ is —F. In embodiments, $R^{63}$ is independently oxo, halogen, —$CX^{63}_3$, —$CHX^{63}_2$, —$CH_2X^{63}$, —$OCX^{63}_3$, —$OCH_2X^{63}$, —$OCHX^{63}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{64}$ is independently oxo, halogen, —$CX^{64}_3$, —$CHX^{64}_2$, —$CH_2X^{64}$, —$OCX^{64}_3$, —$OCH_2X^{64}$, —$OCHX^{64}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{65}$-substituted or unsubstituted alkyl (e.g., $C_1$-$C_8$, $C_1$-$C_6$, $C_1$-$C_4$, or $C_1$-$C_2$), $R^{65}$-substituted or unsubstituted heteroalkyl (e.g., 2 to 8 membered, 2 to 6 membered, 4 to 6 membered, 2 to 3 membered, or 4 to 5 membered), $R^{65}$-substituted or unsubstituted cycloalkyl (e.g., $C_3$-$C_8$, $C_3$-$C_6$, $C_4$-$C_6$, or $C_5$-$C_6$), $R^{65}$-substituted or unsubstituted heterocycloalkyl (e.g., 3 to 6 membered, 4 to 6 membered, 4 to 5 membered, or 5 to 6 membered), $R^{65}$-substituted or unsubstituted aryl (e.g., $C_6$-$C_{10}$ or phenyl), or $R^{65}$-substituted or unsubstituted heteroaryl (e.g., 5 to 10 membered, 5 to 9 membered, or 5 to 6 membered). $X^{64}$ is independently —F, —Cl, —Br, or —I. In embodiments, $X^{64}$ is —F. In embodiments, $R^{64}$ is independently oxo, halogen, —$CX^{64}_3$, —$CHX^{64}_2$, —$CH_2X^{64}$, —$OCX^{64}_3$, —$OCH_2X^{64}$, —$OCHX^{64}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{65}$ is independently oxo, halogen, —$CX^{65}_3$, —$CHX^{65}_2$, —$CH_2X^{65}$, —$OCX^{65}_3$, —$OCH_2X^{65}$, —$OCHX^{65}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, C3-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{65}$ is independently —F, —Cl, —Br, or —I. In embodiments, $X^{65}$ is —F.

In embodiments, $R^{13}$ is independently hydrogen, oxo, halogen, —$CX^{13}_3$, —$CHX^{13}_2$, —$CH_2X^{13}$, —$OCX^{13}_3$, —$OCH_2X^{13}$, —$OCHX^{13}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{66}$-substituted or unsubstituted alkyl (e.g., $C_1$-$C_8$, $C_1$-$C_6$, $C_1$-$C_4$, or $C_1$-$C_2$), $R^{66}$-substituted or unsubstituted heteroalkyl (e.g., 2 to 8 membered, 2 to 6 membered, 4 to 6 membered, 2 to 3 membered, or 4 to 5 membered), $R^{66}$-substituted or unsubstituted cycloalkyl (e.g., $C_3$-$C_8$, $C_3$-$C_6$, $C_4$-$C_6$, or $C_5$-$C_6$), $R^{66}$-substituted or unsubstituted heterocycloalkyl (e.g., 3 to 6 membered, 4 to 6 membered, 4 to 5 membered, or 5 to 6 membered), $R^{66}$-substituted or unsubstituted aryl (e.g., $C_6$-$C_{10}$ or phenyl), or $R^{66}$-substituted or unsubstituted heteroaryl (e.g., 5 to 10 membered, 5 to 9 membered, or 5 to 6 membered). $X^{13}$ is independently —F, —Cl, —Br, or —I. In embodiments, $X^{13}$ is —F. In embodiments, $R^{13}$ is independently hydrogen. In embodiments, $R^{13}$ is independently unsubstituted methyl. In embodiments, $R^{13}$ is independently unsubstituted ethyl. In embodiments, $R^{13}$ is independently hydrogen, oxo, halogen, —$CX^{13}_3$, —$CHX^{13}_2$, —$CH_2X^{13}$, —$OCX^{13}_3$, —$OCH_2X^{13}$, —$OCHX^{13}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{66}$ is independently oxo, halogen, —$CX^{66}_3$, —$CHX^{66}_2$, —$CH_2X^{66}$, —$OCX^{66}_3$, —$OCH_2X^{66}$, —$OCHX^{66}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{67}$-substituted or unsubstituted alkyl (e.g., $C_1$-$C_8$, $C_1$-$C_6$, $C_1$-$C_4$, or $C_1$-$C_2$), $R^{67}$-substituted or unsubstituted heteroalkyl (e.g., 2 to 8 membered, 2 to 6 membered, 4 to 6 membered, 2 to 3 membered, or 4 to 5 membered), $R^{67}$-substituted or unsubstituted cycloalkyl (e.g., $C_3$-$C_8$, $C_3$-$C_6$, $C_4$-$C_6$, or $C_5$-$C_6$), $R^{67}$-substituted or unsubstituted heterocycloalkyl (e.g., 3 to 6 membered, 4 to 6 membered, 4 to 5 membered, or 5 to 6 membered), $R^{67}$-substituted or unsubstituted aryl (e.g., $C_6$-$C_{10}$ or phenyl), or $R^{67}$-substituted or unsubstituted heteroaryl (e.g., 5 to 10 membered, 5 to 9 membered, or 5 to 6 membered). $X^{66}$ is independently —F, —Cl, —Br, or —I. In embodiments, $X^{66}$ is —F. In embodiments, $R^{66}$ is independently oxo, halogen, —$CX^{66}_3$, —$CHX^{66}_2$, —$CH_2X^{66}$, —$OCX^{66}_3$, —$OCH_2X^{66}$, —$OCHX^{66}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{67}$ is independently oxo, halogen, —$CX^{67}_3$, —$CHX^{67}_2$, —$CH_2X^{67}$, —$OCX^{67}_3$, —$OCH_2X^{67}$, —$OCHX^{67}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{68}$-substituted or unsubstituted alkyl (e.g., $C_1$-$C_8$, $C_1$-$C_6$, $C_1$-$C_4$, or $C_1$-$C_2$), $R^{68}$-substituted or unsubstituted heteroalkyl (e.g., 2 to 8 membered, 2 to 6 membered, 4 to 6 membered, 2 to 3 membered, or 4 to 5 membered), $R^{68}$-substituted or unsubstituted cycloalkyl (e.g., $C_3$-$C_8$, $C_3$-$C_6$, $C_4$-$C_6$, or $C_5$-$C_6$), $R^{68}$-substituted or unsubstituted heterocycloalkyl (e.g., 3 to 6 membered, 4 to 6 membered, 4 to 5 membered, or 5 to 6 membered), $R^{68}$-substituted or unsubstituted aryl (e.g., $C_6$-$C_{10}$ or phenyl), or $R^{68}$-substituted or unsubstituted heteroaryl (e.g., 5 to 10 membered, 5 to 9 membered, or 5 to 6 membered). $X^{67}$ is independently —F, —Cl, —Br, or —I. In embodiments, $X^{67}$ is —F. In embodiments, $R^{67}$ is independently oxo, halogen, —$CX^{67}_3$, —$CHX^{67}_2$, —$CH_2X^{67}$, —$OCX^{67}_3$, —$OCH_2X^{67}$, —$OCHX^{67}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{68}$ is independently oxo, halogen, —$CX^{68}_3$, —$CHX^{68}_2$, —$CH_2X^{68}$, —$OCX^{68}_3$, —$OCH_2X^{68}$, —$OCHX^{68}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{68}$ is independently —F, —Cl, —Br, or —I. In embodiments, $X^{68}$ is —F.

In embodiments, $R^{14}$ is independently hydrogen, oxo, halogen, —$CX^{14}_3$, —$CHX^{14}_2$, —$CH_2X^{14}$, —$OCX^{14}_3$, —$OCH_2X^{14}$, —$OCHX^{14}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{69}$-substituted or unsubstituted alkyl (e.g., $C_1$-$C_8$, $C_1$-$C_6$, $C_1$-$C_4$, or $C_1$-$C_2$), $R^{69}$-substituted or unsubstituted heteroalkyl (e.g., 2 to 8 membered, 2 to 6 membered, 4 to 6 membered, 2 to 3 membered, or 4 to 5 membered), $R^{69}$-substituted or unsubstituted cycloalkyl (e.g., $C_3$-$C_8$, $C_3$-$C_6$, $C_4$-$C_6$, or $C_5$-$C_6$), $R^{69}$-substituted or unsubstituted heterocycloalkyl (e.g., 3 to 6 membered, 4 to 6 membered, 4 to 5 membered, or 5 to 6 membered), $R^{69}$-substituted or unsubstituted aryl (e.g., $C_6$-$C_{10}$ or phenyl), or $R^{69}$-substituted or unsubstituted heteroaryl (e.g., 5 to 10 membered, 5 to 9 membered, or 5 to 6 membered). $X^{14}$ is independently —F, —Cl, —Br, or —I. In embodiments, $X^{14}$ is —F. In embodiments, $R^{14}$ is independently hydrogen. In embodiments, $R^{14}$ is independently unsubstituted methyl. In embodiments, $R^{14}$ is independently unsubstituted ethyl. In embodiments, $R^{14}$ is independently hydrogen, oxo, halogen, —$CX^{14}_3$, —$CHX^{14}_2$, —$CH_2X^{14}$, —$OCX^{14}_3$, —$OCH_2X^{14}$, —$OCHX^{14}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{69}$ is independently oxo, halogen, —$CX^{69}_3$, —$CHX^{69}_2$, —$CH_2X^{69}$, —$OCX^{69}_3$, —$OCH_2X^{69}$, —$OCHX^{69}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{70}$-substituted or unsubstituted alkyl (e.g., $C_1$-$C_8$, $C_1$-$C_6$, $C_1$-$C_4$, or $C_1$-$C_2$), $R^{70}$-substituted or unsubstituted heteroalkyl (e.g., 2 to 8 membered, 2 to 6 membered, 4 to 6 membered, 2 to 3 membered, or 4 to 5 membered), $R^{70}$-substituted or unsubstituted cycloalkyl (e.g., $C_3$-$C_8$, $C_3$-$C_6$, $C_4$-$C_6$, or $C_5$-$C_6$), $R^{70}$-substituted or unsubstituted heterocycloalkyl (e.g., 3 to 6 membered, 4 to 6 membered, 4 to 5 membered, or 5 to 6 membered), $R^{70}$-substituted or unsubstituted aryl (e.g., $C_6$-$C_{10}$ or phenyl), or $R^{70}$-substituted or unsubstituted heteroaryl (e.g., 5 to 10 membered, 5 to 9 membered, or 5 to 6 membered). $X^{69}$ is independently —F, —Cl, —Br, or —I. In embodiments, $X^{69}$ is —F. In embodiments, $R^{69}$ is independently oxo, halogen, —$CX^{69}_3$, —$CHX^{69}_2$, —$CH_2X^{69}$, —$OCX^{69}_3$, —$OCH_2X^{69}$, —$OCHX^{69}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{70}$ is independently oxo, halogen, —$CX^{70}_3$, —$CHX^{70}_2$, —$CH_2X^{70}$, —$OCX^{70}_3$, —$OCH_2X^{70}$, —$OCHX^{70}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{71}$-substituted or unsubstituted alkyl (e.g., $C_1$-$C_8$, $C_1$-$C_6$, $C_1$-$C_4$, or $C_1$-$C_2$), $R^{71}$-substituted or unsubstituted heteroalkyl (e.g., 2 to 8 membered, 2 to 6 membered, 4 to 6 membered, 2 to 3 membered, or 4 to 5 membered), $R^{71}$-substituted or unsubstituted cycloalkyl (e.g., $C_3$-$C_8$, $C_3$-$C_6$, $C_4$-$C_6$, or $C_5$-$C_6$), $R^{71}$-substituted or unsubstituted heterocycloalkyl (e.g., 3 to 6 membered, 4 to 6 membered, 4 to 5 membered, or 5 to 6 membered), $R^{71}$-substituted or unsubstituted aryl (e.g., $C_6$-$C_{10}$ or phenyl), or $R^{71}$-substituted or unsubstituted heteroaryl (e.g., 5 to 10 membered, 5 to 9 membered, or 5 to 6 membered). $X^{70}$ is independently —F, —Cl, —Br, or —I. In embodiments, $X^{70}$ is —F. In embodiments, $R^{70}$ is independently oxo, halogen, —$CX^{70}_3$, —$CHX^{70}_2$, —$CH_2X^{70}$, —$OCX^{70}_3$, —$OCH_2X^{70}$, —$OCHX^{70}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)

NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{71}$ is independently oxo, halogen, —CX$^{71}_3$, —CHX$^{71}_2$, —CH$_2$X$^{71}$, —OCX$^{71}_3$, —OCH$_2$X$^{71}$, —OCHX$^{71}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{71}$ is independently —F, —Cl, —Br, or —I. In embodiments, X$^{71}$ is —F.

In embodiments, R$^{15}$ is independently hydrogen, oxo, halogen, —CX$^{15}_3$, —CHX$^{15}_2$, —CH$_2$X$^{15}$, —OCX$^{15}_3$, —OCH$_2$X$^{15}$, —OCHX$^{15}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{72}$-substituted or unsubstituted alkyl (e.g., C$_1$-C$_8$, C$_1$-C$_6$, C$_1$-C$_4$, or C$_1$-C$_2$), R$^{72}$-substituted or unsubstituted heteroalkyl (e.g., 2 to 8 membered, 2 to 6 membered, 4 to 6 membered, 2 to 3 membered, or 4 to 5 membered), R$^{72}$-substituted or unsubstituted cycloalkyl (e.g., C$_3$-C$_8$, C$_3$-C$_6$, C$_4$-C$_6$, or C$_5$-C$_6$), R$^{72}$-substituted or unsubstituted heterocycloalkyl (e.g., 3 to 6 membered, 4 to 6 membered, 4 to 5 membered, or 5 to 6 membered), R$^{72}$-substituted or unsubstituted aryl (e.g., C$_6$-C$_{10}$ or phenyl), or R$^{72}$-substituted or unsubstituted heteroaryl (e.g., 5 to 10 membered, 5 to 9 membered, or 5 to 6 membered). X$^{15}$ is independently —F, —Cl, —Br, or —I. In embodiments, X$^{15}$ is —F. In embodiments, R$^{15}$ is independently hydrogen. In embodiments, R$^{15}$ is independently unsubstituted methyl. In embodiments, R$^{15}$ is independently unsubstituted ethyl. In embodiments, R$^{15}$ is independently hydrogen, oxo, halogen, —CX$^{15}_3$, —CHX$^{15}_2$, —CH$_2$X$^{15}$, —OCX$^{15}_3$, —OCH$_2$X$^{15}$, —OCHX$^{15}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{72}$ is independently oxo, halogen, —CX$^{72}_3$, —CHX$^{72}_2$, —CH$_2$X$^{72}$, —OCX$^{72}_3$, —OCH$_2$X$^{72}$, —OCHX$^{72}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{73}$-substituted or unsubstituted alkyl (e.g., C$_1$-C$_8$, C$_1$-C$_6$, C$_1$-C$_4$, or C$_1$-C$_2$), R$^{73}$-substituted or unsubstituted heteroalkyl (e.g., 2 to 8 membered, 2 to 6 membered, 4 to 6 membered, 2 to 3 membered, or 4 to 5 membered), R$^{73}$-substituted or unsubstituted cycloalkyl (e.g., C$_3$-C$_8$, C$_3$-C$_6$, C$_4$-C$_6$, or C$_5$-C$_6$), R$^{73}$-substituted or unsubstituted heterocycloalkyl (e.g., 3 to 6 membered, 4 to 6 membered, 4 to 5 membered, or 5 to 6 membered), R$^{73}$-substituted or unsubstituted aryl (e.g., C$_6$-C$_{10}$ or phenyl), or R$^{73}$-substituted or unsubstituted heteroaryl (e.g., 5 to 10 membered, 5 to 9 membered, or 5 to 6 membered). X$^{72}$ is independently —F, —Cl, —Br, or —I. In embodiments, X$^{72}$ is —F. In embodiments, R$^{72}$ is independently oxo, halogen, —CX$^{72}_3$, —CHX$^{72}_2$, —CH$_2$X$^{72}$, —OCX$^{72}_3$, —OCH$_2$X$^{72}$, —OCHX$^{72}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{73}$ is independently oxo, halogen, —CX$^{73}_3$, —CHX$^{73}_2$, —CH$_2$X$^{73}$, —OCX$^{73}_3$, —OCH$_2$X$^{73}$, —OCHX$^{73}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{74}$-substituted or unsubstituted alkyl (e.g., C$_1$-C$_8$, C$_1$-C$_6$, C$_1$-C$_4$, or C$_1$-C$_2$), R$^{74}$-substituted or unsubstituted heteroalkyl (e.g., 2 to 8 membered, 2 to 6 membered, 4 to 6 membered, 2 to 3 membered, or 4 to 5 membered), R$^{74}$-substituted or unsubstituted cycloalkyl (e.g., C$_3$-C$_8$, C$_3$-C$_6$, C$_4$-C$_6$, or C$_5$-C$_6$), R$^{74}$-substituted or unsubstituted heterocycloalkyl (e.g., 3 to 6 membered, 4 to 6 membered, 4 to 5 membered, or 5 to 6 membered), R$^{74}$-substituted or unsubstituted aryl (e.g., C$_6$-C$_{10}$ or phenyl), or R$^{74}$-substituted or unsubstituted heteroaryl (e.g., 5 to 10 membered, 5 to 9 membered, or 5 to 6 membered). X$^{73}$ is independently —F, —Cl, —Br, or —I. In embodiments, X$^{73}$ is —F. In embodiments, R$^{73}$ is independently oxo, halogen, —CX$^{73}_3$, —CHX$^{73}_2$, —CH$_2$X$^{73}$, —OCX$^{73}_3$, —OCH$_2$X$^{73}$, —OCHX$^{73}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{74}$ is independently oxo, halogen, —CX$^{74}_3$, —CHX$^{74}_2$, —CH$_2$X$^{74}$, —OCX$^{74}_3$, —OCH$_2$X$^{74}$, —OCHX$^{74}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{74}$ is independently —F, —Cl, —Br, or —I. In embodiments, $X^{74}$ is —F.

In embodiments, $R^{16}$ is independently hydrogen, oxo, halogen, —$CX^{16}_3$, —$CHX^{16}_2$, —$CH_2X^{16}$, —$OCX^{16}_3$, —$OCH_2X^{16}$, —$OCHX^{16}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{75}$-substituted or unsubstituted alkyl (e.g., $C_1$-$C_8$, $C_1$-$C_6$, $C_1$-$C_4$, or $C_1$-$C_2$), $R^{75}$-substituted or unsubstituted heteroalkyl (e.g., 2 to 8 membered, 2 to 6 membered, 4 to 6 membered, 2 to 3 membered, or 4 to 5 membered), $R^{75}$-substituted or unsubstituted cycloalkyl (e.g., $C_3$-$C_8$, $C_3$-$C_6$, $C_4$-$C_6$, or $C_5$-$C_6$), $R^{75}$-substituted or unsubstituted heterocycloalkyl (e.g., 3 to 6 membered, 4 to 5 membered, or 5 to 6 membered), $R^{75}$-substituted or unsubstituted aryl (e.g., $C_6$-$C_{10}$ or phenyl), or $R^{75}$-substituted or unsubstituted heteroaryl (e.g., 5 to 10 membered, 5 to 9 membered, or 5 to 6 membered). $X^{16}$ is independently —F, —Cl, —Br, or —I. In embodiments, $X^{16}$ is —F. In embodiments, $R^{16}$ is independently hydrogen. In embodiments, $R^{16}$ is independently unsubstituted methyl. In embodiments, $R^{16}$ is independently unsubstituted ethyl. In embodiments, $R^{16}$ is independently hydrogen, oxo, halogen, —$CX^{16}_3$, —$CHX^{16}_2$, —$CH_2X^{16}$, —$OCX^{16}_3$, —$OCH_2X^{16}$, —$OCHX^{16}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{75}$ is independently oxo, halogen, —$CX^{75}_3$, —$CHX^{75}_2$, —$CH_2X^{75}$, —$OCX^{75}_3$, —$OCH_2X^{75}$, —$OCHX^{75}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{76}$-substituted or unsubstituted alkyl (e.g., $C_1$-$C_8$, $C_1$-$C_6$, $C_1$-$C_4$, or $C_1$-$C_2$), $R^{76}$-substituted or unsubstituted heteroalkyl (e.g., 2 to 8 membered, 2 to 6 membered, 4 to 6 membered, 2 to 3 membered, or 4 to 5 membered), $R^{76}$-substituted or unsubstituted cycloalkyl (e.g., $C_3$-$C_8$, $C_3$-$C_6$, $C_4$-$C_6$, or $C_5$-$C_6$), $R^{76}$-substituted or unsubstituted heterocycloalkyl (e.g., 3 to 6 membered, 4 to 6 membered, 4 to 5 membered, or 5 to 6 membered), $R^{76}$-substituted or unsubstituted aryl (e.g., $C_6$-$C_{10}$ or phenyl), or $R^{76}$-substituted or unsubstituted heteroaryl (e.g., 5 to 10 membered, 5 to 9 membered, or 5 to 6 membered). $X^{75}$ is independently —F, —Cl, —Br, or —I. In embodiments, $X^{75}$ is —F. In embodiments, $R^{75}$ is independently oxo, halogen, —$CX^{75}_3$, —$CHX^{75}_2$, —$CH_2X^{75}$, —$OCX^{75}_3$, —$OCH_2X^{75}$, —$OCHX^{75}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{76}$ is independently oxo, halogen, —$CX^{76}_3$, —$CHX^{76}_2$, —$CH_2X^{76}$, —$OCX^{76}_3$, —$OCH_2X^{76}$, —$OCHX^{76}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{77}$-substituted or unsubstituted alkyl (e.g., $C_1$-$C_8$, $C_1$-$C_6$, $C_1$-$C_4$, or $C_1$-$C_2$), $R^{77}$-substituted or unsubstituted heteroalkyl (e.g., 2 to 8 membered, 2 to 6 membered, 4 to 6 membered, 2 to 3 membered, or 4 to 5 membered), $R^{77}$-substituted or unsubstituted cycloalkyl (e.g., $C_3$-$C_8$, $C_3$-$C_6$, $C_4$-$C_6$, or $C_5$-$C_6$), $R^{77}$-substituted or unsubstituted heterocycloalkyl (e.g., 3 to 6 membered, 4 to 6 membered, 4 to 5 membered, or 5 to 6 membered), $R^{77}$-substituted or unsubstituted aryl (e.g., $C_6$-$C_{10}$ or phenyl), or $R^{77}$-substituted or unsubstituted heteroaryl (e.g., 5 to 10 membered, 5 to 9 membered, or 5 to 6 membered). $X^{76}$ is independently —F, —Cl, —Br, or —I. In embodiments, $X^{76}$ is —F. In embodiments, $R^{76}$ is independently oxo, halogen, —$CX^{76}_3$, —$CHX^{76}_2$, —$CH_2X^{76}$, —$OCX^{76}_3$, —$OCH_2X^{76}$, —$OCHX^{76}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{77}$ is independently oxo, halogen, —$CX^{77}_3$, —$CHX^{77}_2$, —$CH_2X^{77}$, —$OCX^{77}_3$, —$OCH_2X^{77}$, —$OCHX^{77}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77}$ is independently —F, —Cl, —Br, or —I. In embodiments, $X^{77}$ is —F.

In embodiments, $R^{17}$ is independently hydrogen, oxo, halogen, —$CX^{17}_3$, —$CHX^{17}_2$, —$CH_2X^{17}$, —$OCX^{17}_3$, —$OCH_2X^{17}$, —$OCHX^{17}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)

NH$_2$, —NHSO$_2$H, —NHC=(O)H, —NHC(O)—OH, —NHOH, R$^{78}$-substituted or unsubstituted alkyl (e.g., C$_1$-C$_8$, C$_1$-C$_6$, C$_1$-C$_4$, or C$_1$-C$_2$), R$^{78}$-substituted or unsubstituted heteroalkyl (e.g., 2 to 8 membered, 2 to 6 membered, 4 to 6 membered, 2 to 3 membered, or 4 to 5 membered), R$^{78}$-substituted or unsubstituted cycloalkyl (e.g., C$_3$-C$_8$, C$_3$-C$_6$, C$_4$-C$_6$, or C$_5$-C$_6$), R$^{78}$-substituted or unsubstituted heterocycloalkyl (e.g., 3 to 6 membered, 4 to 6 membered, 4 to 5 membered, or 5 to 6 membered), R$^{78}$-substituted or unsubstituted aryl (e.g., C$_6$-C$_{10}$ or phenyl), or R$^{78}$-substituted or unsubstituted heteroaryl (e.g., 5 to 10 membered, 5 to 9 membered, or 5 to 6 membered). X$^{17}$ is independently —F, —Cl, —Br, or —I. In embodiments, X$^{17}$ is —F. In embodiments, R$^{17}$ is independently hydrogen. In embodiments, R$^{17}$ is independently unsubstituted methyl. In embodiments, R$^{17}$ is independently unsubstituted ethyl. In embodiments, R$^{17}$ is independently hydrogen, oxo, halogen, —CX$^{17}_3$, —CHX$^{17}_2$, —CH$_2$X$^{17}$, —OCX$^{17}_3$, —OCH$_2$X$^{17}$, —OCHX$^{17}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{78}$ is independently oxo, halogen, —CX$^{78}_3$, —CHX$^{78}_2$, —CH$_2$X$^{78}$, —OCX$^{78}_3$, —OCH$_2$X$^{78}$, —OCHX$^{78}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{79}$-substituted or unsubstituted alkyl (e.g., C$_1$-C$_8$, C$_1$-C$_6$, C$_1$-C$_4$, or C$_1$-C$_2$), R$^{79}$-substituted or unsubstituted heteroalkyl (e.g., 2 to 8 membered, 2 to 6 membered, 4 to 6 membered, 2 to 3 membered, or 4 to 5 membered), R$^{79}$-substituted or unsubstituted cycloalkyl (e.g., C$_3$-C$_8$, C$_3$-C$_6$, C$_4$-C$_6$, or C$_5$-C$_6$), R$^{79}$-substituted or unsubstituted heterocycloalkyl (e.g., 3 to 6 membered, 4 to 6 membered, 4 to 5 membered, or 5 to 6 membered), R$^{79}$-substituted or unsubstituted aryl (e.g., C$_6$-C$_{10}$ or phenyl), or R$^{79}$-substituted or unsubstituted heteroaryl (e.g., 5 to 10 membered, 5 to 9 membered, or 5 to 6 membered). X$^{78}$ is independently —F, —Cl, —Br, or —I. In embodiments, X$^{78}$ is —F. In embodiments, R$^{78}$ is independently oxo, halogen, —CX$^{78}_3$, —CHX$^{78}_2$, —CH$_2$X$^{78}$, —OCX$^{78}_3$, —OCH$_2$X$^{78}$, —OCHX$^{78}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{79}$ is independently oxo, halogen, —CX$^{79}_3$, —CHX$^{79}_2$, —CH$_2$X$^{79}$, —OCX$^{79}_3$, —OCH$_2$X$^{79}$, —OCHX$^{79}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{80}$-substituted or unsubstituted alkyl (e.g., C$_1$-C$_8$, C$_1$-C$_6$, C$_1$-C$_4$, or C$_1$-C$_2$), R$^{80}$-substituted or unsubstituted heteroalkyl (e.g., 2 to 8 membered, 2 to 6 membered, 4 to 6 membered, 2 to 3 membered, or 4 to 5 membered), R$^{80}$-substituted or unsubstituted cycloalkyl (e.g., C$_3$-C$_8$, C$_3$-C$_6$, C$_4$-C$_6$, or C$_5$-C$_6$), R$^{80}$-substituted or unsubstituted heterocycloalkyl (e.g., 3 to 6 membered, 4 to 6 membered, 4 to 5 membered, or 5 to 6 membered), R$^{80}$-substituted or unsubstituted aryl (e.g., C$_6$-C$_{10}$ or phenyl), or R$^{80}$-substituted or unsubstituted heteroaryl (e.g., 5 to 10 membered, 5 to 9 membered, or 5 to 6 membered). X$^{79}$ is independently —F, —Cl, —Br, or —I. In embodiments, X$^{79}$ is —F. In embodiments, R$^{79}$ is independently oxo, halogen, —CX$^{79}_3$, —CHX$^{79}_2$, —CH$_2$X$^{79}$, —OCX$^{79}_3$, —OCH$_2$X$^{79}$, —OCHX$^{79}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{80}$ is independently oxo, halogen, —CX$^{80}_3$, —CHX$^{80}_2$, —CH$_2$X$^{80}$, —OCX$^{80}_3$, —OCH$_2$X$^{80}$, —OCHX$^{80}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{80}$ is independently —F, —Cl, —Br, or —I. In embodiments, X$^{80}$ is —F.

In embodiments, R$^{18}$ is independently hydrogen, oxo, halogen, —CX$^{18}_3$, —CHX$^{18}_2$, —CH$_2$X$^{18}$, —OCX$^{18}_3$, —OCH$_2$X$^{18}$, —OCHX$^{18}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{81}$-substituted or unsubstituted alkyl (e.g., C$_1$-C$_8$, C$_1$-C$_6$, C$_1$-C$_4$, or C$_1$-C$_2$), R$^{81}$-substituted or unsubstituted heteroalkyl (e.g., 2 to 8 membered, 2 to 6 membered, 4 to 6 membered, 2 to 3 membered, or 4 to 5 membered), R$^{81}$-substituted or unsubstituted cycloalkyl (e.g., C$_3$-C$_8$, C$_3$-C$_6$, C$_4$-C$_6$, or C$_5$-C$_6$), R$^{81}$-substituted or unsubstituted heterocycloalkyl (e.g., 3 to 6 membered, 4 to 6 membered, 4 to 5 membered, or 5 to 6 membered), R$^{81}$-substituted or unsubstituted aryl (e.g., C$_6$-C$_{10}$ or phenyl), or R$^{81}$-substituted or unsubstituted heteroaryl (e.g., 5 to 10 membered, 5 to 9 membered, or 5 to 6 membered). X$^{18}$ is independently —F, —Cl, —Br, or —I. In embodiments, X$^{18}$ is —F. In embodiments, R$^{18}$ is independently hydrogen. In embodiments, R$^{18}$ is independently unsubstituted methyl. In embodiments, R$^{18}$ is independently unsubstituted ethyl. In embodiments, $R^{18}$ is independently hydrogen, oxo, halogen, —$CX^{18}_3$, —$CHX^{18}_2$, —$CH_2X^{18}$, —$OCX^{18}_3$, —$OCH_2X^{18}$, —$OCHX^{18}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{81}$ is independently oxo, halogen, —$CX^{81}_3$, —$CHX^{81}_2$, —$CH_2X^{81}$, —$OCX^{81}_3$, —$OCH_2X^{81}$, —$OCHX^{81}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, $R^{82}$-substituted or unsubstituted alkyl (e.g., $C_1$-$C_8$, $C_1$-$C_6$, $C_1$-$C_4$, or $C_1$-$C_2$), $R^{82}$-substituted or unsubstituted heteroalkyl (e.g., 2 to 8 membered, 2 to 6 membered, 4 to 6 membered, 2 to 3 membered, or 4 to 5 membered), $R^{82}$-substituted or unsubstituted cycloalkyl (e.g., $C_3$-$C_8$, $C_3$-$C_6$, $C_4$-$C_6$, or $C_5$-$C_6$), $R^{82}$-substituted or unsubstituted heterocycloalkyl (e.g., 3 to 6 membered, 4 to 6 membered, 4 to 5 membered, or 5 to 6 membered), $R^{82}$-substituted or unsubstituted aryl (e.g., $C_6$-$C_{10}$ or phenyl), or $R^{82}$-substituted or unsubstituted heteroaryl (e.g., 5 to 10 membered, 5 to 9 membered, or 5 to 6 membered). $X^{81}$ is independently —F, —Cl, —Br, or —I. In embodiments, $X^{81}$ is —F. In embodiments, $R^{81}$ is independently oxo, halogen, —$CX^{81}_3$, —$CHX^{81}_2$, —$CH_2X^{81}$, —$OCX^{81}_3$, —$OCH_2^{81}$, —$OCHX^{81}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{82}$ is independently oxo, halogen, —$CX^{82}_3$, —$CHX^{82}_2$, —$CH_2X^{82}$, —$OCX^{82}_3$, —$OCH_2X^{82}$, —$OCHX^{82}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, $R^{83}$-substituted or unsubstituted alkyl (e.g., $C_1$-$C_8$, $C_1$-$C_6$, $C_1$-$C_4$, or $C_1$-$C_2$), $R^{83}$-substituted or unsubstituted heteroalkyl (e.g., 2 to 8 membered, 2 to 6 membered, 4 to 6 membered, 2 to 3 membered, or 4 to 5 membered), $R^{83}$-substituted or unsubstituted cycloalkyl (e.g., $C_3$-$C_8$, $C_3$-$C_6$, $C_4$-$C_6$, or $C_5$-$C_6$), $R^{83}$-substituted or unsubstituted heterocycloalkyl (e.g., 3 to 6 membered, 4 to 6 membered, 4 to 5 membered, or 5 to 6 membered), $R^{83}$-substituted or unsubstituted aryl (e.g., $C_6$-$C_{10}$ or phenyl), or $R^{83}$-substituted or unsubstituted heteroaryl (e.g., 5 to 10 membered, 5 to 9 membered, or 5 to 6 membered). $X^{82}$ is independently —F, —Cl, —Br, or —I. In embodiments, $X^{82}$ is —F. In embodiments, $R^{82}$ is independently oxo, halogen, —$CX^{82}_3$, —$CHX^{82}_2$, —$CH_2X^{82}$, —$OCX^{82}_3$, —$OCH_2X^{82}$, —$OCHX^{82}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{83}$ is independently oxo, halogen, —$CX^{83}_3$, —$CHX^{83}_2$, —$CH_2X^{83}$, —$OCX^{83}_3$, —$OCH_2X^{83}$, —$OCHX^{83}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{83}$ is independently —F, —Cl, —Br, or —I. In embodiments, $X^{83}$ is —F.

In embodiments, $R^{19}$ is independently hydrogen, oxo, halogen, —$CX^{19}_3$, —$CHX^{19}_2$, —$CH_2X^{19}$, —$OCX^{19}_3$, —$OCH_2X^{19}$, —$OCHX^{19}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, $R^{84}$-substituted or unsubstituted alkyl (e.g., $C_1$-$C_8$, $C_1$-$C_6$, $C_1$-$C_4$, or $C_1$-$C_2$), $R^{84}$-substituted or unsubstituted heteroalkyl (e.g., 2 to 8 membered, 2 to 6 membered, 4 to 6 membered, 2 to 3 membered, or 4 to 5 membered), $R^{84}$-substituted or unsubstituted cycloalkyl (e.g., $C_3$-$C_8$, $C_3$-$C_6$, $C_4$-$C_6$, or $C_5$-$C_6$), $R^{84}$-substituted or unsubstituted heterocycloalkyl (e.g., 3 to 6 membered, 4 to 6 membered, 4 to 5 membered, or 5 to 6 membered), $R^{84}$-substituted or unsubstituted aryl (e.g., $C_6$-$C_{10}$ or phenyl), or $R^{84}$-substituted or unsubstituted heteroaryl (e.g., 5 to 10 membered, 5 to 9 membered, or 5 to 6 membered). $X^{19}$ is independently —F, —Cl, —Br, or —I. In embodiments, $X^{19}$ is —F. In embodiments, $R^{19}$ is independently hydrogen. In embodiments, $R^{19}$ is independently unsubstituted methyl. In embodiments, $R^{19}$ is independently unsubstituted ethyl. In embodiments, $R^{19}$ is independently hydrogen, oxo, halogen, —$CX^{19}_3$, —$CHX^{19}_2$, —$CH_2X^{19}$, —$OCX^{19}_3$, —$OCH_2X^{19}$, —$OCHX^{19}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{84}$ is independently oxo, halogen, —$CX^{84}_3$, —$CHX^{84}_2$, —$CH_2X^{84}$, —$OCX^{84}_3$, —$OCH_2X^{84}$, —$OCHX^{84}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{85}$-substituted or unsubstituted alkyl (e.g., C$_1$-C$_8$, C$_1$-C$_6$, C$_1$-C$_4$, or C$_1$-C$_2$), R$^{85}$-substituted or unsubstituted heteroalkyl (e.g., 2 to 8 membered, 2 to 6 membered, 4 to 6 membered, 2 to 3 membered, or 4 to 5 membered), R$^{85}$-substituted or unsubstituted cycloalkyl (e.g., C$_3$-C$_8$, C$_3$-C$_6$, C$_4$-C$_6$, or C$_5$-C$_6$), R$^{85}$-substituted or unsubstituted heterocycloalkyl (e.g., 3 to 6 membered, 4 to 6 membered, 4 to 5 membered, or 5 to 6 membered), R$^{85}$-substituted or unsubstituted aryl (e.g., C$_6$-C$_{10}$ or phenyl), or R$^{85}$-substituted or unsubstituted heteroaryl (e.g., 5 to 10 membered, 5 to 9 membered, or 5 to 6 membered). X$^{84}$ is independently —F, —Cl, —Br, or —I. In embodiments, X$^{84}$ is —F. In embodiments, R$^{84}$ is independently oxo, halogen, —CX$^{84}_3$, —CHX$^{84}_2$, —CH$_2$X$^{84}$, —OCX$^{84}_3$, —OCH$_2$X$^{84}$, —OCHX$^{84}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{85}$ is independently oxo, halogen, —CX$^{85}_3$, —CHX$^{85}_2$, —CH$_2$X$^{85}$, —OCX$^{85}_3$, —OCH$_2$X$^{85}$, —OCHX$^{85}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{86}$-substituted or unsubstituted alkyl (e.g., C$_1$-C$_8$, C$_1$-C$_6$, C$_1$-C$_4$, or C$_1$-C$_2$), R$^{86}$-substituted or unsubstituted heteroalkyl (e.g., 2 to 8 membered, 2 to 6 membered, 4 to 6 membered, 2 to 3 membered, or 4 to 5 membered), R$^{86}$-substituted or unsubstituted cycloalkyl (e.g., C$_3$-C$_8$, C$_3$-C$_6$, C$_4$-C$_6$, or C$_5$-C$_6$), R$^{86}$-substituted or unsubstituted heterocycloalkyl (e.g., 3 to 6 membered, 4 to 6 membered, 4 to 5 membered, or 5 to 6 membered), R$^{86}$-substituted or unsubstituted aryl (e.g., C$_6$-C$_{10}$ or phenyl), or R$^{86}$-substituted or unsubstituted heteroaryl (e.g., 5 to 10 membered, 5 to 9 membered, or 5 to 6 membered). X$^{85}$ is independently —F, —Cl, —Br, or —I. In embodiments, X$^{85}$ is —F. In embodiments, R$^{85}$ is independently oxo, halogen, —CX$^{85}_3$, —CHX$^{85}_2$, —CH$_2$X$^{85}$, —OCX$^{85}_3$, —OCH$_2$X$^{85}$, —OCHX$^{85}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{86}$ is independently oxo, halogen, —CX$^{86}_3$, —CHX$^{86}_2$, —CH$_2$X$^{86}$, —OCX$^{86}_3$, —OCH$_2$X$^{86}$, —OCHX$^{86}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or heteroaryl (e.g., 5 to 10 membered, 5 to 9 membered, or 5 to 6 membered). X$^{86}$ is independently —F, —Cl, —Br, or —I. In embodiments, X$^{86}$ is —F.

L$^1$ is independently a bond, R$^{96}$-substituted or unsubstituted alkylene (e.g., C$_1$-C$_8$, C$_1$-C$_6$, C$_1$-C$_4$, C$_1$-C$_3$, C$_2$-C$_4$, or C$_1$-C$_2$), R$^{96}$-substituted or unsubstituted alkenylene (e.g., C$_2$-C$_8$, C$_2$-C$_6$, C$_2$-C$_4$, or C$_2$-C$_3$), R$^{96}$-substituted or unsubstituted alkynylene (e.g., C$_2$-C$_8$, C$_2$-C$_6$, C$_2$-C$_4$, or C$_2$-C$_3$), R$^{96}$-substituted or unsubstituted heteroalkylene (e.g., 2 to 8 membered, 2 to 6 membered, 2 to 4 membered, or 2 to 3 membered), R$^{96}$-substituted or unsubstituted heteroalkenylene (e.g., 3 to 8 membered, 3 to 6 membered, or 3 to 4 membered), or R$^{96}$-substituted or unsubstituted heteroalkynylene (e.g., 3 to 8 membered, 3 to 6 membered, or 3 to 4 membered). In embodiments, L$^1$ is independently a bond, unsubstituted alkylene (e.g., C$_1$-C$_8$, C$_1$-C$_6$, C$_1$-C$_4$, C$_1$-C$_3$, C$_2$-C$_4$, or C$_1$-C$_2$), unsubstituted alkenylene (e.g., C$_2$-C$_8$, C$_2$-C$_6$, C$_2$-C$_4$, or C$_2$-C$_3$), unsubstituted alkynylene (e.g., C$_2$-C$_8$, C$_2$-C$_6$, C$_2$-C$_4$, or C$_2$-C$_3$), unsubstituted heteroalkylene (e.g., 2 to 8 membered, 2 to 6 membered, 2 to 4 membered, or 2 to 3 membered), unsubstituted heteroalkenylene (e.g., 3 to 8 membered, 3 to 6 membered, or 3 to 4 membered), or unsubstituted heteroalkynylene (e.g., 3 to 8 membered, 3 to 6 membered, or 3 to 4 membered).

R$^{96}$ is independently oxo, halogen, —CX$^{96}_3$, —CHX$^{96}_2$, —CH$_2$X$^{96}$, —OCX$^{96}_3$, —OCH$_2$X$^{96}$, —OCHX$^{96}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{97}$-substituted or unsubstituted alkyl (e.g., C$_1$-C$_8$, C$_1$-C$_6$, C$_1$-C$_4$, or C$_1$-C$_2$), R$^{97}$-substituted or unsubstituted heteroalkyl (e.g., 2 to 8 membered, 2 to 6 membered, 4 to 6 membered, 2 to 3 membered, or 4 to 5 membered), R$^{97}$-substituted or unsubstituted cycloalkyl (e.g., C$_3$-C$_8$, C$_3$-C$_6$, C$_4$-C$_6$, or C$_5$-C$_6$), R$^{97}$-substituted or unsubstituted heterocycloalkyl (e.g., 3 to 6 membered, 4 to 6 membered, 4 to 5 membered, or 5 to 6 membered), R$^{97}$-substituted or unsubstituted aryl (e.g., C$_6$-C$_{10}$ or phenyl), or R$^{97}$-substituted or unsubstituted heteroaryl (e.g., 5 to 10 membered, 5 to 9 membered, or 5 to 6 membered). X$^{96}$ is independently —F, —Cl, —Br, or —I. In embodiments, X$^{96}$ is —F. In embodiments, R$^{96}$ is independently oxo, halogen, —CX$^{96}_3$, —CHX$^{96}_2$, —CH$_2$X$^{96}$, —OCX$^{96}_3$, —OCH$_2$X$^{96}$, —OCHX$^{96}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

$R^{97}$ is independently oxo, halogen, —$CX^{97}_3$, —$CHX^{97}_2$, —$CH_2X^{97}$, —$OCX^{97}_3$, —$OCH_2X^{97}$, —$OCHX^{97}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{98}$-substituted or unsubstituted alkyl (e.g., $C_1$-$C_8$, $C_1$-$C_6$, $C_1$-$C_4$, or $C_1$-$C_2$), $R^{98}$-substituted or unsubstituted heteroalkyl (e.g., 2 to 8 membered, 2 to 6 membered, 4 to 6 membered, 2 to 3 membered, or 4 to 5 membered), $R^{98}$-substituted or unsubstituted cycloalkyl (e.g., $C_3$-$C_8$, $C_3$-$C_6$, $C_4$-$C_6$, or $C_5$-$C_6$), $R^{98}$-substituted or unsubstituted heterocycloalkyl (e.g., 3 to 6 membered, 4 to 6 membered, 4 to 5 membered, or 5 to 6 membered), $R^{98}$-substituted or unsubstituted aryl (e.g., $C_6$-$C_{10}$ or phenyl), or $R^{98}$-substituted or unsubstituted heteroaryl (e.g., 5 to 10 membered, 5 to 9 membered, or 5 to 6 membered). $X^{97}$ is independently —F, —Cl, —Br, or —I. In embodiments, $X^{97}$ is —F. In embodiments, $R^{97}$ is independently oxo, halogen, —$CX^{97}_3$, —$CHX^{97}_2$, —$CH_2X^{97}$, —$OCX^{97}_3$, —$OCH_2X^{97}$, —$OCHX^{97}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{98}$ is independently oxo, halogen, —$CX^{98}_3$, —$CHX^{98}_2$, —$CH_2X^{98}$, —$OCX^{98}_3$, —$OCH_2X^{98}$, —$OCHX^{98}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{98}$ is independently —F, —Cl, —Br, or —I. In embodiments, $X^{98}$ is —F.

In an aspect is provided an AR inhibitor (e.g., a compound described herein above), or a pharmaceutically acceptable salt thereof. In embodiments, the AR inhibitor contacts the AR DNA binding domain (DBD). In embodiments, the AR inhibitor binds to the AR DBD. In embodiments, the AR inhibitor binds the AR DBD K609 (e.g. amino acid number in SEQ ID NO:1). In embodiments, the AR inhibitor binds the AR DBD P612 (e.g. amino acid number in SEQ ID NO:1). In embodiments, the AR inhibitor binds the AR DBD but does not bind AR DBD N610 (e.g, amino acid number in SEQ ID NO:1). In embodiments, the AR inhibitor binds the AR DBD and DNA. In embodiments, the AR inhibitor binds an AR DBD-DNA complex. In embodiments, the AR inhibitor binds the AR DBD and the minor groove of DNA. In embodiments, the AR inhibitor simultaneously binds two AR DBDs. In embodiments, the AR inhibitor simultaneously binds two AR DBDs and DNA. In embodiments, the AR inhibitor has a solubility of at least 1 mg/mL (e.g., at least 1, 2, 3, 4, 5, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/mL; about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/mL) in aquaeous solution (e.g., at room temperature, about 21 to 25 degrees C., about 21 degrees C., about 22 degrees C., about 23 degrees C., about 24 degrees C., about 25 degrees C., 21 to 25 degrees C., 21 degrees C., 22 degrees C., 23 degrees C., 24 degrees C., 25 degrees C., physiological temperature, about 37 degrees C., or 37 degrees C.). In embodiments, the AR inhibitor has a solubility of at least 1 mg/mL (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/mL; about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/mL) in beta cyclodextrin (e.g., at room temperature, about 21 to 25 degrees C., about 21 degrees C., about 22 degrees C., about 23 degrees C., about 24 degrees C., about 25 degrees C., 21 to 25 degrees C., 21 degrees C., 22 degrees C., 23 degrees C., 24 degrees C., 25 degrees C., physiological temperature, about 37 degrees C., or 37 degrees C.). In embodiments, the AR inhibitor has a bioavailability (e.g., amount in circulating blood, concentration in circulating blood) when orally administered of at least 1% (w/v) (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% (w/v); about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% (w/v)) of the bioavailability when administered by injection (e.g., intravenous administration) (e.g., identical amounts of AR inhibitor administered orally and by injection (e.g., intravenous), for example when the AR inhibitor is suspended or dissolved in cyclodextrin (e.g., at room temperature, about 21 to 25 degrees C., about 21 degrees C., about 22 degrees C., about 23 degrees C., about 24 degrees C., about 25 degrees C., 21 to 25 degrees C., 21 degrees C., 22 degrees C., 23 degrees C., 24 degrees C., 25 degrees C., physiological temperature, about 37 degrees C., or 37 degrees C.). In embodiments, the bioavailability is measured at least 30 minutes after administration (e.g., oral) (e.g., after at least 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes; after at least 1, 2, 3, 4, 5, 6, 7, 8, 9, 10, 11, 1.2, 13, 14, 15, 16, 17, 18, 19, 20, 21, 22, 23, 24, 25, 26, 27, 28, 29, 30, 31, 32, 33, 34, 35, or 36 hours; after about 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes; after about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 hours; after 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes; after 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 hours, all following administration (e.g., orally)).

In embodiments, the AR inhibitor binds the AR DBD (e.g., at K609 and/or P612, numbering from SEC ID NO:1) and has a solubility of at least 1 mg/mL (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/mL; about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/mL) in beta cyclodextrin (e.g., at room temperature, about 21 to 25 degrees C., about 21 degrees C., about 22 degrees C., about 23 degrees C., about 24 degrees C., about 25 degrees C., 21 to 25 degrees C., 21 degrees C., 22 degrees C., 23 degrees C., 24 degrees C., 25 degrees C., physiological temperature, about 37 degrees C., or 37 degrees C.) and has a bioavailability (e.g., amount in circulating blood, concentration in circulating blood) when orally administered of at least 1% (w/v) (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% (w/v); about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% (w/v)) of the bioavailability when administered by injection (e.g., intravenous administration) (e.g., identical amounts of AR inhibitor administered orally and by injection (e.g., intravenous), wherein the bioavailability is measured at least 30 minutes after administration (e.g., oral) (e.g., after at least 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes; after at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 hours; after about 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes; after about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 hours; after 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes; after 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 hours, all following administration (e.g., orally)).

In some embodiments, the compound is any one of the compounds described herein (e.g., in an aspect, embodiment, claim, figure, table, or example). In embodiments, the compound is soluble in hydroxypropyl beta cyclodextrin. In embodiments, the compound is more soluble in an administration solvent (e.g., betacyclodextrin) than pyrvinium (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 5000, 10000, 50000, 100000-fold more soluble).

In embodiments, the pharmaceutically acceptable salt of a compound (e.g., described herein, AR inhibitor) is a salt of the compound and palmoic acid or pamoate. In embodiments, the pharmaceutically acceptable salt of a compound (e.g., described herein, AR inhibitor) is a salt of the compound and Cl—. In embodiments, the pharmaceutically acceptable salt of a compound (e.g., described herein, AR inhibitor) is a salt of the compound and a halide. In embodiments, the pharmaceutically acceptable salt of a compound (e.g., described herein, AR inhibitor) is a salt of the compound and triflate. In embodiments, the pharmaceutically acceptable salt of a compound (e.g., described herein, AR inhibitor) is a salt of the compound and tosylate. In embodiments, the pharmaceutically acceptable salt of a compound (e.g., described herein, AR inhibitor) is a salt of the compound and pamoate.

In some embodiments, a compound as described herein may include multiple instances of $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and/or other variables. In such embodiments, each variable may optional be different and be appropriately labeled to distinguish each group for greater clarity. For example, where each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and/or $R^{19}$ is different, they may be referred to, for example, as $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$, $R^{10.1}$, $R^{10.2}$, $R^{10.3}$, $R^{10.4}$, $R^{10.5}$$R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$, $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$, $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$, $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$, $R^{15.1}$, $R^{15.2}$, $R^{15.3}$, $R^{15.4}$, $R^{15.5}$, $R^{15.6}$, $R^{15.7}$, $R^{15.8}$, $R^{15.9}$, $R^{15.10}$, $R^{15.11}$, $R^{15.12}$, $R^{15.13}$, $R^{15.14}$, $R^{15.15}$, $R^{15.16}$, $R^{15.17}$, $R^{15.18}$, $R^{15.19}$, $R^{15.20}$, $R^{15.21}$, $R^{15.22}$, $R^{15.23}$, $R^{15.24}$, $R^{15.25}$, $R^{15.26}$, $R^{15.27}$, $R^{15.28}$, $R^{15.29}$, $R^{15.30}$, $R^{15.31}$, $R^{15.32}$, $R^{15.33}$, $R^{15.34}$, $R^{15.35}$, $R^{15.36}$, $R^{15.37}$, $R^{15.38}$, $R^{15.39}$, $R^{15.40}$, $R^{15.41}$, $R^{15.42}$, $R^{16.1}$, $R^{16.2}$, $R^{16.3}$, $R^{16.4}$, $R^{16.5}$, $R^{16.6}$, $R^{16.7}$, $R^{16.8}$, $R^{16.9}$, $R^{16.10}$, $R^{16.11}$, $R^{16.12}$, $R^{16.13}$, $R^{16.14}$, $R^{16.15}$, $R^{16.16}$, $R^{16.17}$, $R^{16.18}$, $R^{16.19}$, $R^{16.20}$, $R^{16.21}$, $R^{16.22}$, $R^{16.23}$, $R^{16.24}$, $R^{16.25}$, $R^{16.26}$, $R^{16.27}$, $R^{16.28}$, $R^{16.29}$, $R^{16.30}$, $R^{16.31}$, $R^{16.32}$, $R^{16.33}$, $R^{16.34}$, $R^{16.35}$, $R^{16.36}$, $R^{16.37}$, $R^{16.38}$, $R^{16.39}$, $R^{16.40}$, $R^{16.41}$, $R^{16.42}$, $R^{17.1}$, $R^{17.2}$, $R^{17.3}$, $R^{17.4}$, $R^{17.5}$, $R^{17.6}$, $R^{17.7}$, $R^{17.8}$, $R^{17.9}$, $R^{17.10}$, $R^{17.11}$, $R^{17.12}$, $R^{17.13}$, $R^{17.14}$, $R^{17.15}$, $R^{17.16}$, $R^{17.17}$, $R^{17.18}$, $R^{17.19}$, $R^{17.20}$, $R^{17.21}$, $R^{17.22}$, $R^{17.23}$, $R^{17.24}$, $R^{17.25}$, $R^{17.26}$, $R^{17.27}$, $R^{17.28}$, $R^{17.29}$, $R^{17.30}$, $R^{17.31}$, $R^{17.32}$, $R^{17.33}$, $R^{17.34}$, $R^{17.35}$, $R^{17.36}$, $R^{17.37}$, $R^{17.38}$, $R^{17.39}$, $R^{17.40}$, $R^{17.41}$, $R^{17.42}$, $R^{18.1}$, $R^{18.2}$, $R^{18.3}$, $R^{18.4}$, $R^{18.5}$, $R^{18.6}$, $R^{18.7}$, $R^{18.8}$, $R^{18.9}$, $R^{18.10}$, $R^{18.11}$, $R^{18.12}$, $R^{18.13}$, $R^{18.14}$, $R^{18.15}$, $R^{18.16}$, $R^{18.17}$, $R^{18.18}$, $R^{18.19}$, $R^{18.20}$, $R^{18.21}$, $R^{18.22}$, $R^{18.23}$, $R^{18.24}$, $R^{18.25}$, $R^{18.26}$, $R^{18.27}$, $R^{18.28}$, $R^{18.29}$, $R^{18.30}$, $R^{18.31}$, $R^{18.32}$, $R^{18.33}$, $R^{18.34}$, $R^{18.35}$, $R^{18.36}$, $R^{18.37}$, $R^{18.38}$, $R^{18.39}$, $R^{18.40}$, $R^{18.41}$, $R^{18.42}$, $R^{19.1}$, $R^{19.2}$, $R^{19.3}$, $R^{19.4}$, $R^{19.5}$, $R^{19.6}$, $R^{19.7}$, $R^{19.8}$, $R^{19.9}$, $R^{19.10}$, $R^{19.11}$, $R^{19.12}$, $R^{19.13}$, $R^{9.14}$, $R^{19.15}$, $R^{19.16}$, $R^{19.17}$, $R^{19.18}$, $R^{19.18}$, $R^{19.19}$, $R^{19.20}$, $R^{19.21}$, $R^{19.22}$, $R^{19.23}$, $R^{19.24}$, $R^{19.25}$, $R^{19.26}$, $R^{19.27}$, $R^{19.28}$, $R^{19.29}$, $R^{19.30}$, $R^{19.31}$, $R^{19.32}$, $R^{19.33}$, $R^{19.34}$, $R^{19.35}$, $R^{19.36}$, $R^{19.37}$, $R^{19.38}$, $R^{19.39}$, $R^{19.40}$, $R^{19.41}$, $R^{19.42}$, respectively, wherein the definition of $R^7$ is assumed by $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$; $R^8$ is assumed by $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$; $R^9$ is assumed by $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$; $R^{10}$ is assumed by $R^{10.1}$, $R^{10.2}$, $R^{10.3}$, $R^{10.4}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$; $R^{11}$ is assumed by $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$; $R^{12}$ is assumed by $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$; $R^{13}$ is assumed by $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$; $R^{14}$ is assumed by $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$; $R^{15}$ is assumed by $R^{15.1}$, $R^{15.2}$, $R^{15.3}$, $R^{15.4}$, $R^{15.5}$, $R^{15.6}$, $R^{15.7}$, $R^{15.8}$, $R^{15.9}$, $R^{15.10}$, $R^{15.11}$, $R^{15.12}$, $R^{15.13}$, $R^{15.14}$, $R^{15.15}$, $R^{15.16}$, $R^{15.17}$, $R^{15.18}$, $R^{15.19}$, $R^{15.20}$, $R^{15.21}$, $R^{15.22}$, $R^{15.23}$, $R^{15.24}$, $R^{15.25}$, $R^{15.26}$, $R^{15.27}$, $R^{15.28}$, $R^{15.29}$, $R^{15.30}$, $R^{15.31}$, $R^{15.32}$, $R^{15.33}$, $R^{15.34}$, $R^{15.35}$, $R^{15.36}$, $R^{15.37}$, $R^{15.38}$, $R^{15.39}$, $R^{15.40}$, $R^{15.41}$, $R^{15.42}$; $R^{16}$ is assumed by $R^{16.1}$, $R^{16.2}$, $R^{16.3}$, $R^{16.4}$, $R^{16.5}$, $R^{16.6}$, $R^{16.7}$, $R^{16.8}$, $R^{16.9}$, $R^{16.10}$, $R^{16.11}$, $R^{16.12}$, $R^{16.13}$, $R^{16.14}$, $R^{16.15}$, $R^{16.16}$, $R^{16.17}$, $R^{16.18}$, $R^{16.19}$, $R^{16.20}$, $R^{16.21}$, $R^{16.22}$, $R^{16.23}$, $R^{16.24}$, $R^{16.25}$, $R^{16.26}$, $R^{16.27}$, $R^{16.28}$, $R^{16.29}$, $R^{16.30}$, $R^{16.31}$, $R^{16.32}$, $R^{16.33}$, $R^{16.34}$, $R^{16.35}$, $R^{16.36}$, $R^{16.37}$, $R^{16.38}$, $R^{16.39}$, $R^{16.40}$, $R^{16.41}$, $R^{16.42}$; $R^{17}$ is assumed by $R^{17.1}$, $R^{17.2}$, $R^{17.3}$, $R^{17.4}$, $R^{17.5}$, $R^{17.6}$, $R^{17.7}$, $R^{17.8}$, $R^{17.9}$, $R^{17.10}$, $R^{17.11}$, $R^{17.12}$, $R^{17.13}$, $R^{17.14}$, $R^{17.15}$, $R^{17.16}$, $R^{17.17}$, $R^{17.18}$, $R^{17.19}$, $R^{17.20}$, $R^{17.21}$, $R^{17.22}$, $R^{17.23}$, $R^{17.24}$, $R^{17.25}$, $R^{17.26}$, $R^{17.27}$, $R^{17.28}$, $R^{17.29}$, $R^{17.30}$, $R^{17.31}$, $R^{17.32}$, $R^{17.33}$, $R^{17.34}$, $R^{17.35}$, $R^{17.36}$, $R^{17.37}$, $R^{17.38}$, $R^{17.39}$, $R^{17.40}$, $R^{17.41}$, $R^{17.42}$; $R^{18}$ is assumed by $R^{18.1}$, $R^{18.2}$, $R^{18.3}$, $R^{18.4}$, $R^{18.5}$, $R^{18.6}$, $R^{18.7}$, $R^{18.8}$, $R^{18.9}$, $R^{18.10}$, $R^{18.11}$, $R^{18.12}$, $R^{18.13}$, $R^{18.14}$, $R^{18.15}$, $R^{18.16}$, $R^{18.17}$, $R^{18.18}$, $R^{18.19}$, $R^{18.20}$, $R^{18.21}$, $R^{18.22}$, $R^{18.23}$, $R^{18.24}$, $R^{18.25}$, $R^{18.26}$, $R^{18.27}$, $R^{18.28}$, $R^{18.29}$, $R^{18.30}$, $R^{18.31}$, $R^{18.32}$, $R^{18.33}$, $R^{18.34}$, $R^{18.35}$, $R^{18.36}$, $R^{18.37}$, $R^{18.38}$, $R^{18.39}$, $R^{18.40}$, $R^{18.41}$, $R^{18.42}$; and/or $R^{19}$ is assumed by $R^{19.1}$, $R^{19.2}$, $R^{19.3}$, $R^{19.4}$, $R^{19.5}$, $R^{19.6}$, $R^{19.7}$, $R^{19.8}$, $R^{19.9}$, $R^{19.10}$, $R^{19.11}$, $R^{19.12}$, $R^{19.13}$, $R^{19.14}$, $R^{19.15}$, $R^{19.16}$, $R^{19.17}$, $R^{19.18}$, $R^{19.19}$, $R^{19.20}$, $R^{19.21}$, $R^{19.22}$, $R^{19.23}$, $R^{19.24}$, $R^{19.25}$, $R^{19.26}$, $R^{19.27}$, $R^{19.28}$, $R^{19.29}$, $R^{19.30}$, $R^{19.31}$, $R^{19.32}$, $R^{19.33}$, $R^{19.34}$, $R^{19.35}$, $R^{19.36}$, $R^{19.37}$, $R^{19.38}$, $R^{19.39}$, $R^{19.40}$, $R^{19.41}$, $R^{19.42}$. The variables used within a definition of $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

C. PHARMACEUTICAL COMPOSITIONS

In another aspect is provided a pharmaceutical composition including a pharmaceutically acceptable excipient and a compound, or pharmaceutically acceptable salt thereof, as described herein.

In embodiments of the pharmaceutical compositions, the compound, or pharmaceutically acceptable salt thereof, is included in a therapeutically effective amount.

In embodiments, the pharmaceutical composition includes a second agent (e.g. therapeutic agent). In embodiments, the pharmaceutical composition includes a second agent (e.g. therapeutic agent) in a therapeutically effective amount. In embodiments, the second agent is an agent for treating cancer (e.g. prostate cancer) or an aberrant level of androgen receptor activity or a disease associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism). In embodiments, the second agent is an anti-cancer agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that includes the hormone binding site. In embodiments, the second agent binds androgen receptor at the hormone binding site. In embodiments, the second agent binds the ligand binding domain. In embodiments, the second agent is flutamide. In embodiments, the second agent is bicalutamide. In embodiments, the second agent is nilutamide. In embodiments, the second agent is enzalutamide. In embodiments, the second agent is ARN-509. In embodiments, the second agent binds androgen receptor at a site that does not include the hormone binding site. In embodiments, the second agent binds androgen receptor at a site that is not the hormone binding site. In embodiments, the second agent does not bind the ligand binding domain. In embodiments, the second agent binds androgen receptor at a site that is different from the site bound by a compound described herein, including embodiments. In embodiments, the second agent binds androgen receptor at a site that does not overlap with the binding site of a compound described herein, including embodiments. In embodiments, the second agent is a luteinizing hormone-releasing hormone analogue (LHRH analogue or analog). In embodiments, the second agent is a luteinizing hormone-releasing hormone agonist. In embodiments, the second agent is a luteinizing hormone-releasing hormone analogue antagonist. In embodiments, the second agent is a gonadotropin-releasing hormone analogue (GnRH analogue or analog). In embodiments, the second agent is a gonadotropin-releasing hormone agonist. In embodiments, the second agent is a gonadotropin-releasing hormone analogue antagonist. In embodiments, the second agent is leuprolide, goserelin, triptorelin, hisrelin, degarelix, or abiraterone. A luteinizing hormone-releasing hormone analogue or gonadotropin-releasing hormone analogue is a composition (e.g., peptide) that interacts with (binds) the GnRH receptor and modulates the release of pituitary gonadotropins follicle-stimulating hormone and/or luteinizing hormone. In embodiments, the second agent is avorelin, buserelin, deslorelin, gonadorelin, goserelin, histrelin, leuprorelin, lutrelin, nafarelin, peforelin, or triptorelin. In embodiments, the second agent is abarelix, cetrorelix, degarelix, detirelix, ganirelix, iturelix, oxarelix, prazarelix, ramorelix, or teverelix. In embodiments, the second agent is casodex. In embodiments, the second agent is abiraterone. In embodiments, the second agent is abiraterone acetate. In embodiments, the second agent is an inhibitor of androgen synthesis. In embodiments, the second agent is an inhibitor of CYP17A1. In embodiments, the second agent is cyproterone acetate. In embodiments, the second agent is orteronel. In embodiments, the second agent is VT-464. In embodiments, the second agent is galeterone. In embodiments, the second agent is darolutamide. In embodiments, the second agent is ARN-509. In embodiments, the second agent is an androgen receptor ligand. In embodiments, the second agent is apalutamide. In embodiments, the second agent is cyproterone (e.g., cyproterone acetate). In embodiments, the second agent is megestrol (e.g., megestrol acetate). In embodiments, the second agent is chlormadinone (e.g., chlormadinone acetate). In embodiments, the second agent is spironolactone. In embodiments, the second agent is canrenone. In embodiments, the second agent is drospirenone. In embodiments, the second agent is ketoconazole. In embodiments, the second agent is topilutamide. In embodiments, the second agent is fluridil. In embodiments, the second agent is cimetidine. In embodiments, the second agent is danazol. In embodiments, the second agent is gestrinone. In embodiments, the second agent is abiraterone (e.g., abiraterone acetate). In embodiments, the second agent is an androgen synthesis inhibitor. In embodiments, the second agent is a 5α-reductase inhibitor (e.g., finasteride, dutasteride, alfatradiol, saw palmetto extract). In embodiments, the second agent is finasteride. In embodiments, the second agent is dutasteride. In embodiments, the second agent is alfatradio. In embodiments, the second agent is saw palmetto extract. In embodiments, the anti-androgen receptor agent is flutamide, nilutamide, bicalutamide, ARN-509, apalutamide, enzalutamide, darolutamide, cyproterone (e.g., cyproterone acetate), megestrol (e.g., megestrol acetate), chlormadinone (e.g., chlormadinone acetate), spironolactone, canrenone, drospirenone, ketoconazole, topilutamide, fluridil, cimetidine, gestrinone, or abiraterone (e.g., abiraterone acetate).

D. METHODS OF TREATMENT

In another aspect is provided a method of treating a nuclear receptor activity-associated disease in a subject in need of such treatment, the method including administering a compound, or a pharmaceutically acceptable salt thereof as described herein, including embodiments or in an example, table, figure, or claim.

In embodiments of the method, the compound, or pharmaceutically acceptable salt thereof, is included in an effective amount. In embodiments of the method, the compound, or pharmaceutically acceptable salt thereof, is included in a therapeutically effective amount. In embodiments of the method, the compound, or pharmaceutically acceptable salt thereof, is included in a prophylactically effective amount.

In embodiments, the method includes administering a second agent (e.g. therapeutic agent). In embodiments, the method includes administering a second agent (e.g. therapeutic agent) in a therapeutically effective amount. In embodiments of the methods, the second agent is an agent for treating cancer (e.g. prostate cancer) or an aberrant level of androgen receptor activity or a disease associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism). In embodiments, the second agent is an anti-cancer agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that includes the hormone binding site. In embodiments, the second agent binds androgen receptor at the hormone binding site. In embodiments, the second agent binds the ligand binding domain. In embodiments, the second agent is flutamide. In embodiments, the second agent is bicalutamide. In embodiments, the second agent is nilutamide. In embodiments, the second agent is enzalutamide. In embodiments, the second agent is ARN-509. In embodiments, the second agent binds androgen receptor at a site that does not include the hormone binding site. In embodiments, the second agent binds androgen receptor at a site that does is not the hormone binding site. In embodiments, the second agent does not bind the ligand binding domain. In embodiments, the second agent binds androgen receptor at a site that is different from the site bound by a compound described herein, including embodiments. In embodiments, the second agent binds androgen receptor at a site that does not overlap with the binding site of a compound described herein, including embodiments. In embodiments, the second agent is darolutamide. In embodiments, the second agent is ARN-509. In embodiments, the second agent is an androgen receptor ligand. In embodiments, the second agent is apalutamide. In embodiments, the second agent is cyproterone (e.g., cyproterone acetate). In embodiments, the second agent is megestrol (e.g., megestrol acetate). In embodiments, the second agent is chlormadinone (e.g., chlormadinone acetate). In embodiments, the second agent is spironolactone. In embodiments, the second agent is canrenone. In embodiments, the second agent is drospirenone. In embodiments, the second agent is ketoconazole. In embodiments, the second agent is topilutamide. In embodiments, the second agent is fluridil. In embodiments, the second agent is cimetidine. In embodiments, the second agent is danazol. In embodiments, the second agent is gestrinone. In embodiments, the second agent is abiraterone (e.g., abiraterone acetate). In embodiments, the second agent is an androgen synthesis inhibitor. In embodiments, the second agent is a 5α-reductase inhibitor (e.g., finasteride, dutasteride, alfatradiol, saw palmetto extract). In embodiments, the second agent is finasteride. In embodiments, the second agent is dutasteride. In embodiments, the second agent is alfatradio. In embodiments, the second agent is saw palmetto extract. In embodiments, the anti-androgen receptor agent is flutamide, nilutamide, bicalutamide, ARN-509, apalutamide, enzalutamide, darolutamide, cyproterone (e.g., cyproterone acetate), megestrol (e.g., megestrol acetate), chlormadinone (e.g., chlormadinone acetate), spironolactone, canrenone, drospirenone, ketoconazole, topilutamide, fluridil, cimetidine, gestrinone, or abiraterone (e.g., abiraterone acetate). In embodiments, the second agent is a second agent described herein (e.g., in the pharmaceutical composition section above).

In embodiments, the nuclear receptor activity-associated disease is cancer. In embodiments, the nuclear receptor activity-associated disease is an androgen receptor activity-associated disease. In embodiments, the androgen receptor activity-associated disease is prostate cancer, benign prostatic hyperplasia, hypersexuality, acne, amenorrhea, seborrhea, hirsutism, androgenic alopecia, hidradenitis suppurativa, or hyperandrogenism. In embodiments, the disease is prostate cancer. In embodiments, the disease is hormone-sensitive prostate cancer. In embodiments, the disease is hormone-insensitive prostate cancer. In embodiments, the cancer is drug-resistant cancer. In embodiments, the prostate cancer is drug-resistant prostate cancer. In embodiments, the prostate cancer is casodex-resistant prostate cancer. In embodiments, the prostate cancer is Flutamide-resistant prostate cancer. In embodiments, the prostate cancer is MDV3100-resistant prostate cancer. In embodiments, the prostate cancer is ARN-509-resistant prostate cancer. In embodiments, the subject is resistant to casodex, flutamide, MDV3100 (enzalutamide), and/or ARN-509. In embodiments, the prostate cancer is resistant to treatment (e.g., is not treated, is not diminished, rate of growth is not slowed, or tumor size is not reduced) with flutamide, nilutamide, bicalutamide, ARN-509, apalutamide, enzalutamide, darolutamide, cyproterone (e.g., cyproterone acetate), megestrol (e.g., megestrol acetate), chlormadinone (e.g., chlormadinone acetate), spironolactone, canrenone, drospirenone, ketoconazole, topilutamide, cimetidine, gestrinone, or abiraterone (e.g., abiraterone acetate). In embodiments, the prostate cancer is resistant to treatment (e.g., is not treated, is not diminished, rate of growth is not slowed, or tumor size is not reduced) a 5α-reductase inhibitor (e.g., finasteride, dutasteride, alfatradiol, saw palmetto extract). In embodiments, the cancer is castration-resistant prostate cancer. In embodiments, the androgen receptor activity-associated disease is bone cancer. In embodiments, the androgen receptor activity-associated disease is breast cancer. In embodiments, the androgen receptor activity-associated disease is triple negative breast cancer. In embodiments, the androgen receptor activity-associated disease is bladder cancer. In embodiments, the androgen receptor activity-associated disease is salivary gland cancer. In embodiments, the androgen receptor activity-associated disease is salivary duct carcinoma. In embodiments, the androgen receptor activity-associated disease is metastatic cancer located in bone. In embodiments, the androgen receptor activity-associated disease is metastatic castration-resistant prostate cancer. In embodiments, the androgen receptor activity-associated disease is non-metastatic castration-resistant prostate cancer. In embodiments, the androgen receptor activity-associated disease is hormone naïve metastatic prostate cancer. In embodiments, the androgen receptor activity-associated disease is prostate cancer with increasing PSA following first line treatment. In embodiments, the androgen receptor activity-associated disease is uterine cancer. In embodiments, the disease is prostate cancer. In embodiments, the disease is hormone sensitive prostate cancer. In embodiments, the disease is castration resistant prostate cancer. In embodiments, the disease is enzalutamide resistant prostate cancer. In embodiments, the disease is abiraterone resistant prostate cancer. In embodiments, the disease is docetaxel resistant prostate cancer. In embodiments, the disease is cabazitaxel resistant prostate cancer. In embodiments, the disease is radium 233 treatment resistant prostate cancer. In embodiments, the disease is sipiluecel-T resistant prostate cancer. In embodiments, the disease is non-metastatic castration resistant prostate cancer (N0). In embodiments, the disease is post-definitive intervention with rising PSA prostate cancer. In embodiments, the disease is metastatic prostate cancer. In embodiments, the disease is enzalutamide resistant cancer. In embodiments, the disease is abiraterone resistant cancer. In embodiments, the disease is docetaxel resistant cancer. In embodiments, the disease is cabazitaxel resistant cancer. In embodiments, the disease is radium 233 treatment resistant cancer. In embodiments, the disease is sipiluecel-T resistant cancer. In embodiments, the disease is non-metastatic castration resistant prostate cancer (N0). In embodiments, the disease is post-definitive intervention with rising PSA prostate cancer. In embodiments, the disease is metastatic cancer. In embodiments, a compound described herein is used as an adjuvant with definitive intervention (e.g., a second agent, an anti-cancer agent) of prostate cancer. In embodiments, a compound described herein is used as a neo-adjuvant with definitive intervention (e.g., a second agent, an anti-cancer agent) of prostate cancer. In embodiments, the nuclear receptor activity-associated disease (e.g., androgen receptor activity-associated disease, prostate cancer including embodiments of prostate cancer described herein) is associated with androgen receptor activity. In embodiments, the androgen receptor is a human receptor. In embodiments, the androgen receptor is a mutant androgen receptor. In embodiments, the mutant androgen receptor is associated with a disease that is not associated with wildtype androgen receptor. In embodiments, the mutant androgen receptor is a splice variant. In embodiments, the mutant androgen receptor is lacking a portion of the ligand binding domain. In embodiments, the mutant androgen receptor is active in the absence of bound ligand. In embodiments, the mutant androgen receptor is lacking the ligand binding domain. In embodiments, the androgen receptor is AR variant 1 (e.g., GI:21322252 (SEQ ID NO:5)). In embodiments, the androgen receptor is AR variant 2 (AR45) (e.g., GI:21713434 (SEQ ID NO:6)). In embodiments, the androgen receptor is AR variant 3 (AR-V7) (e.g., GI:224181614 (SEQ ID NO:7)). In embodiments, the androgen receptor is AR variant 4 (AR-V1) (e.g., GI:224181616 (SEQ ID NO:8)). In embodiments, the androgen receptor is AR variant 5 (AR-V4) (e.g., GI:224181620 (SEQ ID NO:9)). In embodiments, the androgen receptor is AR variant 6 (AR-V3) (e.g., GI:224181622 (SEQ ID NO:10)). In embodiments, the androgen receptor is AR v567es (e.g., GI:270358642 (SEQ ID NO:11)).

In embodiments, the method of treatment is a method of prevention. In embodiments, the compounds set forth herein are provided as pharmaceutical compositions including the compound and a pharmaceutically acceptable excipient. In embodiments, the method of treatment is not a method of prevention.

In another aspect is provided a compound described herein for use in the treatment of a nuclear receptor activity-associated disease in a subject in need of such treatment. The use may include administering a compound, or a pharmaceutically acceptable salt thereof, as described herein.

In another aspect is provided a compound described herein for use in the treatment of cancer. The use may include administering a compound, or a pharmaceutically acceptable salt thereof, as described herein. In embodiments, the compound is administered in a therapeutically effective amount. In embodiments, the cancer is prostate cancer. In embodiments, the cancer is hormone-sensitive prostate cancer. In embodiments, the cancer is hormone-insensitive prostate cancer. In embodiments, the cancer is drug-resistant cancer. In embodiments, the prostate cancer is drug-resistant prostate cancer. In embodiments, the cancer is metastatic cancer. In embodiments, the cancer is metastatic prostate cancer. In embodiments, the cancer is castration-resistant prostate cancer. In embodiments, the cancer is metastatic castration-resistant prostate cancer. In embodiments, the cancer is non-metastatic castration-resistant prostate cancer. In embodiments, the cancer is hormone nave metastatic prostate cancer. In embodiments, the cancer is prostate cancer with increasing PSA following first line treatment. In embodiments, the cancer is uterine cancer. In embodiments, the disease is castration resistant prostate cancer. In embodiments, the disease is enzalutamide resistant prostate cancer. In embodiments, the disease is abiraterone resistant prostate cancer. In embodiments, the disease is docetaxel resistant prostate cancer. In embodiments, the disease is cabazitaxel resistant prostate cancer. In embodiments, the disease is radium 233 treatment resistant prostate cancer. In embodiments, the disease is sipiluecel-T resistant prostate cancer. In embodiments, the disease is non-metastatic castration resistant prostate cancer (N0). In embodiments, the disease is post-definitive intervention with rising PSA prostate cancer. In embodiments, the disease is metastatic prostate cancer. In embodiments, the disease is enzalutamide resistant cancer. In embodiments, the disease is abiraterone resistant cancer. In embodiments, the disease is docetaxel resistant cancer. In embodiments, the disease is cabazitaxel resistant cancer. In embodiments, the disease is radium 233 treatment resistant cancer. In embodiments, the disease is sipiluecel-T resistant cancer. In embodiments, the disease is non-metastatic castration resistant prostate cancer (N0). In embodiments, the disease is post-definitive intervention with rising PSA prostate cancer. In embodiments, the disease is metastatic cancer.

In another aspect is provided a compound described herein for use as a medicament.

In another aspect is provided the use of a compound described herein in the manufacture of a medicament for the treatment of a nuclear receptor activity-associated disease in a subject in need of such treatment. The use may include administering a compound, or a pharmaceutically acceptable salt thereof, as described herein.

In embodiments, the compound, or pharmaceutically acceptable salt thereof, is included in an effective amount. In embodiments, the compound, or pharmaceutically acceptable salt thereof, is included in a therapeutically effective amount. In embodiments, the compound, or pharmaceutically acceptable salt thereof, is included in a prophylactically effective amount.

In embodiments, the use includes a second agent (e.g. therapeutic agent). In embodiments, the use includes a second agent (e.g. therapeutic agent) in a therapeutically effective amount. In embodiments, the second agent is an agent for treating cancer (e.g. prostate cancer) or an aberrant level of androgen receptor activity or a disease associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism). In embodiments, the second agent is an anti-cancer agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that does not include the hormone binding site. In embodiments, the second agent binds androgen receptor at a site that is not the hormone binding site. In embodiments, the second agent does not bind the ligand binding domain. In embodiments, the second agent binds androgen receptor at a site that is different from the site bound by a compound described herein, including embodiments. In embodiments, the second agent binds androgen receptor at a site that does not overlap with the binding site of a compound described herein, including embodiments. In embodiments, the second agent is a second agent described herein (e.g., in the pharmaceutical composition section above).

In embodiments, the nuclear receptor activity-associated disease is cancer. In embodiments, the nuclear receptor activity-associated disease is an androgen receptor activity-associated disease. In embodiments, the androgen receptor activity-associated disease is prostate cancer, benign prostatic hyperplasia, hypersexuality, acne, amenorrhea, seborrhea, hirsutism, androgenic alopecia, hidradenitis suppurativa, or hyperandrogenism. In embodiments, the disease is prostate cancer. In embodiments, the disease is hormone-sensitive prostate cancer. In embodiments, the disease is hormone-insensitive prostate cancer. In embodiments, the cancer is castration-resistant prostate cancer. In embodiments, the cancer is drug-resistant cancer. In embodiments, the prostate cancer is drug-resistant prostate cancer. In embodiments, the prostate cancer is casodex-resistant prostate cancer. In embodiments, the prostate cancer is Flutamide-resistant prostate cancer. In embodiments, the prostate cancer is MDV3100-resistant prostate cancer. In embodiments, the prostate cancer is ARN-509-resistant prostate cancer. In embodiments, the subject is resistant to casodex, flutamide, MDV3100, and/or ARN-509. In embodiments, the use includes a delay in drug resistance. In embodiments, the androgen receptor activity-associated disease is bone cancer. In embodiments, the androgen receptor activity-associated disease is breast cancer. In embodiments, the androgen receptor activity-associated disease is triple negative breast cancer. In embodiments, the androgen receptor activity-associated disease is bladder cancer. In embodiments, the androgen receptor activity-associated disease is salivary gland cancer. In embodiments, the androgen receptor activity-associated disease is salivary duct carcinoma. In embodiments, the androgen receptor activity-associated disease is metastatic cancer located in bone. In embodiments, the disease is castration resistant prostate cancer. In embodiments, the disease is enzalutamide resistant prostate cancer.

In embodiments, the disease is abiraterone resistant prostate cancer. In embodiments, the disease is docetaxel resistant prostate cancer. In embodiments, the disease is cabazitaxel resistant prostate cancer. In embodiments, the disease is radium 233 treatment resistant prostate cancer. In embodiments, the disease is sipiluecel-T resistant prostate cancer. In embodiments, the disease is non-metastatic castration resistant prostate cancer (N0). In embodiments, the disease is post-definitive intervention with rising PSA prostate cancer. In embodiments, the disease is metastatic prostate cancer. In embodiments, the disease is enzalutamide resistant cancer. In embodiments, the disease is abiraterone resistant cancer. In embodiments, the disease is docetaxel resistant cancer. In embodiments, the disease is cabazitaxel resistant cancer. In embodiments, the disease is radium 233 treatment resistant cancer. In embodiments, the disease is sipiluecel-T resistant cancer. In embodiments, the disease is non-metastatic castration resistant prostate cancer (N0). In embodiments, the disease is post-definitive intervention with rising PSA prostate cancer. In embodiments, the disease is metastatic cancer.

In embodiments, the treatment is prevention. In embodiments, the compounds set forth herein are provided as pharmaceutical compositions including the compound and a pharmaceutically acceptable excipient.

In another aspect is provided a method of treating cancer in a subject in need of such treatment, the method including administering a compound, or a pharmaceutically acceptable salt thereof, as described herein, including embodiments or in an example, table, figure, or claim.

In embodiments of the method, the compound, or pharmaceutically acceptable salt thereof, is included in an effective amount. In embodiments of the method, the compound, or pharmaceutically acceptable salt thereof, is included in a therapeutically effective amount. In embodiments of the method, the compound, or pharmaceutically acceptable salt thereof, is included in a prophylactically effective amount.

In embodiments, the cancer is prostate cancer. In embodiments, the cancer is hormone-sensitive prostate cancer. In embodiments, the cancer is hormone-insensitive prostate cancer. In embodiments, the cancer is castration-resistant prostate cancer. In embodiments, the cancer is drug-resistant cancer. In embodiments, the prostate cancer is drug-resistant prostate cancer. In embodiments, the prostate cancer is casodex-resistant prostate cancer. In embodiments, the prostate cancer is Flutamide-resistant prostate cancer. In embodiments, the prostate cancer is MDV3100-resistant prostate cancer. In embodiments, the prostate cancer is ARN-509-resistant prostate cancer. In embodiments, the subject is resistant to casodex, flutamide, MDV3100, and/or ARN-509. In embodiments, the prostate cancer is resistant to treatment (e.g., is not treated, is not diminished, rate of growth is not slowed, or tumor size is not reduced) with flutamide, nilutamide, bicalutamide, ARN-509, apalutamide, enzalutamide, darolutamide, cyproterone (e.g., cyproterone acetate), megestrol (e.g., megestrol acetate), chlormadinone (e.g., chlormadinone acetate), spironolactone, canrenone, drospirenone, ketoconazole, topilutamide, fluridil, cimetidine, gestrinone, or abiraterone (e.g., abiraterone acetate). In embodiments, the prostate cancer is resistant to treatment (e.g., is not treated, is not diminished, rate of growth is not slowed, or tumor size is not reduced) a 5α-reductase inhibitor (e.g., finasteride, dutasteride, alfatradiol, saw palmetto extract). In embodiments, the cancer is castration-resistant prostate cancer. In embodiments, the cancer is bone cancer. In embodiments, the cancer is breast cancer. In embodiments, the cancer is triple negative breast cancer. In embodiments, the cancer is bladder cancer. In embodiments, the cancer is salivary gland cancer. In embodiments, the cancer is salivary duct carcinoma. In embodiments, the cancer is metastatic cancer. In embodiments, the cancer is metastatic cancer located in bone. In embodiments, the cancer is metastatic castration-resistant prostate cancer. In embodiments, the cancer is non-metastatic castration-resistant prostate cancer. In embodiments, the cancer is hormone naïve metastatic prostate cancer. In embodiments, the cancer is prostate cancer with increasing PSA following first line treatment. In embodiments, the cancer is uterine cancer. In embodiments, the disease is castration resistant prostate cancer. In embodiments, the disease is enzalutamide resistant prostate cancer. In embodiments, the disease is abiraterone resistant prostate cancer. In embodiments, the disease is docetaxel resistant prostate cancer. In embodiments, the disease is cabazitaxel resistant prostate cancer. In embodiments, the disease is radium 233 treatment resistant prostate cancer. In embodiments, the disease is sipiluecel-T resistant prostate cancer. In embodiments, the disease is non-metastatic castration resistant prostate cancer (N0). In embodiments, the disease is post-definitive intervention with rising PSA prostate cancer. In embodiments, the disease is metastatic prostate cancer. In embodiments, the disease is enzalutamide resistant cancer. In embodiments, the disease is abiraterone resistant cancer. In embodiments, the disease is docetaxel resistant cancer. In embodiments, the disease is cabazitaxel resistant cancer. In embodiments, the disease is radium 233 treatment resistant cancer. In embodiments, the disease is sipiluecel-T resistant cancer. In embodiments, the disease is non-metastatic castration resistant prostate cancer (N0). In embodiments, the disease is post-definitive intervention with rising PSA prostate cancer. In embodiments, the disease is metastatic cancer.

E. METHODS OF INHIBITING A NUCLEAR RECEPTOR

In another aspect is provided a method of inhibiting androgen receptor activity in a subject in need thereof, including administering to the subject an effective amount of a compound as described herein, or a pharmaceutically acceptable salt thereof.

In another aspect is provided a method of inhibiting androgen receptor activity, the method including contacting an androgen receptor with an effective amount of a compound described herein, or a pharmaceutically acceptable salt thereof.

In embodiments, the nuclear receptor is a human receptor. In embodiments, the nuclear receptor is an androgen receptor. In embodiments, the androgen receptor is a human receptor. In embodiments, the androgen receptor is a mutant androgen receptor. In embodiments, the mutant androgen receptor is associated with a disease that is not associated with wildtype androgen receptor. In embodiments, the mutant androgen receptor is a splice variant. In embodiments, the mutant androgen receptor is lacking a portion of the ligand binding domain. In embodiments, the mutant androgen receptor is active in the absence of bound ligand. In embodiments, the mutant androgen receptor is lacking the ligand binding domain. In embodiments, the androgen receptor is AR variant 1 (e.g., GI:21322252 (SEQ ID NO:5)). In embodiments, the androgen receptor is AR variant 2 (AR45) (e.g., GI:21713434 (SEQ ID NO:6)). In embodiments, the androgen receptor is AR variant 3 (AR-V7) (e.g., GI:224181614 (SEQ ID NO:7)). In embodiments, the androgen receptor is AR variant 4 (AR-V1) (e.g., GI:224181616 (SEQ ID NO:8)). In embodiments, the androgen receptor is AR variant 5 (AR-V4) (e.g., GI:224181620 (SEQ ID NO:9)). In embodiments, the androgen receptor is AR variant 6 (AR-V3) (e.g., GI:224181622 (SEQ ID NO:10)). In embodiments, the androgen receptor is AR v567es (e.g., GI:270358642 (SEQ ID NO:11)).

F. FURTHER EMBODIMENTS

Embodiment P1

A compound, or a pharmaceutically acceptable salt thereof, having the formula:

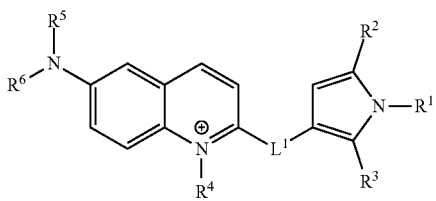

(I)

wherein $R^1$ is hydrogen or substituted or unsubstituted pyrid-2-yl; $R^2$ is independently a hydrogen, halogen, —$CX^2_3$, —$CHX^2_2$, —$CH_2X^2$, —CN, —$SO_{n2}R^{10}$, —$SO_{v2}NR^7R^8$, —$NHNR^7R^8$, —$ONR^7R^8$, —NHC=(O)NHNR$^7$R$^8$, —NHC=(O)NR$^7$R$^8$, —N(O)$_{m2}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C=(O)R$^9$, —NR$^7$C(O)—OR$^9$, —NR$^7$OR$^9$, —OCX$^2_3$, —OCHX$^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently a hydrogen, halogen, —$CX^3_3$, —$CHX^3_2$, —$CH_2X^3$, —CN, —$SO_{n3}R^{14}$, —$SO_{v3}NR^{11}R^{12}$, —$NHNH_2$, —$ONR^{11}R^{12}$, —NHC=(O)NHNH$_2$, —NHC=(O)NR$^{11}$R$^{12}$, —N(O)$_{m3}$, —NR$^{11}$R$^{12}$, —C(O)R$^{13}$, —C(O)—OR$^{13}$, —C(O)NR$^{11}$R$^{12}$, —OR$^{14}$, —NR$^{11}$SO$_2$R$^{14}$, —NR$^{11}$C=(O)R$^{13}$, —NR$^{11}$C(O)—OR$^{13}$, —NR$^{11}$OR$^{13}$, —OCX$^3_3$, —OCHX$^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, and $R^{14}$ are independently hydrogen, halogen, —$CX_3$, —CN, —OH, —$NH_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$_3$, —OCHX$_2$, —CF$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^4$ is independently hydrogen, a —$CX^4_3$, —$CHX^4_2$, —$CH_2X^4$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently a hydrogen, halogen, —$CX^5_3$, —$CHX^5_2$, —$CH_2X^5$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is independently a hydrogen, halogen, —$CX^6_3$, —$CHX^6_2$, —$CH_2X^6$—CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is independently a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene; m2, m3, v2, and v3 are independently 1 or 2; n2 and n3 are independently an integer from 0 to 4; X, $X^2$, $X^3$, $X^4$, $X^5$, and $X^6$ are independently —Cl, —Br, —I, or —F.

Embodiment P2

The compound of embodiment P1, having the formula:

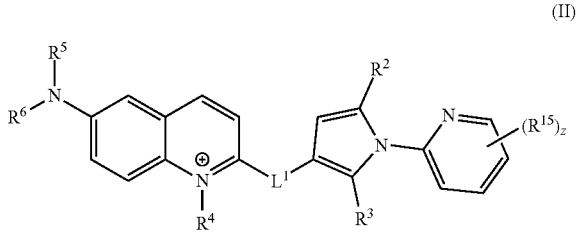

(II)

wherein $R^{15}$ is independently a halogen, —$CX^{15}_3$, —$CHX^{15}_2$, —$CH_2X^{15}$, —CN, —$SO_{n15}R^{19}$, —$SO_{v15}NR^{16}R^{17}$, —$NHNR^{16}R^{17}$, —$ONR^{16}R^{17}$, —NHC=(O)NHNR$^{16}$R$^{17}$, —NHC=(O)NR$^{16}$R$^{17}$, —N(O)$_{m15}$, —NR$^{16}$R$^{17}$, —C(O)R$^{18}$, —C(O)—OR$^{18}$, —C(O)NR$^{16}$R$^{17}$, —OR$^{19}$, —NR$^{16}$SO$_2$R$^{19}$, —NR$^{16}$C=(O)R$^{18}$, —NR$^{16}$C(O)OR$^{18}$, —NR$^{16}$OR$^{18}$, —OCX$^{15}_3$, —OCHX$^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$, $R^{17}$, $R^{18}$, and $R^{19}$ are independently hydrogen, halogen, —$CX_3$, —CN, —OH, —$NH_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —CF$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ and $R^{17}$ substituents bonded to the same nitrogen atom may optionally be joined to form a substituted or unsubstituted heterocycloalkyl or substituted or unsubstituted heteroaryl; $R^4$ is independently hydrogen, a —$CX^4_3$, —$CHX^4_2$, —$CH_2X^4$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m15 and v5 are independently 1 or 2; n15 is independently an integer from 0 to 4; z is an integer from 0 to 4; $X^{15}$ is independently —Cl, —Br, —I, or —F.

Embodiment P3

The compound of embodiment P2, wherein $R^{15}$ is independently a halogen, —$CX^{15}_3$, —$CHX^{15}_2$, —$CH_2X^{15}$, —CN, —$NHNH_2$, —$NO_2$, —$NH_2$, —C(O)H, —C(O)OH, —C(O)$NH_2$, —OH, —NHC(O)OH, —$OCX^{15}_3$, —$OCHX^{15}_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment P4

The compound of embodiment P2, wherein $R^{15}$ is independently a halogen, —$CX^{15}_3$, —CN, —$NH_2$, —OH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P5

The compound of embodiment P2, wherein $R^{15}$ is independently a halogen, —$CF_3$, —CN, —$NH_2$, —OH, unsubstituted $C_1$-$C_4$ alkyl, or unsubstituted 2 to 4 membered heteroalkyl.

Embodiment P6

The compound of embodiment P2, wherein $R^{15}$ is independently a halogen, —$CF_3$, unsubstituted methyl, unsubstituted ethyl, unsubstituted isopropyl, unsubstituted methoxy, or unsubstituted ethoxy.

Embodiment P7

The compound of embodiment P1, having the formula:

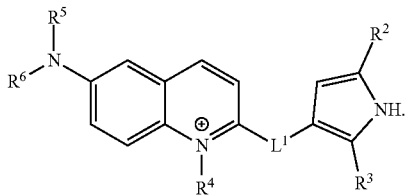

(III)

Embodiment P8

The compound of one of embodiments P1 to P7, wherein $R^2$ is independently a hydrogen, halogen, —$CX^2_3$, —$CHX^2_2$, —$CH_2X^2$, —CN, —$NO_2$, —$NH_2$, —OH, —$OCX^2_3$, —$OCHX^2_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment P9

The compound of one of embodiments P1 to P7, wherein $R^2$ is independently a hydrogen, halogen, —$CX^2_3$, —$CHX^2_2$, —$CH_2X^2$, —$OCX^2_3$, —$OCHX^2_2$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P10

The compound of one of embodiments P1 to P7, wherein $R^2$ is independently a hydrogen, halogen, —$CF_3$, unsubstituted $C_1$-$C_4$ alkyl, or unsubstituted 2 to 4 membered heteroalkyl.

Embodiment P11

The compound of one of embodiments P1 to P7, wherein $R^2$ is independently a halogen, —$CF_3$, unsubstituted methyl, unsubstituted ethyl, unsubstituted isopropyl, unsubstituted methoxy, or unsubstituted ethoxy.

Embodiment P12

The compound of one of embodiments P1 to P11, wherein $R^3$ is independently a hydrogen, halogen, —$CX^3_3$, —$CHX^3_2$, —$CH_2X^3$, —CN, —$NO_2$, —$NH_2$, —OH, —$OCX^3_3$, —$OCHX^3_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment P13

The compound of one of embodiments P1 to P11, wherein $R^3$ is independently a hydrogen, halogen, —$CX^3_3$, —$CHX^3_2$, —$CH_2X^3$, —$OCX^3_3$, —$OCHX^3_2$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P14

The compound of one of embodiments P1 to P11, wherein $R^3$ is independently a hydrogen, halogen, —$CF_3$, unsubstituted $C_1$-$C_4$ alkyl, or unsubstituted 2 to 4 membered heteroalkyl.

Embodiment P15

The compound of one of embodiments P1 to P11, wherein $R^3$ is independently a halogen, —$CF_3$, unsubstituted methyl, unsubstituted ethyl, unsubstituted isopropyl, unsubstituted methoxy, or unsubstituted ethoxy.

Embodiment P16

The compound of one of embodiments P1 to P15, wherein $R^4$ is independently hydrogen, —$CF_3$, or substituted or unsubstituted $C_1$-$C_4$ alkyl.

Embodiment P17

The compound of one of embodiments P1 to P15, wherein $R^4$ is independently hydrogen, —$CF_3$, unsubstituted methyl, unsubstituted ethyl, or unsubstituted isopropyl.

Embodiment P18

The compound of one of embodiments P1 to P17, wherein $R^5$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P19

The compound of one of embodiments P1 to P17, wherein $R^5$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment P20

The compound of one of embodiments P1 to P17, wherein $R^5$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P21

The compound of one of embodiments P1 to P17, wherein $R^5$ is a hydrogen, unsubstituted $C_1$-$C_4$ alkyl.

Embodiment P22

The compound of one of embodiments P1 to P17, wherein $R^5$ is an unsubstituted methyl or unsubstituted ethyl.

Embodiment P23

The compound of one of embodiments P1 to P22, wherein $R^6$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P24

The compound of one of embodiments P1 to P22, wherein $R^6$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment P25

The compound of one of embodiments P1 to P22, wherein $R^6$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P26

The compound of one of embodiments P1 to P22, wherein $R^6$ is a hydrogen, unsubstituted $C_1$-$C_4$ alkyl.

Embodiment P27

The compound of one of embodiments P1 to P22, wherein $R^6$ is an unsubstituted methyl or unsubstituted ethyl.

Embodiment P28

The compound of one of embodiments P1 to P27, wherein $L^1$ is independently a bond, substituted or unsubstituted alkylene, substituted or unsubstituted alkenylene, substituted or unsubstituted heteroalkylene, or substituted or unsubstituted heteroalkenylene.

Embodiment P29

The compound of one of embodiments P1 to P27, wherein $L^1$ is independently a bond, substituted or unsubstituted $C_1$-$C_4$ alkylene, substituted or unsubstituted $C_2$-$C_4$ alkenylene, substituted or unsubstituted 2 to 4 membered heteroalkylene, or substituted or unsubstituted 3 to 4 membered heteroalkenylene.

Embodiment P30

The compound of one of embodiments P1 to P27, wherein $L^1$ is independently a bond, unsubstituted $C_1$-$C_4$ alkylene, unsubstituted $C_2$-$C_4$ alkenylene, unsubstituted 2 to 4 membered heteroalkylene, or unsubstituted 3 to 4 membered heteroalkenylene.

Embodiment P31

The compound of one of embodiments P1 to P27, wherein $L^1$ is independently an unsubstituted $C_2$-$C_3$ alkylene or unsubstituted alkenylene.

Embodiment P32

The compound of one of embodiments P1 to P27, wherein $L^1$ is independently an unsubstituted ethylene or unsubstituted ethenylene.

Embodiment P33

The compound of embodiment P1, wherein the compound is:

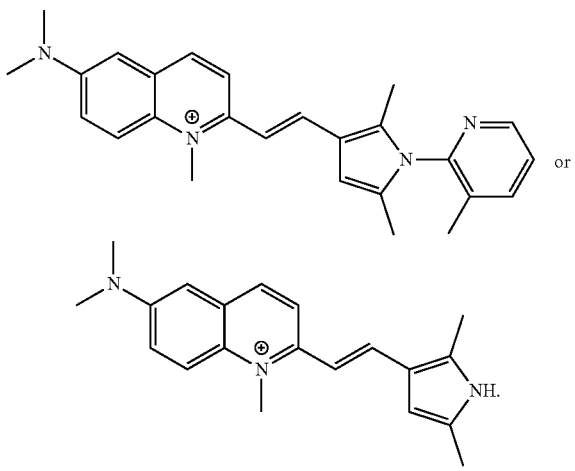

Embodiment P34

The compound of one of embodiments P1 to P33 wherein said compound is an antagonist of a nuclear receptor.

Embodiment P35

The compound of one of embodiments P1 to P33, wherein said compound is an antagonist of an androgen receptor.

Embodiment P36

A pharmaceutical composition comprising a compound of one of embodiments P1 to P35 or a pharmaceutically acceptable salt thereof, and a pharmaceutically acceptable excipient.

Embodiment P37

A method of treating a disease associated with androgen receptor activity in a patient in need of such treatment, said method comprising administering a therapeutically effective amount of a compound of one of embodiments P1 to P35, or a pharmaceutically acceptable salt thereof.

Embodiment P38

A method of treating cancer in a patient in need of such treatment, said method comprising administering a therapeutically effective amount of a compound of one of embodiments P1 to P35, or a pharmaceutically acceptable salt thereof.

Embodiment P39

The method of embodiment P38, wherein said cancer is prostate cancer.

Embodiment P40

The method of embodiment P38, wherein said cancer is hormone sensitive prostate cancer.

Embodiment P41

The method of embodiment P38, wherein said cancer is hormone refractory prostate cancer.

Embodiment P42

A method of inhibiting androgen receptor activity, said method comprising contacting an androgen receptor with an effective amount of a compound of one of embodiments P1 to P33.

G. ADDITIONAL EMBODIMENTS

Embodiment 1

A compound, or a pharmaceutically acceptable salt thereof, having the formula:

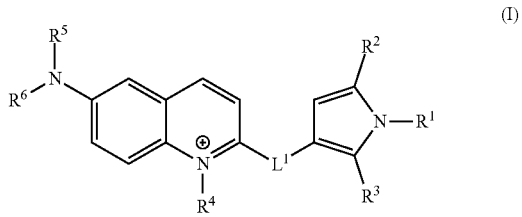

(I)

wherein $R^1$ is hydrogen or substituted or unsubstituted pyrid-2-yl; $R^2$ is independently a hydrogen, halogen, $—CX^2_3$, $—CHX^2_2$, $—CH_2X^2$, $—CN$, $—SO_{n2}R^{10}$, $—SO_{v2}NR^7R^8$, $—NHNR^7R^8$, $—ONR^7R^8$, $—NHC=(O)NHNR^7R^8$, $—NHC=(O)NR^7R^8$, $—N(O)_{m2}$, $—NR^7R^8$, $—C(O)R^9$, $—C(O)—OR^9$, $—C(O)NR^7R^8$, $—OR^{10}$, $—NR^7SO_2R^{10}$, $—NR^7C=(O)R^9$, $—NR^7C(O)—OR^9$, $—NR^7OR^9$, $—OCX^2_3$, $—OCHX^2_2$, $—OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently a hydrogen, halogen, $—CX^3_3$, $—CHX^3_2$, $—CH_2X^3$, $—CN$, $—SO_{n3}R^{14}$, $—SO_{v3}NR^{11}R^{12}$, $—NHNH_2$, $—ONR^{11}R^{12}$, $—NHC=(O)NHNH_2$, $—NHC=(O)NR^{11}R^{12}$, $—N(O)_{m3}$, $—NR^{11}R^{12}$, $—C(O)R^{13}$, $—C(O)OR^{13}$, $—C(O)NR^{11}R^{12}$, $—OR^{14}$, $—NR^{11}SO_2R^{14}$, $—NR^{11}C=(O)R^{13}$, $—NR^{11}C(O)—OR^{13}$, $—NR^{11}OR^{13}$, $—OCX^3_3$, $—OCHX^3_2$, $—OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, and $R^{14}$ are independently hydrogen, halogen, $—CX_3$, $—CHX_2$, $—CH_2X$, $—OCX_3$, $—OCHX_2$, $—OCH_2X$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)—OH$, $—NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^4$ is independently hydrogen, a —$CX^4{}_3$, —$CHX^4{}_2$, —$CH_2X^4$, —CN, —C(O)H, —C(O)OH, —C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently a hydrogen, halogen, —$CX^5{}_3$, —$CHX^5{}_2$, —$CH_2X^5$, —CN, —C(O)H, —C(O)OH, —C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is independently a hydrogen, halogen, —$CX^6{}_3$, —$CHX^6{}_2$, —$CH_2X^6$—CN, —C(O)H, —C(O)OH, —C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is independently a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene; m2, m3, v2, and v3 are independently 1 or 2; n2 and n3 are independently an integer from 0 to 4; X, $X^2$, $X^3$, $X^4$, $X^5$, and $X^6$ are independently —Cl, —Br, —I, or —F.

Embodiment 2

The compound of embodiment 1, having the formula:

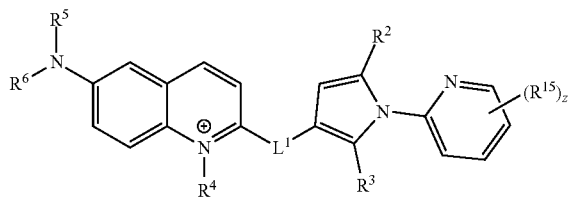

(II)

wherein $R^{15}$ is independently a halogen, —$CX^{15}{}_3$, —$CHX^{15}{}_2$, —$CH_2X^{15}$, —CN, —$SO_{n15}R^{19}$, —$SO_{v15}NR^{16}R^{17}$, —$NHNR^{16}R^{17}$, —$ONR^{16}R^{17}$, —NHC=(O)NHNR^{16}R^{17}$, —NHC=(O)NR^{16}R^{17}$, —$N(O)_{m15}$, —$NR^{16}R^{17}$, —$C(O)R^{18}$, —C(O)—OR^{18}$, —$C(O)NR^{16}R^{17}$, —$OR^{19}$, —$NR^{16}SO_2R^{19}$, —$NR^{16}C=(O)R^{18}$, —$NR^{16}C(O)OR^{18}$, —$NR^{16}OR^{18}$, —$OCX^{15}{}_3$, —$OCHX^{15}{}_2$, —$OCH_2X^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$, $R^{17}$, $R^{18}$, and $R^{19}$ are independently hydrogen, halogen, —$CX_3$, —$CHX_2$, —$CH_2X$, —$OCX_3$, —$OCHX_2$, —$OCH_2X$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ and $R^{17}$ substituents bonded to the same nitrogen atom may optionally be joined to form a substituted or unsubstituted heterocycloalkyl or substituted or unsubstituted heteroaryl; $R^4$ is independently hydrogen, a —$CX^4{}_3$, —$CHX^4{}_2$, —$CH_2X^4$, —CN, —C(O)H, —C(O)OH, —C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m15 and v15 are independently 1 or 2; n15 is independently an integer from 0 to 4; z is an integer from 0 to 4; $X^{15}$ is independently —Cl, —Br, —I, or —F Embodiment 3

The compound of embodiment 2, wherein $R^{15}$ is independently a halogen, —$CX^{15}{}_3$, —$CHX^{15}{}_2$, —$CH_2X^{15}$, —CN, —$NHNH_2$, —$NO_2$, —$NH_2$, —C(O)H, —C(O)OH, —$C(O)NH_2$, —OH, —NHC(O)OH, —$OCX^{15}{}_3$, —$OCHX^{15}{}_2$, —$OCH_2X^{15}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 4

The compound of embodiment 2, wherein $R^{15}$ is independently a halogen, —$CX^{15}{}_3$, —CN, —$NH_2$, —OH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 5

The compound of embodiment 2, wherein $R^{15}$ is independently a halogen, —$CX^{15}{}_3$, —$CHX^{15}{}_2$, —$CH_2X^{15}$, —CN, —$NH_2$, —OH, unsubstituted $C_1$-$C_4$ alkyl, or unsubstituted 2 to 4 membered heteroalkyl.

Embodiment 6

The compound of embodiment 2, wherein $R^{15}$ is independently a halogen, —$CX^{15}{}_3$, —$CHX^{15}{}_2$, —$CH_2X^{15}$, unsubstituted methyl, unsubstituted ethyl, unsubstituted isopropyl, unsubstituted methoxy, or unsubstituted ethoxy.

Embodiment 7

The compound of embodiment 1, having the formula:

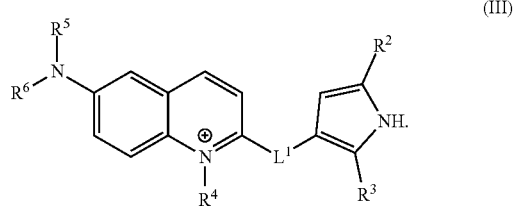

(III)

Embodiment 8

The compound of one of embodiments 1 to 7, wherein $R^2$ is independently a hydrogen, halogen, $-CX^2_3$, $-CHX^2_2$, $-CH_2X^2$, $-CN$, $-NO_2$, $-NH_2$, $-OH$, $-OCX^2_3$, $-OCHX^2_2$, $-OCH_2X^2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 9

The compound of one of embodiments 1 to 7, wherein $R^2$ is independently a hydrogen, halogen, $-CX^2_3$, $-CHX^2_2$, $-CH_2X^2$, $-OCX^2_3$, $-OCHX^2_2$, $-OCH_2X^2$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 10

The compound of one of embodiments 1 to 7, wherein $R^2$ is independently a hydrogen, halogen, $-CX^2_3$, $-CHX^2_2$, $-CH_2X^2$, unsubstituted $C_1$-$C_4$ alkyl, or unsubstituted 2 to 4 membered heteroalkyl.

Embodiment 11

The compound of one of embodiments 1 to 7, wherein $R^2$ is independently a halogen, $-CX^2_3$, $-CHX^2_2$, $-CH_2X^2$, unsubstituted methyl, unsubstituted ethyl, unsubstituted isopropyl, unsubstituted methoxy, or unsubstituted ethoxy.

Embodiment 12

The compound of one of embodiments 1 to 11, wherein $R^3$ is independently a hydrogen, halogen, $-CX^3_3$, $-CHX^3_2$, $-CH_2X^3$, $-CN$, $-NO_2$, $-NH_2$, $-OH$, $-OCX^3_3$, $-OCHX^3_2$, $-OCH_2X^3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 13

The compound of one of embodiments 1 to 11, wherein $R^3$ is independently a hydrogen, halogen, $-CX^3_3$, $-CHX^3_2$, $-CH_2X^3$, $-OCX^3_3$, $-OCHX^3_2$, $-OCH_2X^3$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 14

The compound of one of embodiments 1 to 11, wherein $R^3$ is independently a hydrogen, halogen, $-CX^3_3$, $-CHX^3_2$, $-CH_2X^3$, unsubstituted $C_1$-$C_4$ alkyl, or unsubstituted 2 to 4 membered heteroalkyl.

Embodiment 15

The compound of one of embodiments 1 to 11, wherein $R^3$ is independently a halogen, $-CX^3_3$, $-CHX^3_2$, $-CH_2X^3$, unsubstituted methyl, unsubstituted ethyl, unsubstituted isopropyl, unsubstituted methoxy, or unsubstituted ethoxy.

Embodiment 16

The compound of one of embodiments 1 to 15, wherein $R^4$ is independently hydrogen, $-CF_3$, or substituted or unsubstituted $C_1$-$C_4$ alkyl.

Embodiment 17

The compound of one of embodiments 1 to 16, wherein $R^4$ is independently hydrogen, $CX^4_3$, $-CHX^4_2$, $-CH_2X^4$, unsubstituted methyl, unsubstituted ethyl, or unsubstituted isopropyl.

Embodiment 18

The compound of one of embodiments 1 to 17, wherein $R^5$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 19

The compound of one of embodiments 1 to 17, wherein $R^5$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 20

The compound of one of embodiments 1 to 17, wherein $R^5$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 21

The compound of one of embodiments 1 to 17, wherein $R^5$ is a hydrogen, unsubstituted $C_1$-$C_4$ alkyl.

Embodiment 22

The compound of one of embodiments 1 to 17, wherein $R^5$ is an unsubstituted methyl or unsubstituted ethyl.

Embodiment 23

The compound of one of embodiments 1 to 22, wherein $R^6$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 24

The compound of one of embodiments 1 to 22, wherein $R^6$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 25

The compound of one of embodiments 1 to 22, wherein $R^6$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 26

The compound of one of embodiments 1 to 22, wherein $R^6$ is a hydrogen, unsubstituted $C_1$-$C_4$ alkyl.

Embodiment 27

The compound of one of embodiments 1 to 22, wherein $R^6$ is an unsubstituted methyl or unsubstituted ethyl.

Embodiment 28

The compound of one of embodiments 1 to 27, wherein $L^1$ is independently a bond, substituted or unsubstituted alkylene, substituted or unsubstituted alkenylene, substituted or unsubstituted heteroalkylene, or substituted or unsubstituted heteroalkenylene.

Embodiment 29

The compound of one of embodiments 1 to 27, wherein $L^1$ is independently a bond, substituted or unsubstituted $C_1$-$C_4$ alkylene, substituted or unsubstituted $C_2$-$C_4$ alkenylene, substituted or unsubstituted 2 to 4 membered heteroalkylene, or substituted or unsubstituted 3 to 4 membered heteroalkenylene.

Embodiment 30

The compound of one of embodiments 1 to 27, wherein $L^1$ is independently a bond, unsubstituted $C_1$-$C_4$ alkylene, unsubstituted $C_2$-$C_4$ alkenylene, unsubstituted 2 to 4 membered heteroalkylene, or unsubstituted 3 to 4 membered heteroalkenylene.

Embodiment 31

The compound of one of embodiments 1 to 27, wherein $L^1$ is independently an unsubstituted $C_2$-$C_3$ alkylene or unsubstituted $C_2$-$C_3$ alkenylene.

Embodiment 32

The compound of one of embodiments 1 to 27, wherein $L^1$ is independently an unsubstituted ethylene or unsubstituted ethenylene.

Embodiment 33

The compound of embodiment 1, wherein the compound is:

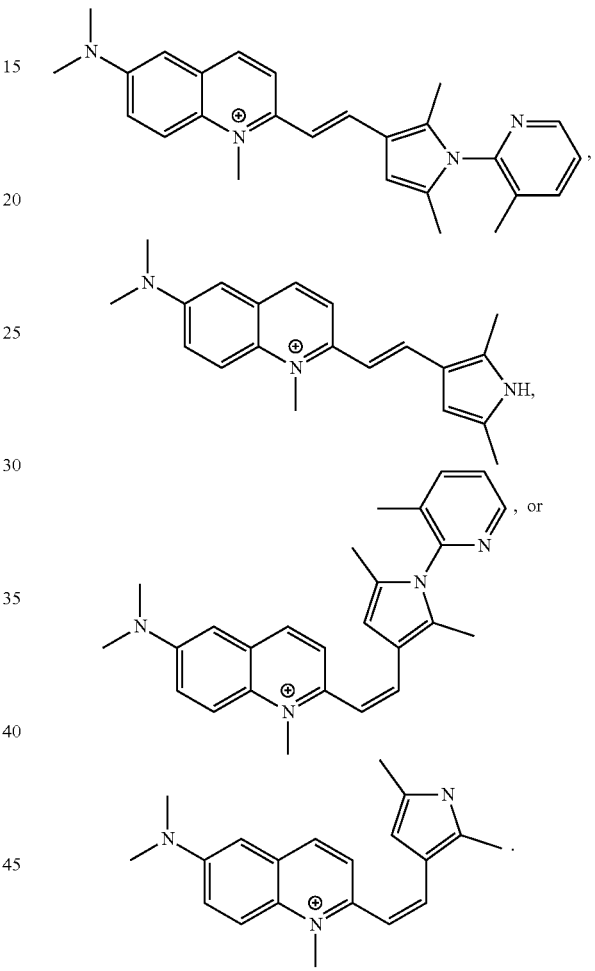

Embodiment 34

The compound of one of embodiments 1 to 33, wherein said compound is an antagonist of a nuclear receptor.

Embodiment 35

The compound of one of embodiments 1 to 33, wherein said compound is an antagonist of an androgen receptor.

Embodiment 36

A pharmaceutical composition comprising a compound of one of embodiments 1 to 35 or a pharmaceutically acceptable salt thereof, and a pharmaceutically acceptable excipient.

Embodiment 37

A method of treating a disease associated with androgen receptor activity in a patient in need of such treatment, said method comprising administering a therapeutically effective amount of a compound of one of embodiments 1 to 35, or a pharmaceutically acceptable salt thereof.

Embodiment 38

A method of treating cancer in a patient in need of such treatment, said method comprising administering a therapeutically effective amount of a compound of one of embodiments 1 to 35, or a pharmaceutically acceptable salt thereof.

Embodiment 39

The method of embodiment 38, wherein said cancer is prostate cancer.

Embodiment 40

The method of embodiment 38, wherein said cancer is hormone sensitive prostate cancer.

Embodiment 41

The method of embodiment 38, wherein said cancer is hormone refractory prostate cancer.

Embodiment 42

A method of inhibiting androgen receptor activity, said method comprising contacting an androgen receptor with an effective amount of a compound of one of embodiments 1 to 35.

Embodiment A1

A compound, or a pharmaceutically acceptable salt thereof, having the formula:

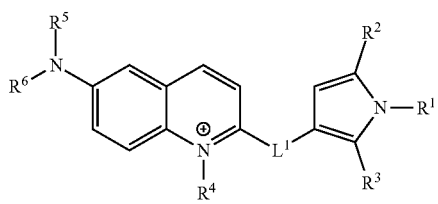

(I)

wherein $R^1$ is hydrogen or substituted or unsubstituted pyrid-2-yl; $R^2$ is independently a hydrogen, halogen, —$CX^2_3$, —$CHX^2_2$, —$CH_2X^2$, —CN, —$SO_{n2}R^{10}$, —$SO_{v2}NR^7R^8$, —$NHNR^7R^8$, —$ONR^7R^8$, —NHC=(O)NHNR$^7R^8$, —NHC=(O)NR$^7R^8$, —N(O)$_{m2}$, —NR$^7R^8$, —C(O)R$^9$, —C(O)—OR$^9$, —C(O)NR$^7R^8$, —OR$^{10}$, —NR$^7SO_2R^{10}$, —NR$^7$C=(O)R$^9$, —NR$^7$C(O)—OR$^9$, —NR$^7$OR$^9$, —OCX$^2_3$, —OCHX$^2_2$, —OCH$_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently a hydrogen, halogen, —$CX^3_3$, —$CHX^3_2$, —$CH_2X^3$, —CN, —$SO_{n3}R^{14}$, —$SO_{v3}NR^{11}R^{12}$, —NHNH$_2$, —ONR$^{11}R^{12}$, —NHC=(O)NHNH$_2$, —NHC=(O)NR$^{11}R^{12}$, —N(O)$_{m3}$, —NR$^{11}R^{12}$, —C(O)R$^{13}$, —C(O)—OR$^{13}$, —C(O)NR$^{11}R^{12}$, —OR$^{14}$, —NR$^{11}SO_2R^{14}$, —NR$^{11}$C=(O)R$^{13}$, —NR$^{11}$C(O)—OR$^{13}$, —NR$^{11}OR^{13}$, —OCX$^3_3$, —OCHX$^3_2$, —OCH$_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, and $R^{14}$ are independently hydrogen, halogen, —$CX_3$, —$CHX_2$, —$CH_2X$, —$OCX_3$, —$OCHX_2$, —$OCH_2X$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^4$ is independently hydrogen, a —$CX^4_3$, —$CHX^4_2$, —$CH_2X^4$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently a hydrogen, halogen, —$CX^5_3$, —$CHX^5_2$, —$CH_2X^5$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is independently a hydrogen, halogen, —$CX^6_3$, —$CHX^6_2$, —$CH_2X^6$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is independently a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene; m2, m3, v2, and v3 are independently 1 or 2; n2 and n3 are independently an integer from 0 to 4; X, $X^2$, $X^3$, $X^4$, $X^5$, and $X^6$ are independently —Cl, —Br, —I, or —F.

Embodiment A2

The compound of embodiment A1, having the formula:

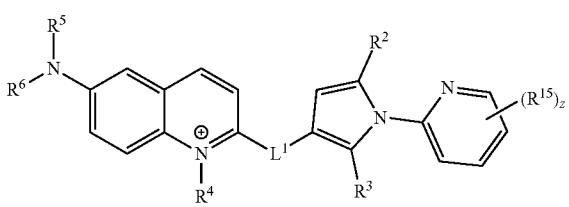

(II)

wherein $R^{15}$ is independently a halogen, $-CX^{15}{}_3$, $-CHX^{15}{}_2$, $-CH_2X^{15}$, $-CN$, $-SO_{n15}R^{19}$, $-SO_{v15}NR^{16}R^{17}$, $-NHNR^{16}R^{17}$, $-ONR^{16}R^{17}$, $-NHC=(O)NHNR^{16}R^{17}$, $-NHC=(O)NR^{16}R^{17}$, $-N(O)_{m15}$, $-NR^{16}R^{17}$, $-C(O)R^{18}$, $-C(O)-OR^{18}$, $-C(O)NR^{16}R^{17}$, $-OR^{19}$, $-NR^{16}SO_2R^{19}$, $-NR^{16}C=(O)R^{18}$, $-NR^{16}C(O)OR^{18}$, $-NR^{16}OR^{18}$, $-OCX^{15}{}_3$, $-OCHX^{15}{}_2$, $-OCH_2X^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$, $R^{17}$, $R^{18}$, and $R^{19}$ are independently hydrogen, halogen, $-CX_3$, $-CHX_2$, $-CH_2X$, $-OCX_3$, $-OCHX_2$, $-OCH_2X$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ and $R^{17}$ substituents bonded to the same nitrogen atom may optionally be joined to form a substituted or unsubstituted heterocycloalkyl or substituted or unsubstituted heteroaryl; m15 and v15 are independently 1 or 2; n15 is independently an integer from 0 to 4; z is an integer from 0 to 4; $X^{15}$ is independently $-Cl$, $-Br$, $-I$, or $-F$.

Embodiment A3

The compound of embodiment A2, wherein $R^{15}$ is independently a halogen, $-CX^{15}{}_3$, $-CHX^{15}{}_2$, $-CH_2X^{15}$, $-CN$, $-NHNH_2$, $-NO_2$, $-NH_2$, $-C(O)H$, $-C(O)OH$, $-C(O)NH_2$, $-OH$, $-NHC(O)OH$, $-OCX^{15}{}_3$, $-OCHX^{15}{}_2$, $-OCH_2X^{15}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment A4

The compound of embodiment A2, wherein $R^{15}$ is independently a halogen, $-CX^{15}{}_3$, $-CN$, $-NH_2$, $-OH$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment A5

The compound of embodiment A2, wherein $R^{15}$ is independently a halogen, $-CX^{15}{}_3$, $-CHX^{15}{}_2$, $-CH_2X^{15}$, $-CN$, $-NH_2$, $-OH$, unsubstituted $C_1$-$C_4$ alkyl, or unsubstituted 2 to 4 membered heteroalkyl.

Embodiment A6

The compound of embodiment A2, wherein $R^{15}$ is independently a halogen, $-CX^{15}{}_3$, $-CHX^{15}{}_2$, $-CH_2X^{15}$, unsubstituted methyl, unsubstituted ethyl, unsubstituted isopropyl, unsubstituted methoxy, or unsubstituted ethoxy.

Embodiment A7

The compound of embodiment A2, wherein $R^{15}$ is independently a $-CX^{15}{}_3$, $-CHX^{15}{}_2$, $-CH_2X^{15}$, unsubstituted methyl, or ethyl.

Embodiment A8

The compound of embodiment A2, wherein $R^{15}$ is independently a $-CX^{15}{}_3$, $-CHX^{15}{}_2$, $-CH_2X^{15}$, or unsubstituted methyl.

Embodiment A9

The compound of embodiment A2, wherein $R^{15}$ is independently unsubstituted methyl.

Embodiment A10

The compound of one of embodiments A2 to A9, having the formula:

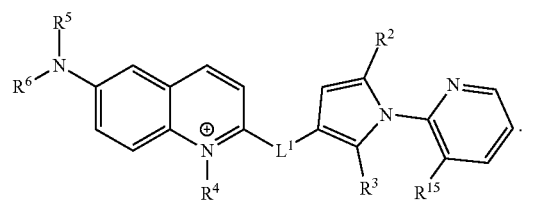

(IIa)

Embodiment A11

The compound of embodiment A1, having the formula:

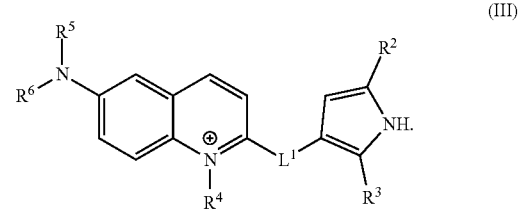

(III)

Embodiment A12

The compound of one of embodiments A1 to A11, wherein $R^2$ is independently a hydrogen, halogen, $-CX^2{}_3$, $-CHX^2{}_2$, $-CH_2X^2$, $-CN$, $-NO_2$, $-NH_2$, $-OH$, $-OCX^2{}_3$, $-OCHX^2{}_2$, $-OCH_2X^2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment A13

The compound of one of embodiments A1 to A11, wherein $R^2$ is independently a hydrogen, halogen, $-CX^2{}_3$, $-CHX^2{}_2$, $-CH_2X^2$, $-OCX^2{}_3$, $-OCHX^2{}_2$, $-OCH_2X^2$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment A14

The compound of one of embodiments A1 to A11, wherein $R^2$ is independently a hydrogen, halogen, —$CX^2{}_3$, —$CHX^2{}_2$, —$CH_2X^2$, unsubstituted $C_1$-$C_4$ alkyl, or unsubstituted 2 to 4 membered heteroalkyl.

Embodiment A15

The compound of one of embodiments A1 to A11, wherein $R^2$ is independently a halogen, —$CX^2{}_3$, —$CHX^2{}_2$, —$CH_2X^2$, unsubstituted methyl, unsubstituted ethyl, unsubstituted isopropyl, unsubstituted methoxy, or unsubstituted ethoxy.

Embodiment A16

The compound of one of embodiments A1 to A11, wherein $R^2$ is independently a —$CX^2{}_3$, —$CHX^2{}_2$, —$CH_2X^2$, unsubstituted methyl, or unsubstituted ethyl.

Embodiment A17

The compound of one of embodiments A1 to A11, wherein $R^2$ is independently a —$CX^2{}_3$, —$CHX^2{}_2$, —$CH_2X^2$, or unsubstituted methyl.

Embodiment A18

The compound of one of embodiments A1 to A11, wherein $R^2$ is independently unsubstituted methyl.

Embodiment A19

The compound of one of embodiments A1 to A18, wherein $R^3$ is independently a hydrogen, halogen, —$CX^3{}_3$, —$CHX^3{}_2$, —$CH_2X^3$, —CN, —$NO_2$, —$NH_2$, —OH, —$OCX^3{}_3$, —$OCHX^3{}_2$, —$OCH_2X^3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment A20

The compound of one of embodiments A1 to A18, wherein $R^3$ is independently a hydrogen, halogen, —$CX^3{}_3$, —$CHX^3{}_2$, —$CH_2X^3$, —$OCX^3{}_3$, —$OCHX^3{}_2$, —$OCH_2X^3$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment A21

The compound of one of embodiments A1 to A18, wherein $R^3$ is independently a hydrogen, halogen, —$CX^3{}_3$, —$CHX^3{}_2$, —$CH_2X^3$, unsubstituted $C_1$-$C_4$ alkyl, or unsubstituted 2 to 4 membered heteroalkyl.

Embodiment A22

The compound of one of embodiments A1 to A18, wherein $R^3$ is independently a halogen, —$CX^3{}_3$, —$CHX^3{}_2$, —$CH_2X^3$, unsubstituted methyl, unsubstituted ethyl, unsubstituted isopropyl, unsubstituted methoxy, or unsubstituted ethoxy.

Embodiment A23

The compound of one of embodiments A1 to A18, wherein $R^3$ is independently a —$CX^3{}_3$, —$CHX^3{}_2$, —$CH_2X^3$, unsubstituted methyl, or unsubstituted ethyl.

Embodiment A24

The compound of one of embodiments A1 to A18, wherein $R^3$ is independently a —$CX^3{}_3$, —$CHX^3{}_2$, —$CH_2X^3$, or unsubstituted methyl.

Embodiment A25

The compound of one of embodiments A1 to A18, wherein $R^3$ is independently unsubstituted methyl.

Embodiment A26

The compound of one of embodiments A1 to A25, wherein $R^4$ is independently hydrogen, —$CF_3$, or substituted or unsubstituted $C_1$-$C_4$ alkyl.

Embodiment A27

The compound of one of embodiments A1 to A25, wherein $R^4$ is independently hydrogen, —$CX^4{}_3$, —$CHX^4{}_2$, —$CH_2X^4$, unsubstituted methyl, unsubstituted ethyl, or unsubstituted isopropyl.

Embodiment A28

The compound of one of embodiments A1 to A25, wherein $R^4$ is independently a —$CX^4{}_3$, —$CHX^4{}_2$, —$CH_2X^4$, unsubstituted methyl, or unsubstituted ethyl.

Embodiment A29

The compound of one of embodiments A1 to A25, wherein $R^4$ is independently a —$CX^4{}_3$, —$CHX^4{}_2$, —$CH_2X^4$, or unsubstituted methyl.

Embodiment A30

The compound of one of embodiments A1 to A25, wherein $R^4$ is independently unsubstituted methyl.

Embodiment A31

The compound of one of embodiments A1 to A30, wherein $R^5$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment A32

The compound of one of embodiments A1 to A30, wherein $R^5$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment A33

The compound of one of embodiments A1 to A30, wherein $R^5$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment A34

The compound of one of embodiments A1 to A30, wherein $R^5$ is a hydrogen, unsubstituted $C_1$-$C_4$ alkyl.

Embodiment A35

The compound of one of embodiments A1 to A30, wherein $R^5$ is an unsubstituted methyl or unsubstituted ethyl.

Embodiment A36

The compound of one of embodiments A1 to A30, wherein $R^5$ is independently a —$CX^5_3$, —$CHX^5_2$, —$CH_2X^5$, unsubstituted methyl, or unsubstituted ethyl.

Embodiment A37

The compound of one of embodiments A1 to A30, wherein $R^5$ is independently a —$CX^5_3$, —$CHX^5_2$, —$CH_2X^5$, or unsubstituted methyl.

Embodiment A38

The compound of one of embodiments A1 to A30, wherein $R^5$ is independently unsubstituted methyl.

Embodiment A39

The compound of one of embodiments A1 to A38, wherein $R^6$ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment A40

The compound of one of embodiments A1 to A38, wherein $R^6$ is a hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment A41

The compound of one of embodiments A1 to A38, wherein $R^6$ is a hydrogen, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment A42

The compound of one of embodiments A1 to A38, wherein $R^6$ is a hydrogen, unsubstituted $C_1$-$C_4$ alkyl.

Embodiment A43

The compound of one of embodiments A1 to A38, wherein $R^6$ is an unsubstituted methyl or unsubstituted ethyl.

Embodiment A44

The compound of one of embodiments A1 to A38, wherein $R^6$ is independently a —$CX^6_3$, —$CHX^6_2$, —$CH_2X^6$, unsubstituted methyl, or unsubstituted ethyl.

Embodiment A45

The compound of one of embodiments A1 to A38, wherein $R^6$ is independently a —$CX^6_3$, —$CHX^6_2$, —$CH_2X^6$, or unsubstituted methyl.

Embodiment A46

The compound of one of embodiments A1 to A38, wherein $R^6$ is independently unsubstituted methyl.

Embodiment A47

The compound of one of embodiments A1 to A46, wherein $L^1$ is independently a bond, substituted or unsubstituted alkylene, substituted or unsubstituted alkenylene, substituted or unsubstituted heteroalkylene, or substituted or unsubstituted heteroalkenylene.

Embodiment A48

The compound of one of embodiments A1 to A46, wherein $L^1$ is independently a bond, substituted or unsubstituted $C_1$-$C_4$ alkylene, substituted or unsubstituted $C_2$-$C_4$ alkenylene, substituted or unsubstituted 2 to 4 membered heteroalkylene, or substituted or unsubstituted 3 to 4 membered heteroalkenylene.

Embodiment A49

The compound of one of embodiments A1 to A46, wherein $L^1$ is independently a bond, unsubstituted $C_1$-$C_4$ alkylene, unsubstituted $C_2$-$C_4$ alkenylene, unsubstituted 2 to 4 membered heteroalkylene, or unsubstituted 3 to 4 membered heteroalkenylene.

Embodiment A50

The compound of one of embodiments A1 to A46, wherein $L^1$ is independently an unsubstituted $C_2$-$C_3$ alkylene or unsubstituted $C_2$-$C_3$ alkenylene.

Embodiment A51

The compound of one of embodiments A1 to A46, wherein $L^1$ is independently an unsubstituted ethylene or unsubstituted ethenylene.

Embodiment A52

The compound of one of embodiments A1 to A46, wherein $L^1$ is independently

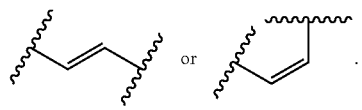

Embodiment A53

The compound of embodiment A1, wherein the compound is:

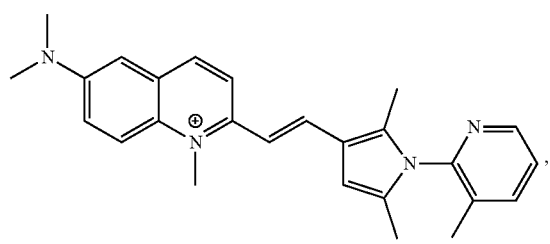

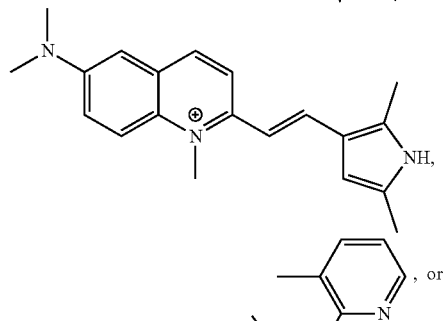

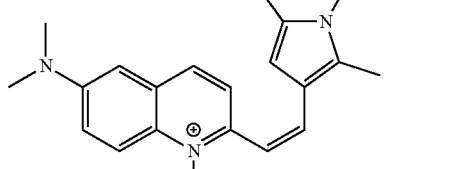

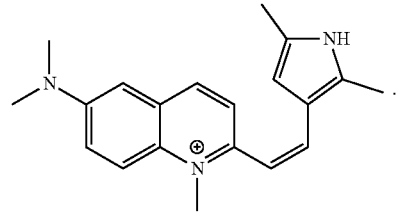

Embodiment A54

The compound of one of embodiments A1 to A53, wherein said compound is an antagonist of a nuclear receptor.

Embodiment A55

The compound of one of embodiments A1 to A53, wherein said compound is an antagonist of an androgen receptor.

Embodiment A56

A pharmaceutical composition comprising a compound of one of embodiments A1 to A53, or a pharmaceutically acceptable salt thereof, and a pharmaceutically acceptable excipient.

Embodiment A57

A method of treating a disease associated with androgen receptor activity in a patient in need of such treatment, said method comprising administering a therapeutically effective amount of a compound of one of embodiments A1 to A53, or a pharmaceutically acceptable salt thereof.

Embodiment A58

A method of treating cancer in a patient in need of such treatment, said method comprising administering a therapeutically effective amount of a compound of one of embodiments A1 to A53, or a pharmaceutically acceptable salt thereof.

Embodiment A59

The method of embodiment A58, wherein said cancer is prostate cancer.

Embodiment A60

The method of embodiment A58, wherein said cancer is hormone sensitive prostate cancer.

Embodiment A61

The method of embodiment A58, wherein said cancer is hormone refractory prostate cancer.

Embodiment A62

A method of inhibiting androgen receptor activity, said method comprising contacting an androgen receptor with an effective amount of a compound of one of embodiments A1 to A53.

H. EXAMPLES

Example 1. Compound Synthesis and Characterization

Synthesis of COHPyrv-7 tosylate, D3-COHPyrv-7 tosylate, COHPyrv-24-HES, COHPyrv-24-D3-HES.

6-Dimethylamino-1,2-dimethylquinolinium tosylate (11-146-4pp). A modification of the procedure of McDonald et al. (WO2006 078754) was used: A solution of 6-dimethylaminoquinaldine (A, 440 mg, 2.37 mmol) and methyl p-toluenesulphonate (B, 945 mg, 5.08 mmol) in 4 mL of chloroform was heated to reflux for 14 h. The solvent was evaporated and the residue was triturated twice with refluxing ethyl acetate, then cooled and filtered. The resulting crude orange precipitate (850 mg, 97% yield), mp 178-181° C. was utilized in the next step without further purification. When the reaction was conducted in refluxing ethyl acetate, similar results were obtained.

(A sample of the crude precipitate (47 mg) was purified by chromatography on silica gel (CH2Cl2—MeOH, 100:0 to 90:10) to give an orange solid (16 mg, 34% recovery), mp 192-195° C. ms, 201 (M+), 1H NMR (DMSO-d6) δ 8.71 (1H, d), 8.32 (1H, d), 7.85 (1H, d), 7.75 (1H, d), 7.48 (2H, d), 7.24 (1H, s), 7.10 (2H, d), 4.32 (3H, s), 3.10 (6H, s), 2.92 (3H, s), 2.29 (3H, s).)

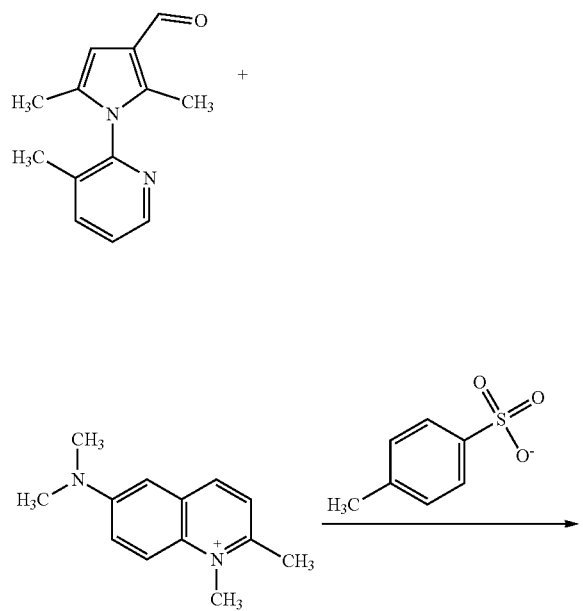

(E)-6-Di methylamino-2-(2-(2,5-dimethyl-1-(3-methyl-pyridin-2-yl)-1H-pyrrol-3-yl)ethenyl)-1-methylquinolinium tosylate (11-160-1a). COHPyrv-24 Tosylate. Crude 6-dimethylamino-1,2-dimethylquinolinium tosylate (4.00 g, 10.8 mmol) was dissolved in methanol (50 mL). 2,5-dimethyl-1-(3-methyl-1-pyridin-2-yl)-1H-pyrrol-3-carboxaldehyde (2.30 g, 10.7 mmol), piperidine (160 mg, 1.88 mmol) and 3 Å molecular sieves were added and the mixture was refluxed under molecular sieves for 24 hours in a nitrogen atmosphere. The molecular sieves were removed by decanting and the supernatant was evaporated in vacuo then chromatographed on silica gel (7×16 cm) with CH2Cl2-MeOH (100:0 to 95:5 to 93:7) to afford the product (1.39 g, 23%) as a dark red solid. ms, 397 (M−), NMR ¹H NMR (DMSO-d6) δ 8.48 (2H, ABq), 8.22 (1H, d), 8.08 (1H, d), 7.96 (1H, t), 7.61 (1H, dd), 7.47 (2H, d), 7.42 (1H, d), 7.33 (1H, d), 7.26 (1H, s), 7.22 (2H, m), 7.10 2H, d), 6.72 (1H, s), 4.37 (3H, s), 3.10 (3H, s), 2.54 (3H, s), 2.31 (3H, s), 2.28 (3H, s).

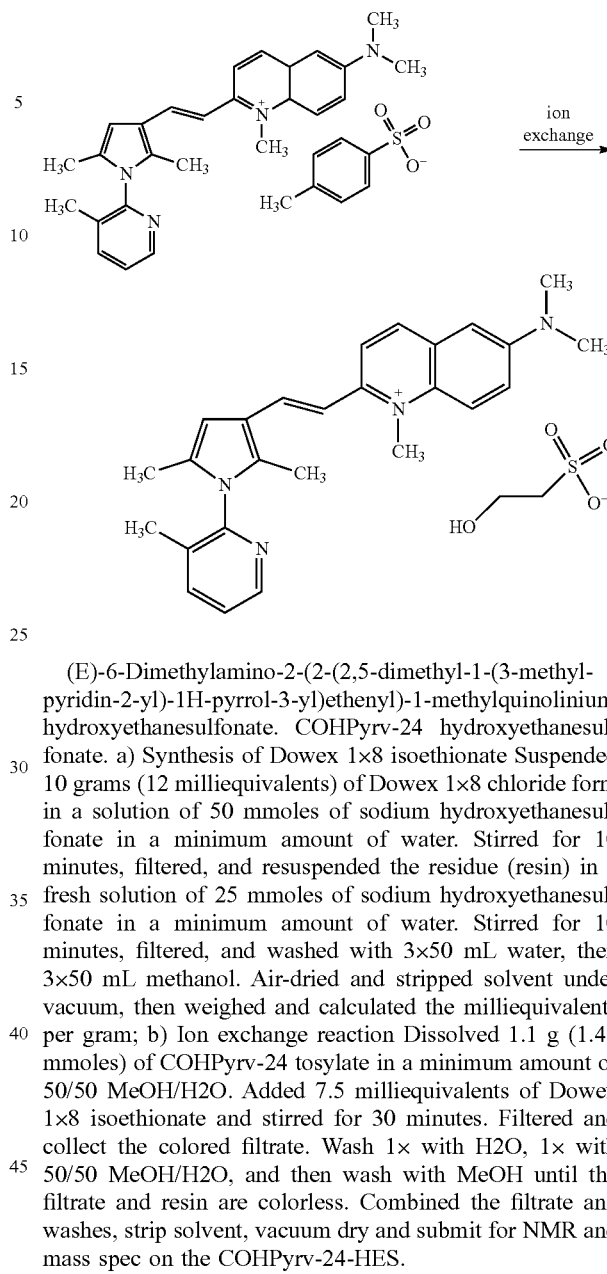

(E)-6-Dimethylamino-2-(2-(2,5-dimethyl-1-(3-methyl-pyridin-2-yl)-1H-pyrrol-3-yl)ethenyl)-1-methylquinolinium hydroxyethanesulfonate. COHPyrv-24 hydroxyethanesulfonate. a) Synthesis of Dowex 1×8 isoethionate Suspended 10 grams (12 milliequivalents) of Dowex 1×8 chloride form in a solution of 50 mmoles of sodium hydroxyethanesulfonate in a minimum amount of water. Stirred for 10 minutes, filtered, and resuspended the residue (resin) in a fresh solution of 25 mmoles of sodium hydroxyethanesulfonate in a minimum amount of water. Stirred for 10 minutes, filtered, and washed with 3×50 mL water, then 3×50 mL methanol. Air-dried and stripped solvent under vacuum, then weighed and calculated the milliequivalents per gram; b) Ion exchange reaction Dissolved 1.1 g (1.48 mmoles) of COHPyrv-24 tosylate in a minimum amount of 50/50 MeOH/H2O. Added 7.5 milliequivalents of Dowex 1×8 isoethionate and stirred for 30 minutes. Filtered and collect the colored filtrate. Wash 1× with H2O, 1× with 50/50 MeOH/H2O, and then wash with MeOH until the filtrate and resin are colorless. Combined the filtrate and washes, strip solvent, vacuum dry and submit for NMR and mass spec on the COHPyrv-24-HES.

(1-d₃)-6-Dimethylamino-1,2-dimethylquinolinium tosylate (11-158-1p). This was prepared by the same procedure from d₃-methyl p-toluenesulphonate. ms, 204 (M+), ¹H NMR as above, but no signal at 4.32 ppm.

(E)-6-Dimethylamino-2-(2-(2,5-dimethyl-1H-pyrrol-3-yl)ethenyl)-1-methylquinolinium tosylate (11-147-2a). COHPyrv-7 tosylate. Crude 6-dimethylamino-1,2-dimethylquinolinium tosylate (50 mg, 0.134 mmol) was dissolved in methanol (0.5 mL). 2,5-Dimethyl-1H-pyrrole-3-carboxaldehyde (17 mg, 0.138 mmol) and piperidine (1.7 mg, 0.02 mmol) were added and the mixture was stirred for 3 days at 70° C. The solvent was evaporated, and the residue was chromatographed on silica gel gel (CH₂Cl₂-MeOH, 100:0 to 95:5) to give a deep red solid (12 mg, 19% yield). NMR ¹H NMR (DMSO-d₆) δ 11.15 (1H, s), 8.40 (2H, ABq), 8.16 (1H, d), 7.99 (1H, d), 7.54 (1H, d), 7.46 (1H, d), 7.19 (2H, s), 7.08 (2H, d), 7.01 (1H, d), 6.38 (1H, s), 4.28 (3H, s), 3.08 (6H, s), 2.40 (3H, s), 2.29 (3H, s), 2.18 (3H, s).

(E)-6-Dimethylamino-2-(2-(2,5-dimethyl-1-(3-methyl-pyridin-2-yl)-1H-pyrrol-3-yl)ethenyl)-1-methylquinolinium tosylate (11-151-1a; 11-160-1a). COHPyrv-24. Prepared by the same procedure as COHPyrv-7 from 2,5-dimethyl-1-(3-methyl-1-pyridin-2-yl)-1H-pyrrol-3-carboxaldehyde. Deep red solid (19% yield). ms, 397 (M+), NMR $^1$H NMR (DMSO-d$_6$) δ 8.48 (2H, ABq), 8.22 (1H, d), 8.08 (1H, d), 7.96 (1H, t), 7.61 (1H, dd), 7.47 (2H, d), 7.42 (1H, d), 7.33 (1H, d), 7.26 (1H, s), 7.22 (2H, m), 7.102H, d), 6.72 (1H, s), 4.37 (3H, s), 3.10 (3H, s), 2.54 (3H, s), 2.31 (3H, s), 2.28 (3H, s).

(1-d$_3$)-(E)-6-Dimethylamino-2-(2-(2,5-dimethyl-1-(3-methylpyridin-2-yl)-1H-pyrrol-3-yl)ethenyl)-1-methylquinolinium tosylate (11-151-1a). COHPyrv-24-D3 tosylate. Prepared by the same procedure as the non-deuterated compound. Deep red solid (19% yield). ms, 400 (M+), NMR $^1$H NMR (DMSO-d$_6$) as above but no signal at 4.37 ppm.

(E)-6-Dimethylamino-2-(2-(2,5-dimethyl-1-(3-methyl-pyridin-2-yl)-1H-pyrrol-3-yl)ethenyl)-1-methylquinolinium isethionate COH Pyrv-24 hydroxyethanesulfonate.

Preparation of Dowex 1×8 HES. Dowex 1×8 Cl (5 g) was suspended in a minimum amount of water (10 mL), stirred for 10 min and filtered. The residue was suspended in a freshly prepared sodium isethionate (3.7 g, 25 mmol) solution in water (10 mL). The mixture was stirred for 10 min, filtered and the residue was washed with water (50 mL×3) and methanol (50 mL×3) successively. The resin was dried by vacuum suction for 15 min to give Dowex 1×8 isethionate (4.0 g, 0.96 milliequivalent/g).

Synthesis of COHPyrv-24-HES. To a solution of CoHPyrv-24 (30 mg, 0.04 mmol) in 50:50, MeOH:H$_2$O (1.5 mL) was added Dowex 1×8 isoethionate (0.21 g, 0.2 meq) and the mixture was stirred at room temperature for 30 min. The resulting mixture was then filtered and washed with water, 50:50 MeOH/H2O and MeOH successively (50 mL total vol.) until the resin turned colorless. The filtrate was concentrated and dried under high vacuum to give 29 mg of the title compound.

Large scale synthesis of COHPyrv-24-HES. To a solution of CoHPyrv-24 (1.1 g, 1.9 mmol) in 50:50, MeOH:H$_2$O (25 mL) was added Dowex 1×8 isoethionate (0.21 g, 0.2 meq) and the resulting mixture was stirred at room temperature for 30 min. The resulting mixture was then filtered and washed with water, 50:50 MeOH/H2O and MeOH successively until the resin turned colorless. The combined filtrate was concentrated and dried under high vacuum to give 0.99 g of the title compound. MS calculated for C$_{30}$H$_{40}$N$_4$O$_8$S$_2$: 648.23, found 647 (M-H)$^-$, 398 (M+-HES). $^1$H NMR (499 MHz, Methanol-d4) δ 8.45 (d, J=9.1 Hz, 1H), 8.20 (dd, J=23.3, 9.4 Hz, 2H), 8.05-7.92 (m, 2H), 7.64 (dd, J=9.7, 3.0 Hz, 1H), 7.44 (dd, J=17.5, 7.7 Hz, 1H), 7.28-7.13 (m, 4H), 6.59 (d, J=1.3 Hz, 1H), 4.40 (s, 3H), 3.92 (t, J=6.9 Hz, 2H), 3.35 (s, 3H), 3.20 (s, 1H), 3.17 (s, 6H), 3.06-2.99 (m, 2H), 2.61 (s, 3H), 2.30 (s, 3H), 2.11 (d, J=1.0 Hz, 3H).

Solubility: 10 mg/mL in MeOH, 6 mg/mL in DMSO and 2.5 mg/mL EtOH

Synthesis of COHPyrv-24-D3-HES. To a solution of CoHPyrv-24-D3 tosylate (30 mg, 0.05 mmol) in 50:50, MeOH:H$_2$O (4 mL) was added Dowex 1×8 isoethionate (0.21 g, 0.2 meq) and the mixture was stirred at room temperature for 30 min. The resulting mixture was then filtered and washed with water, 50:50 MeOH/H2O and MeOH successively until the resin turned colorless. The combined filtrate was concentrated and dried under high vacuum to give 26.8 mg of the title compound. MS calculated for C28H31D3N4O4S: 525.25, found 400.7 (M+-HES). $^1$H NMR (499 MHz, Methanol-d4) δ 8.45 (d, J=9.1 Hz, 1H), 8.20 (dd, J=27.1, 9.5 Hz, 2H), 8.05-7.91 (m, 2H), 7.64 (dd, J=9.7, 3.0 Hz, 1H), 7.51-7.40 (m, 1H), 7.30-7.12 (m, 3H), 6.59 (d, J=1.2 Hz, 1H), 4.56 (s, 1H), 3.92 (t, J=6.9 Hz, 2H), 3.35 (s, 2H), 3.17 (s, 6H), 3.03 (t, J=7.0 Hz, 3H), 2.60 (s, 3H), 2.30 (s, 3H), 2.11 (d, J=1.0 Hz, 3H).

Compound characterization includes AR inhibition Luciferase assays, IC$_{50}$ determination in PC cell lines, synergy with competitive antagonist, activity against AR splice variants (Transfected ARvs and 22Rv1 cells), specificity for the DNA binding domain, AR inhibitor tested with in vivo qPCR, in vivo inhibition of AR-regulated genes in mouse prostate and human PC xenograft tissue (qPCR) characterized; PC growth antagonism tested with growth curves in AR+ and AR− PC cell lines, growth curve in enzalutamide-resistant cell line, inhibition of LNCaP xenograft growth in vivo; solubility characterized in various solutions; toxicity measured with single dose and once daily dosing MTD determination by various routes; pharmacokinetics characterized by IV, IP, oral for various preparations.

Summary of structure, name, MW, AR inhibitory potential (nM) and LNCaP growth inhibition (300 nM) is tabulated following.

| Structure (salt of compound) | Name of compound | MW | AR inhibitory potential (nM) | LNCaP growth inhibition at 300 nM |
|---|---|---|---|---|
| (structure shown) | COH Pyrv-7, COHP7, P7 | 477.62 | ~500 nM | 100% |

-continued

| Structure (salt of compound) | Name of compound | MW | AR inhibitory potential (nM) | LNCaP growth inhibition at 300 nM |
|---|---|---|---|---|
| [structure] | COH Pyrv-24, COHP24, P24 | 740.93 | ~454 nM | 100% |

Figure 3:
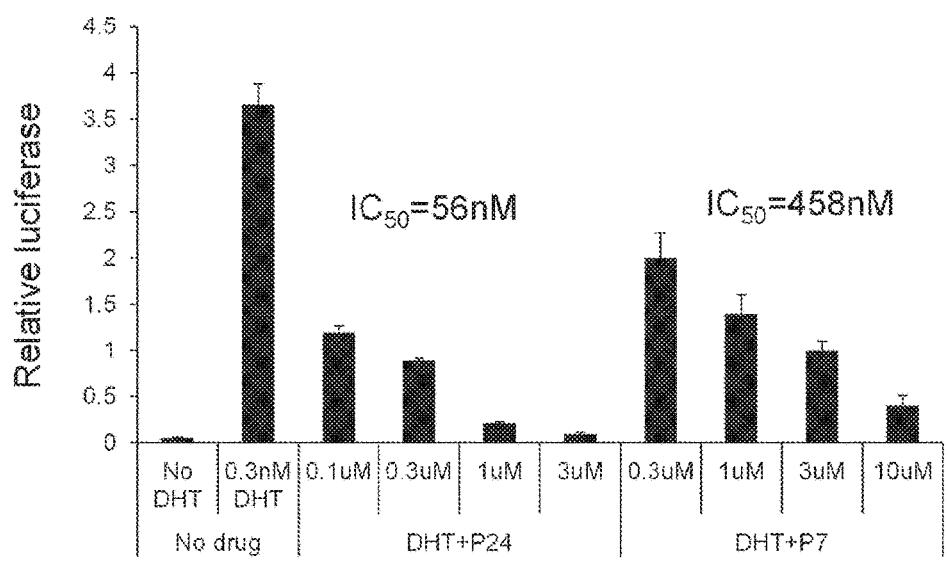
FIG. 3. Luciferase assay $IC_{50}$ determination and synergy with bicalutamide. See Example 2.

Example 2. Luciferase Assay $IC_{50}$ Determination and Synergy with Bicalutamide As depicted in FIG. 3, relative luciferase activity was used to determine IC50 values under conditions of no drug, HDT+p24 and DHT+p7. For all transfections, pools of LNCaP cells were transfected using Lipofectamine Plus (Invitrogen) with pRL-SV40 (Promega) and PSA-luciferase. The following day, the cells were replated, drugs were added, and 24 hrs later luciferase production was measured (Dual luciferase assay kit, Promega). Mean-effect plots (log[compound] vs log[fractional effect]) were generated to determine the $IC_{50}$ values for each compound or combinations of compounds at constant ratios. Microsoft Excel was used to calculate the statistics for a line using the "least squares" method. The F statistic was used to determine whether the observed relationship between the dependent and independent variables occurred by chance. Only data with an $r^2$ value greater than 0.95 and an F value that was greater than that indicated by the F table for alpha=0.05 were used for analysis. The methods of Chou and Talalay were used to determine whether two compounds had antagonistic, additive, or synergistic reactions toward each other (13). Briefly, a combination index (CI) was established for a range of fractional effects, where a CI~1 indicates additivity, CI>1 indicates antagonism, and a CI<1 indicates synergy. The CI's were based upon a non-exclusive assumption, which was indicated by the slope of the line of the combination of drugs from the mean-effect plot. However, CI's based upon an exclusive assumption were similar. The table of FIG. 3 tabulated the drug combination, cell type, expected IC50, actual (observed) IC50, and combination index at f50, under the assumption of mutually non-exclusivity.

Example 3. Activity Against AR Splice Variants

Figure 4A:
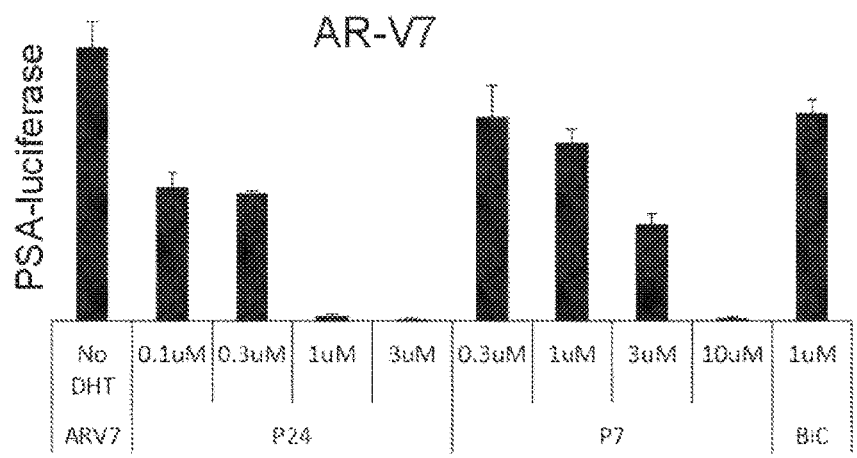
FIGS. 4A-4B. Activity against AR splice variants.
Figure 4B:
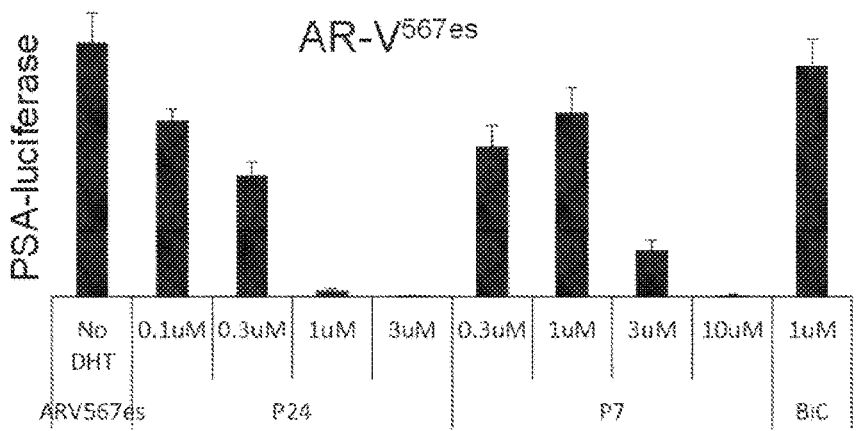

Activity against AR splice variants was determined for AR-V7 (FIG. 4A) and AR-V$^{567es}$ (FIG. 4B). 1-2 days prior to transfection, cells were placed in media containing charcoal-stripped serum. For all transfections, pools of LNCaP cells were transfected using Lipofectamine Plus (Invitrogen) with PSA-luciferase and AR variant expression plasmids. The following day, the cells were plated in quadruplicate with indicated drugs (BiC=bicalutamide) in 96 well plates. 24 hrs later luciferase production was measured (Dual luciferase assay kit, Promega). As is evident, the competitive antagonist BiC had no ability to inhibit ARv-mediated transcription of the luciferase reporter while the non-competitive AR inhibitors COH-P7 and P24 did.

Example 4. Specificity for DNA Binding Domain 1-2 days prior to transfection, cells were placed in media containing charcoal-stripped serum. For all transfections, pools of LNCaP cells were transfected using Lipofectamine Plus (Invitrogen) with PSA-luciferase or LexA-luciferase reporter plasmids and, where indicated, ARNTD-Lex-ADBD-ARLBD expression plasmid. The following day, the cells were plated in quadruplicate with indicated drugs (BiC=bicalutamide) in 96 well plates. 24 hrs later luciferase production was measured (Dual luciferase assay kit, Promega). As is evident, P7 and P24 do not inhibit the transcriptional activity of an AR construct with the DBD replaced with that of the LexA protein but BiC does.

Example 5. Inhibition of AR Activity In Vivo

Total RNA was isolated from homogenized prostate or tumor tissue using an RNAeasy kit (Qiagen). RNA was reverse-transcribed (MMLV-RT; Invitrogen), and the expression of androgen-regulated genes was assessed by qPCR using a StepOne Real Time PCR System (Applied Biosystems), using SYBR green (Invitrogen) as the detecting dye and Rox (Invitrogen) as the reference dye. Differences between treated (x) and no DHT control (y) samples were normalized to RPL19 transcript levels (i.e., androgen-unresponsive) and determined with the following calculation: (2[Ctxgene1−Ctygene1])/(2[CtxRPL19−CtyRPL19]). ANOVA methods were used to determine statistically significant differences among the groups using a Tukey test for planned comparisons. qRT-PCR of prostate tissues demonstrates inhibition of AR target genes.

Example 6. Inhibition of PC Cell Growth in Culture

For growth curves, cells were transferred to charcoal-stripped media three days before they were split and plated at a density of approximately 20,000 cells/well in 48 well plates, in quadruplicate. The assay was repeated three times. The following day, medium with the indicated drugs was added to the cells. Proliferation was determined by measuring the DNA content of the cells in each well. Each day, the cells were fixed in 100% cold methanol, followed by staining for 5 min at RT with 0.2 ng/mL 4',6-diamidino-2-phenylindole (DAPI) in PBS. The cells were washed with PBS, then read on a fluorescence plate reader (FPR) using 365/439 excitation/emission wavelengths. A student's T test was used to determine significant differences among populations. Androgen dependent LNCaP cells responded to DHT and were inhibited by P24, P7 and enzalutamide (enz). Androgen-independent, AR splice variant expressing 22Rv1 cells did not respond to DHT, as expected, and were inhibited by P24, P7, but not the competitive antagonist enz. DU145 cells are an AR-negative prostate cancer cell line used as a toxicity control and to demonstrate the on target effect of AR inhibitors; they were not significantly inhibited by any drug treatment.

Example 7. Inhibition of Xenograft Growth In Vivo

Figure 5:
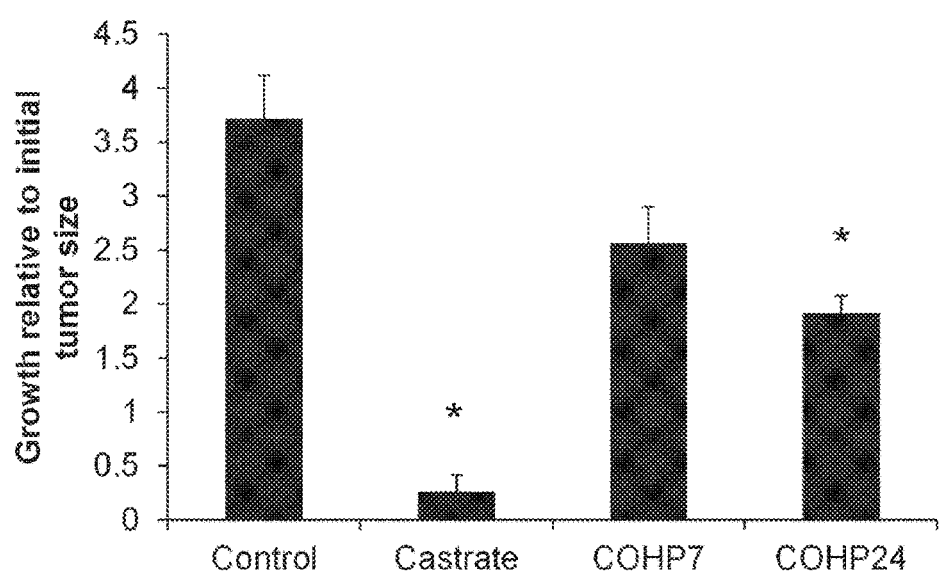
FIG. 5. Inhibition of xenograft growth in vivo; Y-axis: relative growth with respect to initial tumor size. Assay conditions (left to right): control, castrate, COHP7, and COHP24. See Example 7.

FIG. 5 depicts the effect of control, castrate, COHP7 and COHP24 on growth relative to inibital tumor size. All animal experiments were approved by the City of Hope IACUC. Male nude mice were injected with $2\times10^6$ LNCaP cells mixed with matrigel (1:1) subcutaneously into the dorsal flank. At the onset of palpable tumor (2-3 weeks), an osmotic pump (Alzet 1004) designed to deliver 5 mg/kg/day of P7 or P24 in 100 mg/ml hydroxypropyl beta cyclodextrin was implanted in the intraperitoneal cavity. Tumor growth was measured weekly by caliper until the tumor reached 15 mm in diameter (IACUC endpoint) or the pump expired (four weeks), at which point animals were euthanized and organs and tumors harvested for downstream analysis. Tumor volume was estimated by the formula: $V=\pi/6*f(l*w)^{3/2}$. Growth rate was determined by the percent increase over initial tumor volume over time. ANOVA methods were used to determine statistically significant differences among the groups using the final growth rate measurement for each animal.

Example 8. Solubility and $IC_{50}$ Studies

IC50 and solubility data (mg/mL) for pyrvinium, P7 and P24 for DMSO, acetonitrile, ethanol, buffer B (aqueous), beta-cyclodextrin, and gamma-cyclodextrin are tabulated following. IC50 activity in PCA-luciferase activity assay is an average of 5+ experiments in LNCaP and LAPC4 cells.

| Drug | $IC_{50}$ | Solubility (mg/ml) | | | | | |
|---|---|---|---|---|---|---|---|
| | | DMSO | Acetonitrile | Ethanol | Buffer B (aqueous) | Beta cyclodextrin | Gamma cyclodextrin |
| Pyrvinium | ~50 nM | ~10 | <5 | <1 | <1 | <1 | <1 |
| P7 | ~450 nM | ~10 | <5 | ~5 | <5 | ~5 | ~5 |
| P24 | ~150 nM | ~10 | <5 | ~5 | >10 | 50-100 | ~50 |

Example 9. Toxicity Studies

Toxicity studies demonstrate that P7 & P24 show similar tox profiles. In DMSO/PBS formulation, with MTD single dose: IV: ~1 mg/kg; PO (oral): not determined due to poor absorption; and IP: ~5 mg/kg. With MTD daily dosing: IP: ~1 mg/kg. In Beta cyclodextrin formulation: MTD single dose: IV: not determined; PO (oral); ~200 mg/kg; IP: >10 mg/kg. In MTD daily dosing: IP: at least 5 mg/kg; PO: at least 100 mg/kg.

Example 10. Initial Single Dose PK: DMSO/PBS Formulation

Figure 6A:
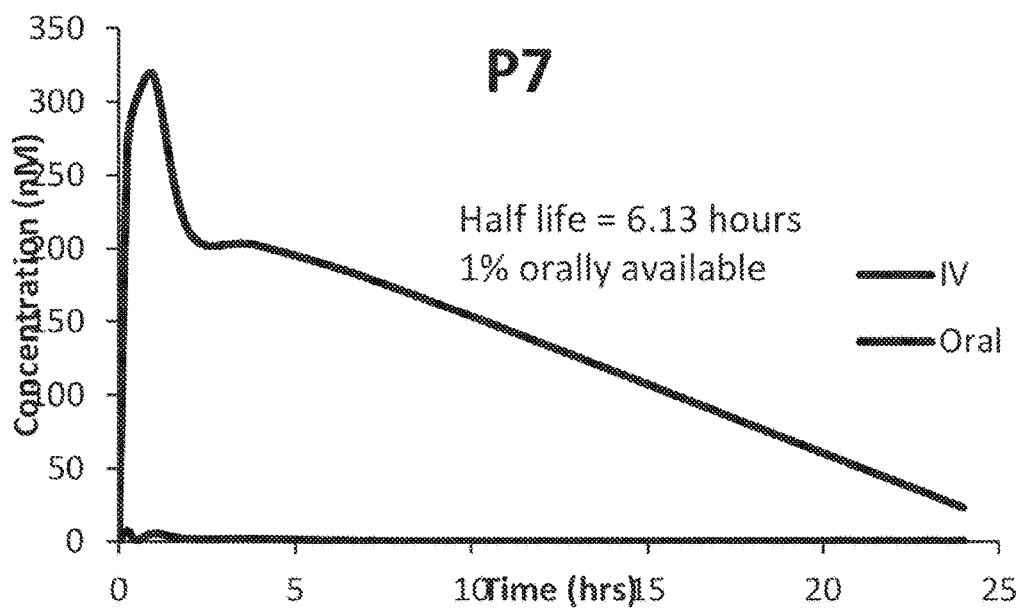
FIG. 6A-6B. Initial single dose PK: DMSO/PBS formulation.
Figure 6B:
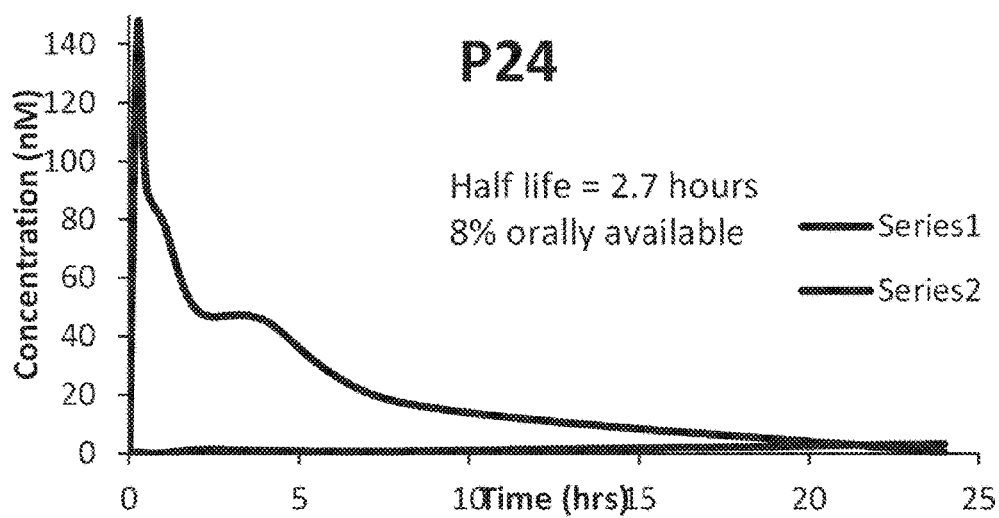

As depicted in FIG. 6A (P7) and FIG. 6B (P24), single dose PK studies were conducted for the DMSO/PBS formulation. C57/B6 mice (n=3/time point) were dosed IV or PO (oral gavage) with 1 mg/kg P7 or P24. Cardiac blood was harvested at 15 min, 30 min, 1 hr, 2 hr, 4 hr, 8 hr, 24 hr and P7 and P24 were quantified by specific and sensitive LC-MS/MS methods developed at the City of Hope Analytical Pharmacology Core facility.

Example 11. Further PK Studies

Figure 7:
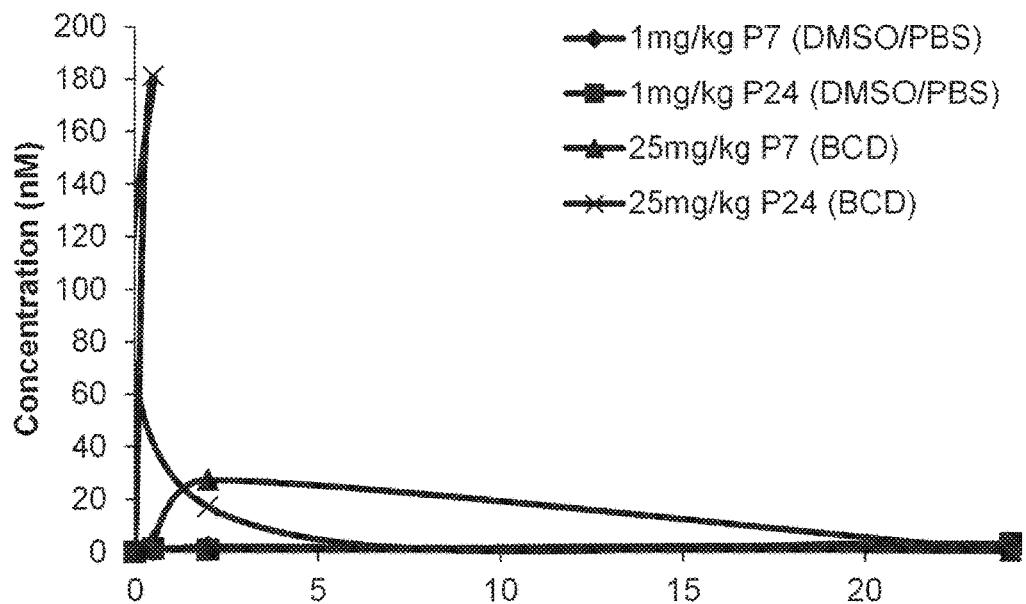
FIG. 7. Pharmacokinetic studies of P7 (1 mg/kg in DMSO/PBS) (diamonds); P24 (1 mg/kg in DMSO/PBS) (squares); P7 (25 mg/kg in BCD) (triangles); and P24 (25 mg/kg in BCD) (crosses).
Figure 8:
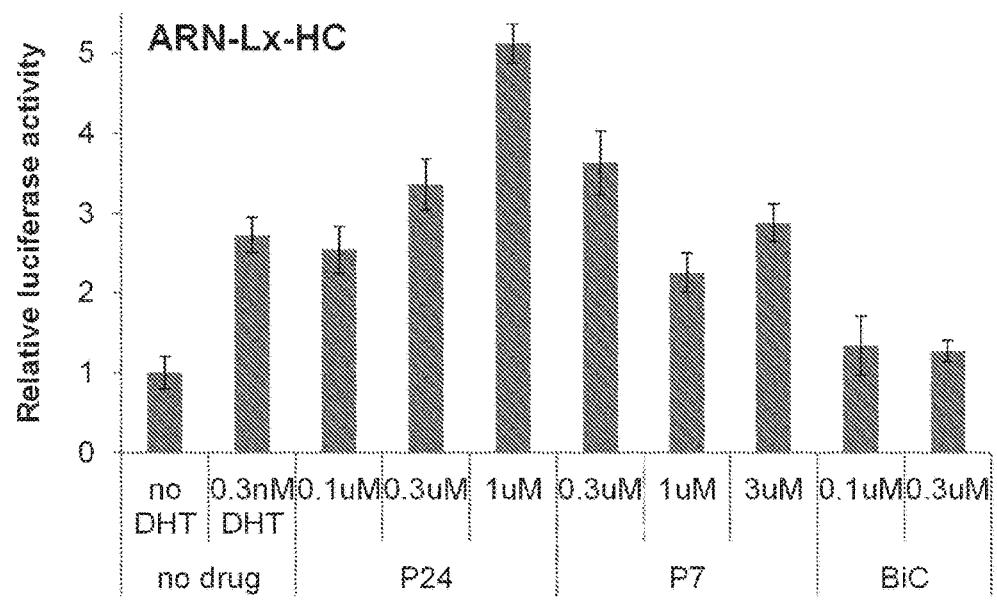
FIG. 8. Specificity for DNA domain; Neither P7 nor P24 inhibit the activity of an AR construct with the DBD substituted with that of the LexA protein while bicalutamide does inhibit such a construct.
Figure 9:
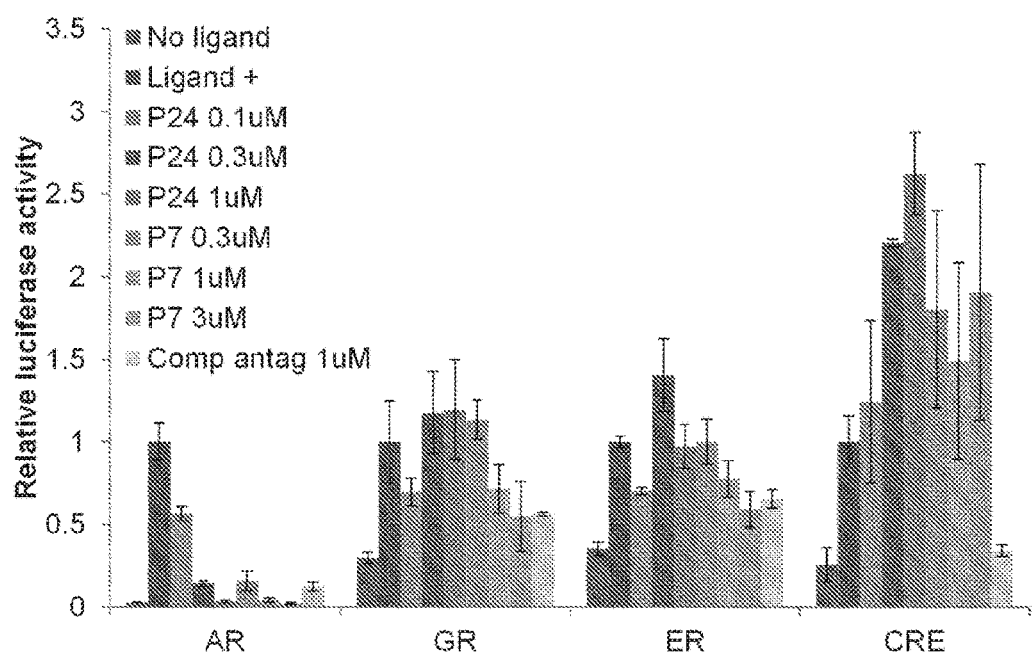
FIG. 9. Specificity for AR; P7 and P24 showing little activity against other nuclear receptors; legend top to bottom corresponds to graph left to right (No ligand, ligand+, ligand+P24 0.1 µM, ligand+P24 0.3 µM, ligand+P24 1 µM, ligand+P7 0.3 µM, ligand+P7 1 µM, ligand+P7 3 µM, comparison antagonist 1 µM).
Figure 10:
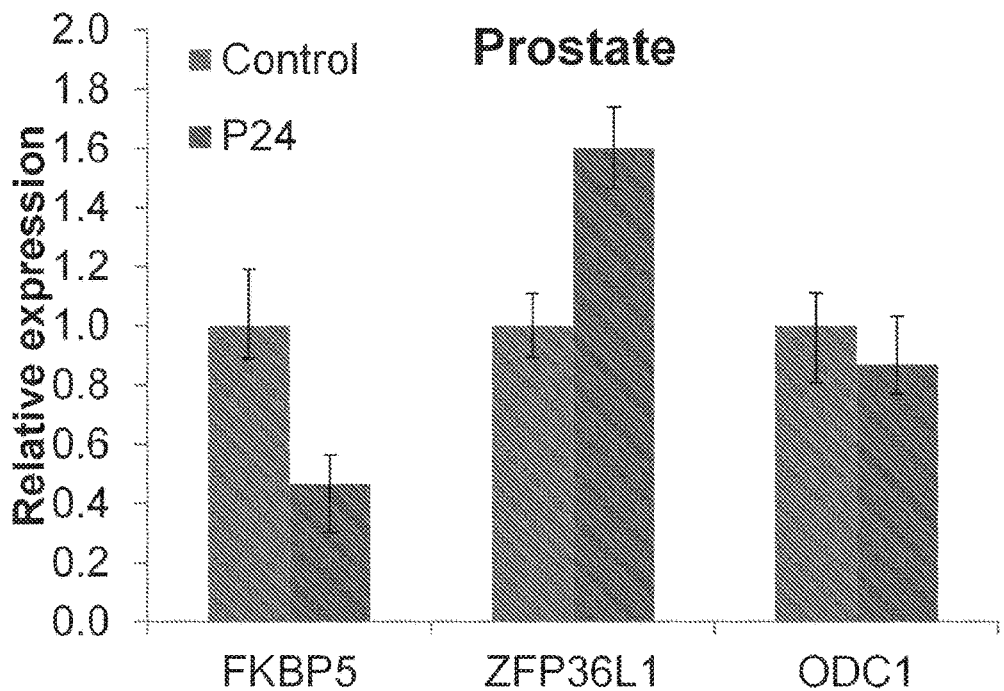
FIG. 10. Inhibition of AR activity in vivo; Mice (n=6) were treated with 5 mg/kg P24 via osmotic pump for 4 weeks; qRT-PCR of prostate tissue demonstrates inhibition of AR target genes.
Figure 11:
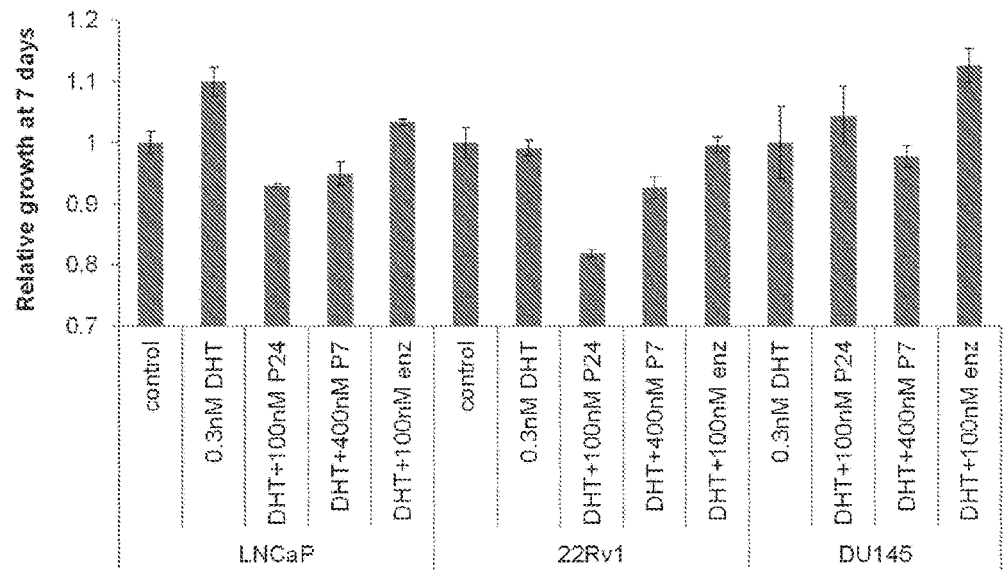
FIG. 11. Inhibition of PC cell growth in culture; P7 and P24 inhibit the growth of AR-dependent LNCaP, 22Rv1, but not AR-independent DU145 cells.
Figure 12:
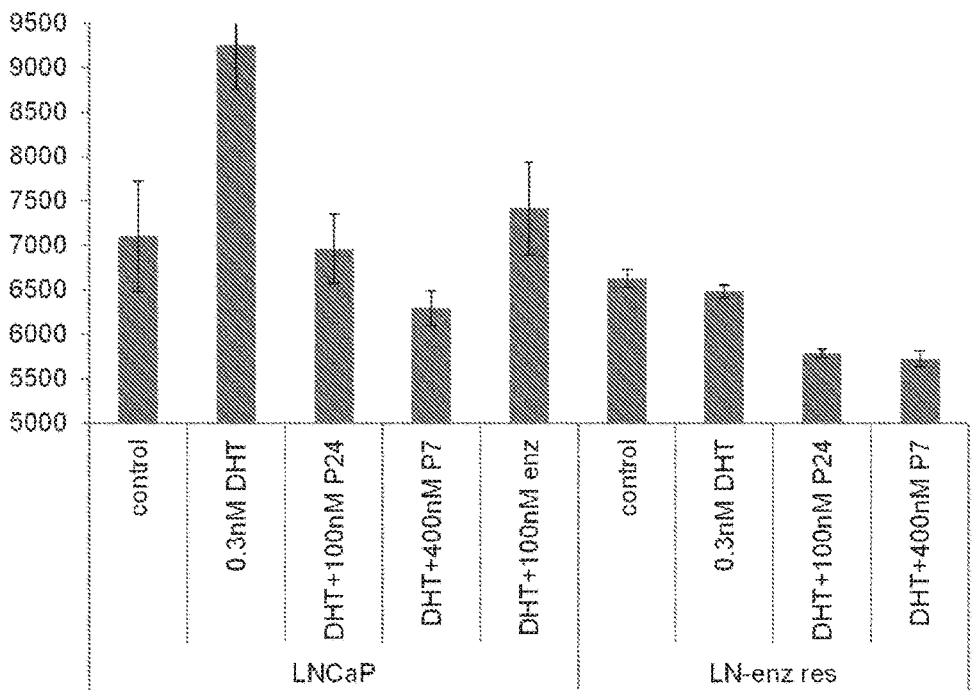
FIG. 12. Inhibition of PC cell growth in culture; P7 and P24 inhibit the growth of enzalutamide (enz)-resistant LNCaP cells (this cell line does not have additional AR mutations).
Figure 13:
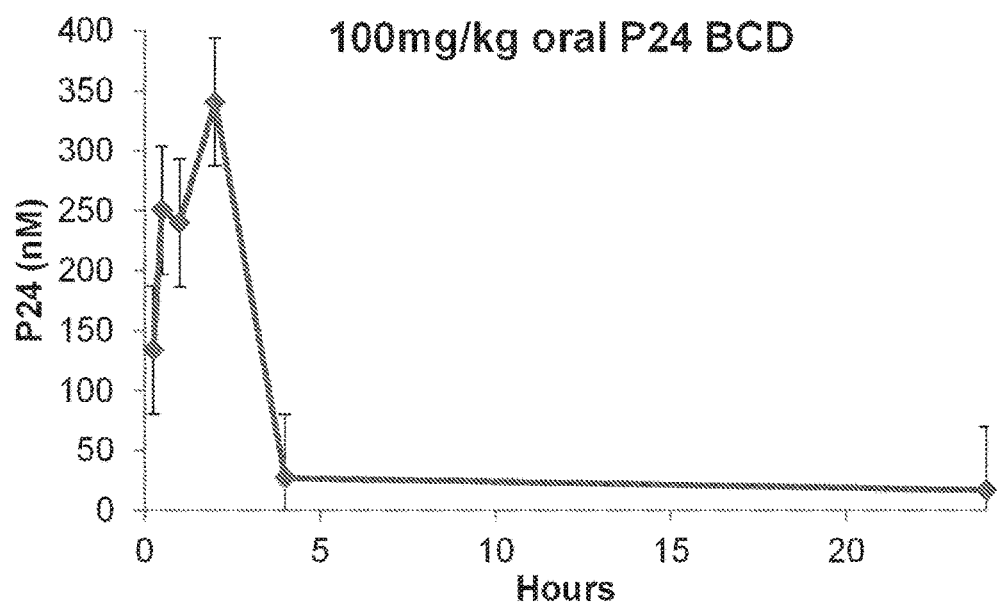
FIG. 13. P24 half-life as measured with 100 mg/kg oral P24 BCD.

As depicted in FIG. 7, further PK studies were conducted on P7 and P24 in either DMSO/PBS or BCD formulation. Treatment: 1-2 mice with single dose and blood at 0.5, 2 and 24-hrs. These results indicate that there is a significant spike in P24 initially after administration in BCD formulation. In contrast, there is a more continuous peak of P7 in BCD formulation. There is observed almost no drug in DMSO/PBS formulation. 100 mg/kg P24 PO PK study ongoing.

Example 12. Residues K609 and P612 of AR are Important for Compound Binding (P24)

Figure 14:
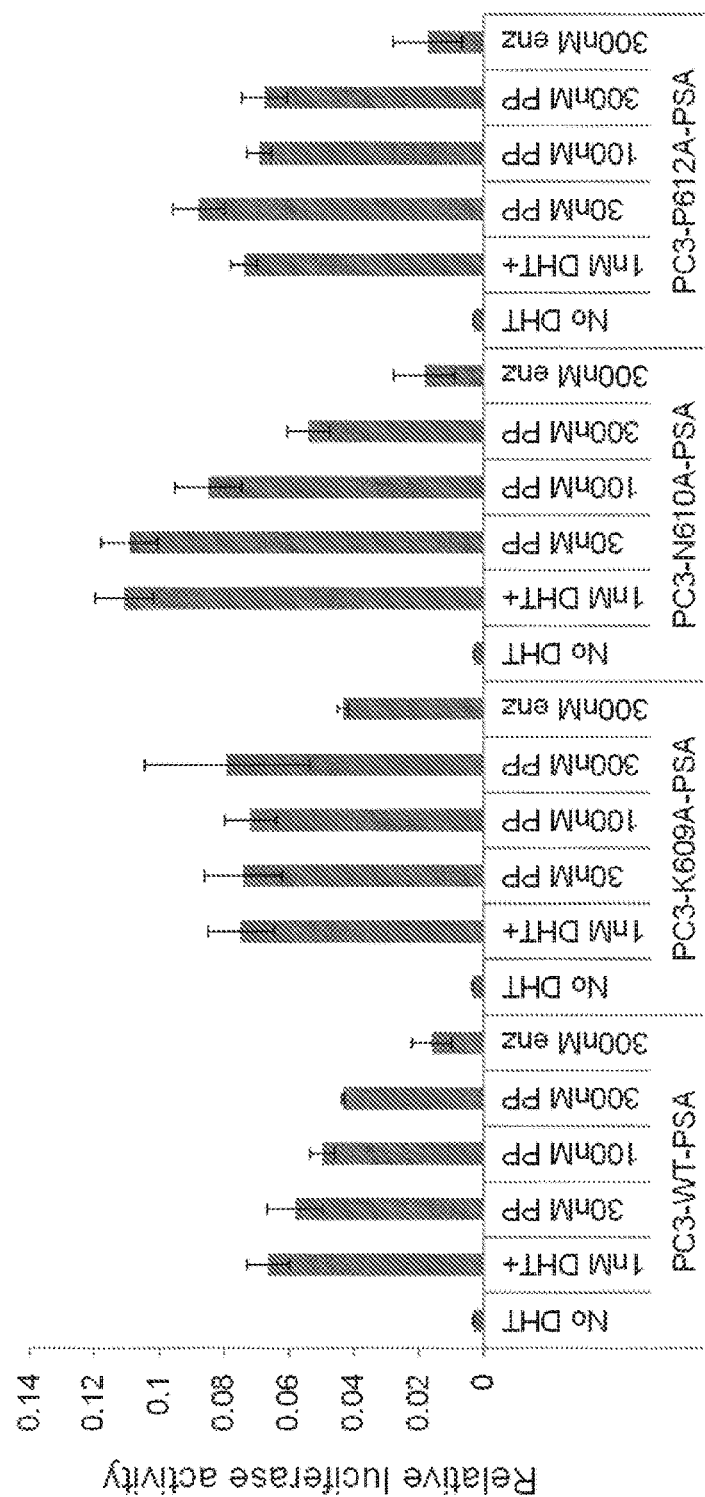
FIG. 14. Residues K609 and P612 are important for compound binding.

As depicted in FIG. 14, alanine scanning mutations. For all transfections, pools of PC3 cells were transfected using Lipofectamine Plus (Invitrogen) with PSA-luciferase and AR mutant plasmids. The following day, the cells were plated in quadruplicate with indicated drugs (enz=enzalutamide) in 96 well plates. 24 hrs later luciferase production was measured (Dual luciferase assay kit, Promega).

Example 13. Inhibition of 22Rv1 Xenograft Growth In Vivo

Figure 15:
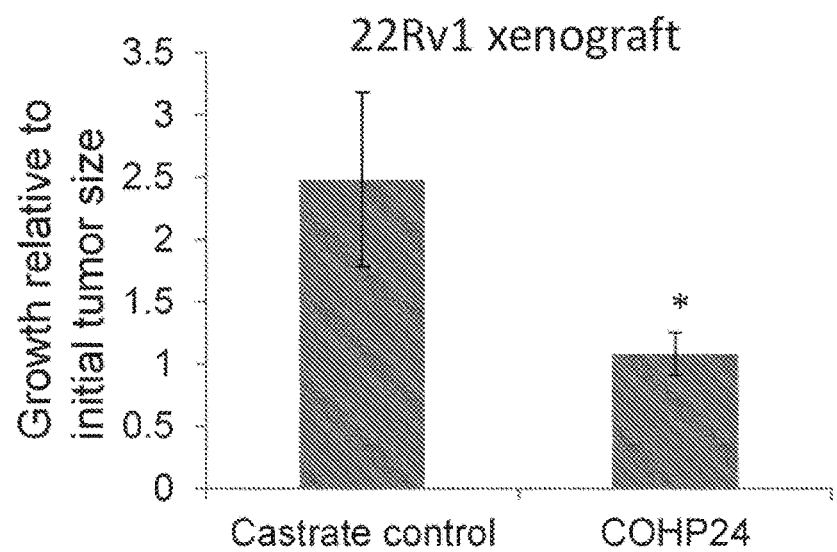
FIG. 15. Inhibition of 22Rv1 xenograft growth in vivo.

As depicted in FIG. 15, 22Rv1 cells are a model for envisioned clinical space for compounds. 22Rv1 cells are castration resistant prostate cancer cells with constitutive expression of ARV-7. All animal experiments were approved by the City of Hope IACUC. Male nude mice were injected with $2\times10^6$ 22Rv1 cells mixed with matrigel (1:1) subcutaneously into the dorsal flank. At the onset of palpable tumor (2-3 weeks), 30 mg/kg of P24 in 100 mg/ml hydroxypropyl beta cyclodextrin was given by oral gavage, twice daily. Tumor growth was measured weekly by caliper until the tumor reached 15 mm in diameter (IACUC endpoint) or for four weeks, at which point animals were euthanized and organs and tumors harvested for downstream analysis. Tumor volume was estimated by the formula: $V=\pi/6*f$ $(l*w)^{3/2}$ (51). Growth rate was determined by the percent increase over initial tumor volume over time.

Example 14. P24 Microsomal Analysis

As depicted in FIG. 16, the concentration of compound. P24 solution tested with incubation with microsomes. Human or mouse microsomes were incubated with 100 ng/ml P24 for the indicated times in the presence or absence of NADPH, at which point, P24 was quantified by LC-MS/MS. NADPH dependent demonstrates that it is a CYPP450 dependent metabolism. The lack of breakdown without NADPH demonstrates chemical stability.

Example 15. P24 Metabolites

Figure 17:
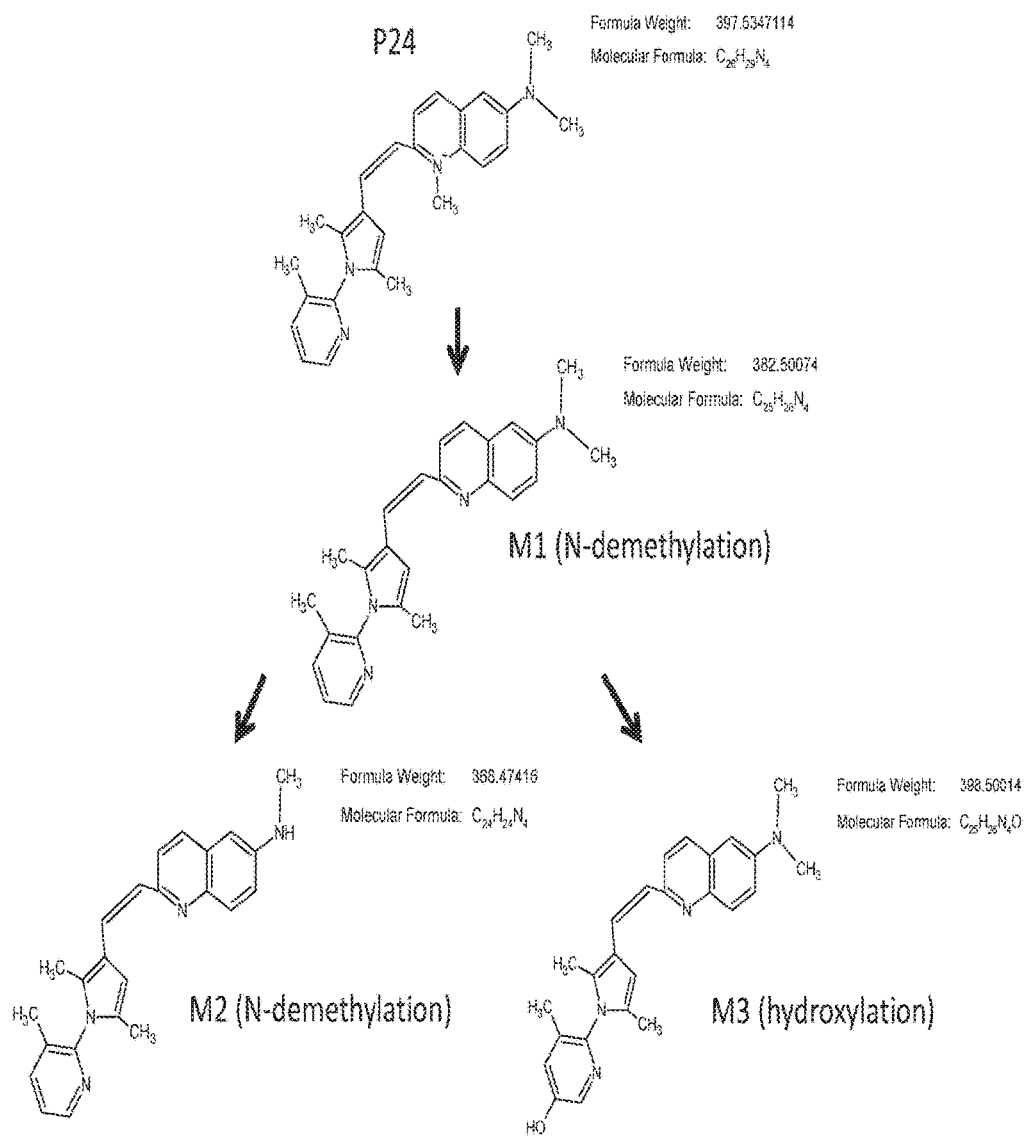
FIG. 17. P24 metabolites.
Figure 18:
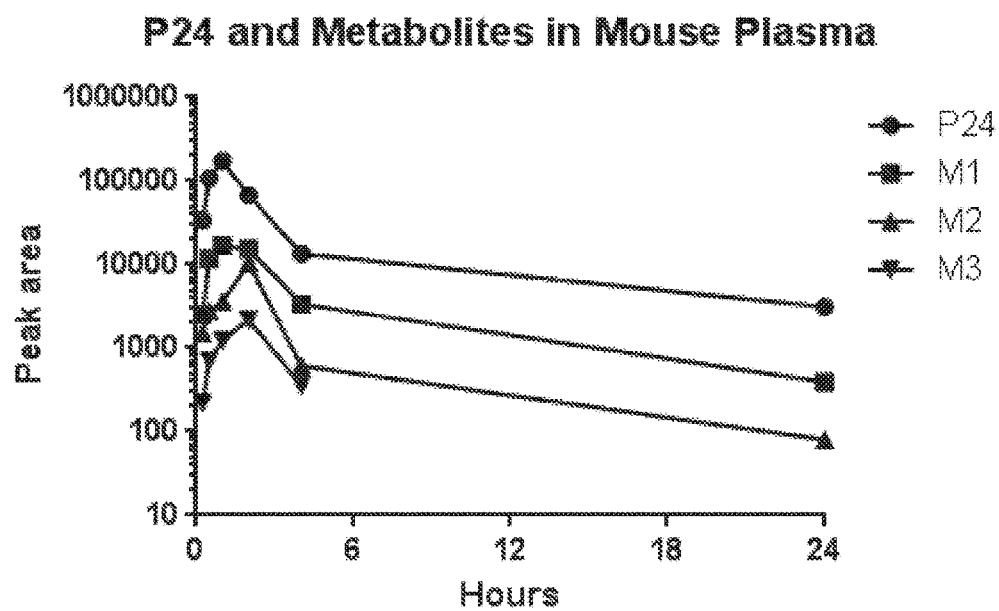
FIG. 18. P24 and metabolites shown in FIG. 17 in mouse plasma.

As depicted in FIG. 17, the predicted metabolites of P24 based on microsomal analysis. FIG. 18 shows a PK study of metabolites in mouse plasma (from associated PK study of P24) and amounts of P24 and metabolites in mouse plasma over time.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A compound, or a pharmaceutically acceptable salt thereof, having the formula:

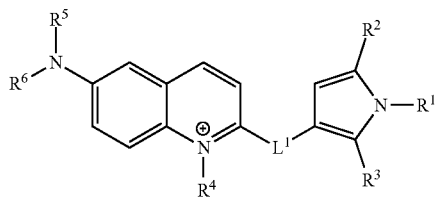

(I)

wherein
R$^1$ is hydrogen or substituted or unsubstituted pyrid-2-yl;
R$^2$ is independently a hydrogen, halogen, —CX$^2_3$, —CHX$^2_2$, —CH$_2$X$^2$, —CN, —SO$_{n2}$R$^{10}$, —SO$_{v2}$NR$^7$R$^8$, —NHNR$^7$R$^8$, —ONR$^7$R$^8$, —NHC=(O)NHNR$^7$R$^8$, —NHC=(O)NR$^7$R$^8$, —N(O)$_{m2}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C=(O)R$^9$, —NR$^7$C(O)—OR$^9$, —NR$^7$OR$^9$, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is independently a hydrogen, halogen, —CX$^3_3$, —CHX$^3_2$, —CH$_2$X$^3$, —CN, —SO$_{n3}$R$^{14}$, —SO$_{v3}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m3}$, —NR$^{11}$R$^{12}$, —C(O)R$^{13}$, —C(O)—OR$^{13}$, —C(O)NR$^{11}$R$^{12}$, —OR$^{14}$, —NR$^{11}$SO$_2$R$^{14}$, —NR$^{11}$C=(O)R$^{13}$, —NR$^{11}$C(O)—OR$^{13}$, —NR$^{11}$OR$^{13}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^7$, R$^8$, R$^9$, R$^{10}$, R$^{11}$, R$^{12}$, R$^{13}$ and R$^{14}$ are independently hydrogen, halogen, —CX$_3$, —CHX$_2$, —CH$_2$X, —OCX$_3$, —OCHX$_2$, —OCH$_2$X, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl;
R$^4$ is independently hydrogen, a —CX$^4_3$, —CHX$^4_2$, —CH$_2$X$^4$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is independently a hydrogen, halogen, —CX$^5_3$, —CHX$^5_2$, —CH$_2$X$^5$, —CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^6$ is independently a hydrogen, halogen, —CX$^6_3$, —CHX$^6_2$, —CH$_2$X$^6$—CN, —C(O)H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
L1 is independently a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene;
m2, m3, v2, and v3 are independently 1 or 2;
n2 and n3 are independently an integer from 0 to 4;
X$^1$, X$^2$, X$^3$, X$^4$, X$^5$, and X$^6$ are independently —Cl, —Br, —I, or —F.

2. The compound of claim 1, having the formula:

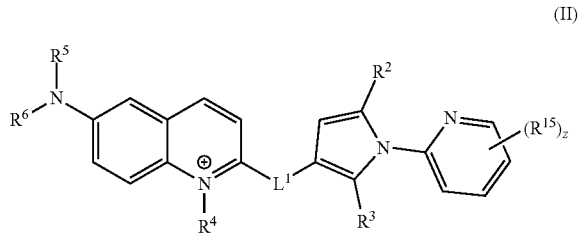

(II)

wherein
R$^{15}$ is independently a halogen, —CX$^{15}_3$, —CHX$^{15}_2$, —CH$_2^{15}$, —CN, —SO$_{n15}$R$^{19}$, —SO$_{v15}$NR$^{16}$R$^{17}$, —NHNR$^{16}$R$^{17}$, —ONR$^{16}$R$^{17}$, —NHC=(O)NHNR$^{16}$R$^{17}$, —NHC=(O)NR$^{16}$R$^{17}$, —N(O)$_{m15}$, —NR$^{16}$R$^{17}$, —C(O)R$^{18}$, —C(O)—OR$^{18}$, —C(O)NR$^{16}$R$^{17}$, —NR$^{16}$SO$_2$R$^{19}$, —NR$^{16}$C=(O)R$^{18}$, —NR$^{16}$C(O)OR$^{18}$, —NR$^{16}$OR$^{18}$, —OCX$^{15}_3$, —OCHX$^{15}_2$, —OCH$_2$X$^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{16}$, R$^{17}$, R$^{18}$, and R$^{19}$ are independently hydrogen, halogen, —CX$_3$, —CHX$_2$, —CH$_2$X, —OCX$_3$, —OCHX$_2$, —OCH$_2$X, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{16}$ and R$^{17}$ substituents bonded to the same nitrogen atom may optionally be joined to form a substituted or unsubstituted heterocycloalkyl or substituted or unsubstituted heteroaryl;

R⁴ is independently hydrogen, a —CX⁴₃, —CHX⁴₂, —CH₂X⁴, —CN, —C(O)H, —C(O)OH, —C(O)NH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

m15 and v15 are independently 1 or 2;
n15 is independently an integer from 0 to 4;
z is an integer from 0 to 4;
X¹⁵ is independently —Cl, —Br, —I, or —F.

3. The compound of claim 2, wherein R¹⁵ is independently a halogen, —CX¹⁵₃, —CHX¹⁵₂, —CH₂X¹⁵, —CN, —NHNH₂, —NO₂, —NH₂, —C(O)H, —C(O)OH, —C(O)NH₂, —OH, —NHC(O)OH, —OCX¹⁵₃, —OCHX¹⁵₂, —OCH₂X¹⁵, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₀ aryl, or substituted or unsubstituted 5 to 10 membered heteroaryl.

4. The compound of claim 2, wherein R¹⁵ is independently a halogen, —CX¹⁵₃, —CHX¹⁵₂, —CH₂X¹⁵, —CN, —NH₂, —OH, unsubstituted C₁-C₄ alkyl, or unsubstituted 2 to 4 membered heteroalkyl.

5. The compound of claim 1, having the formula:

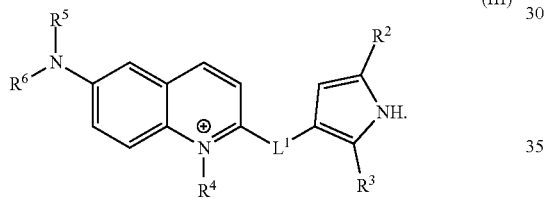

(III)

6. The compound of claim 1, wherein R² is independently a hydrogen, halogen, —CX²₃, —CHX²₂, —CH₂X², —CN, —NO₂, —NH₂, —OH, —OCX²₃, —OCHX²₂, —OCH₂X², substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₀ aryl, or substituted or unsubstituted 5 to 10 membered heteroaryl.

7. The compound of claim 1, wherein R³ is independently a hydrogen, halogen, —CX³₃, —CHX³₂, —CH₂X³, —CN, —NO₂, —NH₂, —OH, —OCX³₃, —OCHX³₂, —OCH₂X³, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₀ aryl, or substituted or unsubstituted 5 to 10 membered heteroaryl.

8. The compound of claim 1, wherein R⁴ is independently hydrogen, —CF₃, or substituted or unsubstituted C₁-C₄ alkyl.

9. The compound of claim 1, wherein R⁵ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

10. The compound of claim 1, wherein R⁶ is a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

11. The compound of claim 1, wherein L' is independently a bond, substituted or unsubstituted alkylene, substituted or unsubstituted alkenylene, substituted or unsubstituted heteroalkylene, or substituted or unsubstituted heteroalkenylene.

12. The compound of claim 1, wherein the compound is:

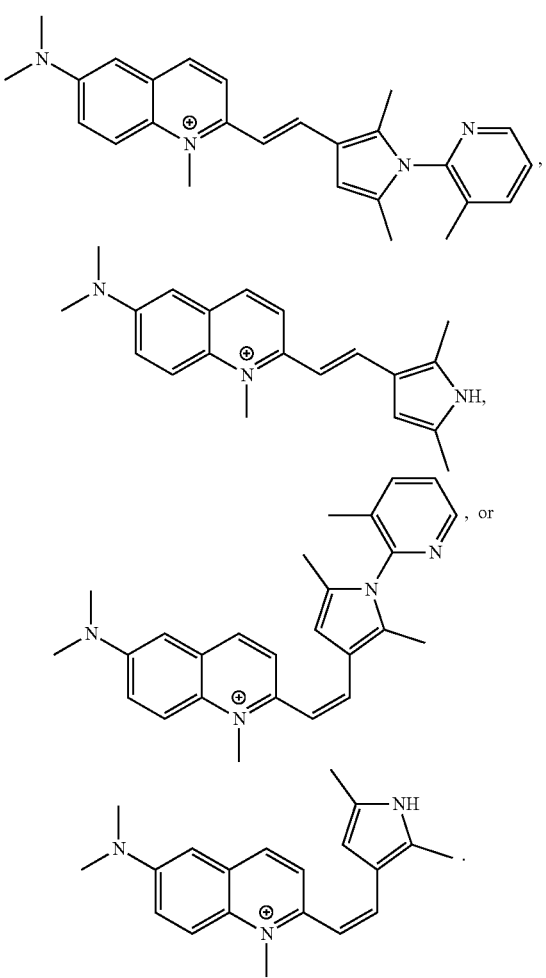

13. The compound of claim 1, wherein said compound is an antagonist of a nuclear receptor.

14. The compound of claim 1, wherein said compound is an antagonist of an androgen receptor.

15. A pharmaceutical composition comprising a compound of claim 1, or a pharmaceutically acceptable salt thereof, and a pharmaceutically acceptable excipient.

16. A method of treating a disease associated with androgen receptor activity in a patient having said disease, said method comprising administering a therapeutically effective amount of a compound of claim 1, or a pharmaceutically acceptable salt thereof.

17. A method of treating cancer associated with androgen receptor activity in a patient having said cancer, said method comprising administering a therapeutically effective amount of a compound of claim 1, or a pharmaceutically acceptable salt thereof.

18. The method of claim 17, wherein said cancer is prostate cancer.

19. The method of claim 17, wherein said cancer is hormone sensitive prostate cancer or hormone refractory prostate cancer.

20. A method of inhibiting androgen receptor activity, said method comprising contacting an androgen receptor with an effective amount of a compound of claim 1.

* * * * *